United States Patent
Bogusky et al.

(10) Patent No.: US 9,844,412 B2
(45) Date of Patent: Dec. 19, 2017

(54) METHODS AND APPARATUS FOR CONSTRUCTING ENDOSCOPIC DEVICE WITH HELICAL LUMEN DESIGN

(71) Applicant: Auris Surgical Robotics, Inc., Redwood City, CA (US)

(72) Inventors: Joseph Daniel Bogusky, San Jose, CA (US); Enrique Romo, Dublin, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 607 days.

(21) Appl. No.: 14/542,387

(22) Filed: Nov. 14, 2014

(65) Prior Publication Data

US 2015/0164595 A1    Jun. 18, 2015

Related U.S. Application Data

(63) Continuation of application No. 14/523,760, filed on Oct. 24, 2014.

(Continued)

(51) Int. Cl.
*A61B 19/00* (2006.01)
*A61B 1/005* (2006.01)
(Continued)

(52) U.S. Cl.
CPC ........ *A61B 19/2203* (2013.01); *A61B 1/0016* (2013.01); *A61B 1/0057* (2013.01); *A61B 1/00071* (2013.01); *A61B 1/00149* (2013.01); *A61B 1/018* (2013.01); *A61B 34/30* (2016.02); *A61B 34/37* (2016.02); *A61B 34/71* (2016.02);
(Continued)

(58) Field of Classification Search
CPC ......... A61B 34/30; A61B 34/37; A61B 90/30; A61B 34/71; A61B 1/00071; A61B 1/0016; A61B 1/0057; A61B 1/018; A61B 1/00149; A61B 2034/301; A61B 2034/2051; A61B 90/361; A61B 2034/306; A61M 25/0009; A61M 25/0012
See application file for complete search history.

(56) References Cited

U.S. PATENT DOCUMENTS

| | | |
|---|---|---|
| 4,597,388 A | 7/1986 | Koziol et al. |
| 4,745,908 A | 5/1988 | Wardle |

(Continued)

FOREIGN PATENT DOCUMENTS

| | | |
|---|---|---|
| JP | H09224951 A | 9/1997 |
| WO | WO 92/14411 A1 | 9/1992 |

(Continued)

OTHER PUBLICATIONS

European Extended Search Report, European Application No. 14856482.6, dated Feb. 8, 2017, 8 pages.

(Continued)

*Primary Examiner* — Ryan J Walters
(74) *Attorney, Agent, or Firm* — Knobbe Martens Olson & Bear LLP

(57) ABSTRACT

An endolumenal robotic system provides the surgeon with the ability to drive a robotically-driven endoscopic device to a desired anatomical position in a patient without the need for awkward motions and positions, while also enjoying improved image quality from a digital camera mounted on the endoscopic device.

22 Claims, 59 Drawing Sheets

Related U.S. Application Data

(60) Provisional application No. 61/895,312, filed on Oct. 24, 2013, provisional application No. 61/895,315, filed on Oct. 24, 2013, provisional application No. 61/895,602, filed on Oct. 25, 2013, provisional application No. 61/940,180, filed on Feb. 14, 2014, provisional application No. 62/019,816, filed on Jul. 1, 2014, provisional application No. 62/037,520, filed on Aug. 14, 2014.

(51) Int. Cl.
| | | |
|---|---|---|
| A61B 1/018 | (2006.01) | |
| A61M 25/00 | (2006.01) | |
| A61B 90/30 | (2016.01) | |
| A61B 34/37 | (2016.01) | |
| A61B 1/00 | (2006.01) | |
| A61B 1/05 | (2006.01) | |
| A61B 17/00 | (2006.01) | |
| A61B 34/00 | (2016.01) | |
| A61B 34/20 | (2016.01) | |
| A61B 34/30 | (2016.01) | |
| A61B 90/00 | (2016.01) | |

(52) U.S. Cl.
CPC ......... *A61B 90/30* (2016.02); *A61M 25/0009* (2013.01); *A61M 25/0012* (2013.01); *A61B 1/00045* (2013.01); *A61B 1/05* (2013.01); *A61B 90/361* (2016.02); *A61B 2017/00477* (2013.01); *A61B 2017/00526* (2013.01); *A61B 2034/2048* (2016.02); *A61B 2034/2051* (2016.02); *A61B 2034/301* (2016.02); *A61B 2034/306* (2016.02); *A61B 2034/742* (2016.02); *Y10T 29/49815* (2015.01)

(56) References Cited

U.S. PATENT DOCUMENTS

| | | | |
|---|---|---|---|
| 4,905,673 | A | 3/1990 | Pimiskern |
| 4,907,168 | A | 3/1990 | Boggs |
| 5,313,934 | A | 5/1994 | Wiita |
| 5,425,735 | A | 6/1995 | Rosen et al. |
| 5,472,406 | A | 12/1995 | De La Torre et al. |
| 5,507,725 | A | 4/1996 | Savage et al. |
| 5,572,999 | A | 11/1996 | Funda et al. |
| 5,662,590 | A | 9/1997 | De La Torre et al. |
| 5,695,500 | A | 12/1997 | Taylor et al. |
| 6,033,371 | A | 3/2000 | Torre et al. |
| 6,157,853 | A | 12/2000 | Blume |
| 6,326,616 | B1 | 12/2001 | Andrien et al. |
| 6,398,792 | B1 | 6/2002 | O'Connor |
| 6,406,486 | B1 | 6/2002 | De La Torre et al. |
| 6,436,107 | B1 | 8/2002 | Wang et al. |
| 6,554,793 | B1 | 4/2003 | Pauker et al. |
| 6,638,246 | B1 | 10/2003 | Naimark et al. |
| 6,671,581 | B2 | 12/2003 | Niemeyer et al. |
| 6,736,784 | B1 | 5/2004 | Menne et al. |
| 6,763,259 | B1 | 7/2004 | Hauger et al. |
| 6,827,712 | B2 | 12/2004 | Tovey |
| 7,087,061 | B2 | 8/2006 | Chernenko et al. |
| 7,344,528 | B1 | 3/2008 | Tu et al. |
| 7,351,193 | B2 | 4/2008 | Forman et al. |
| 7,725,214 | B2 | 5/2010 | Diolaiti |
| 7,883,475 | B2 | 2/2011 | Dupont et al. |
| 7,930,065 | B2 | 4/2011 | Blume |
| 7,967,799 | B2 | 6/2011 | Boukhny |
| 8,049,873 | B2 | 11/2011 | Hauger et al. |
| 8,224,484 | B2 | 7/2012 | Swarup et al. |
| 8,414,564 | B2 | 4/2013 | Goldshleger et al. |
| 8,518,024 | B2 | 8/2013 | Williams et al. |
| 9,427,551 | B2 * | 8/2016 | Leeflang ........... A61M 25/0012 |
| 2004/0030349 | A1 | 2/2004 | Boukhny |
| 2004/0135733 | A1 | 7/2004 | Chou et al. |
| 2005/0004515 | A1 | 1/2005 | Hart et al. |
| 2005/0070844 | A1 | 3/2005 | Chow et al. |
| 2005/0154262 | A1 | 7/2005 | Banik |
| 2005/0272975 | A1 | 12/2005 | Mcweeney et al. |
| 2007/0032906 | A1 | 2/2007 | Sutherland et al. |
| 2007/0135763 | A1 | 6/2007 | Musbach et al. |
| 2007/0299427 | A1 | 12/2007 | Yeung et al. |
| 2008/0051629 | A1 | 2/2008 | Sugiyama |
| 2008/0065103 | A1 | 3/2008 | Cooper |
| 2008/0065109 | A1 | 3/2008 | Larkin |
| 2008/0097293 | A1 | 4/2008 | Chin et al. |
| 2008/0114341 | A1 | 5/2008 | Thyzel |
| 2008/0177285 | A1 | 7/2008 | Brock et al. |
| 2008/0187101 | A1 | 8/2008 | Gertner |
| 2008/0228104 | A1 | 9/2008 | Uber et al. |
| 2008/0287918 | A1 | 11/2008 | Rosenman et al. |
| 2009/0099420 | A1 | 4/2009 | Woodley |
| 2009/0171271 | A1 | 7/2009 | Webster et al. |
| 2009/0248041 | A1 | 10/2009 | Williams et al. |
| 2009/0248043 | A1 | 10/2009 | Tierney et al. |
| 2009/0264878 | A1 | 10/2009 | Carmel et al. |
| 2009/0268015 | A1 | 10/2009 | Scott et al. |
| 2009/0312768 | A1 | 12/2009 | Hawkins et al. |
| 2009/0326322 | A1 | 12/2009 | Diolaiti |
| 2010/0030023 | A1 | 2/2010 | Yoshie |
| 2010/0036294 | A1 | 2/2010 | Mantell et al. |
| 2010/0073150 | A1 | 3/2010 | Olson et al. |
| 2011/0009779 | A1 | 1/2011 | Romano et al. |
| 2011/0028887 | A1 | 2/2011 | Fischer et al. |
| 2011/0040404 | A1 | 2/2011 | Diolaiti et al. |
| 2011/0046441 | A1 | 2/2011 | Wiltshire et al. |
| 2011/0106102 | A1 | 5/2011 | Balicki et al. |
| 2011/0261183 | A1 | 10/2011 | Ma |
| 2011/0306836 | A1 | 12/2011 | Ohline et al. |
| 2012/0123327 | A1 | 5/2012 | Miller |
| 2012/0136419 | A1 | 5/2012 | Zarembo et al. |
| 2012/0138586 | A1 | 6/2012 | Webster et al. |
| 2012/0239012 | A1 | 9/2012 | Laurent |
| 2012/0283747 | A1 | 11/2012 | Popovic |
| 2013/0018400 | A1 | 1/2013 | Milton |
| 2013/0035537 | A1 | 2/2013 | Wallace et al. |
| 2013/0144116 | A1 | 6/2013 | Cooper et al. |
| 2013/0345519 | A1 | 12/2013 | Piskun |
| 2014/0012276 | A1 | 1/2014 | Alvarez |
| 2014/0142591 | A1 | 5/2014 | Alvarez et al. |
| 2014/0276594 | A1 | 9/2014 | Tanner et al. |
| 2014/0309649 | A1 | 10/2014 | Alvarez et al. |
| 2014/0364870 | A1 | 12/2014 | Alvarez et al. |
| 2014/0379000 | A1 | 12/2014 | Romo et al. |
| 2015/0025539 | A1 | 1/2015 | Alvarez et al. |
| 2015/0051592 | A1 | 2/2015 | Kintz |
| 2015/0101442 | A1 | 4/2015 | Romo |
| 2015/0119637 | A1 | 4/2015 | Alvarez et al. |
| 2015/0119638 | A1 | 4/2015 | Yu et al. |
| 2015/0164594 | A1 | 6/2015 | Romo et al. |
| 2015/0164596 | A1 | 6/2015 | Romo et al. |
| 2016/0287346 | A1 | 10/2016 | Hyodo |

FOREIGN PATENT DOCUMENTS

| | | |
|---|---|---|
| WO | WO 03/096871 A2 | 11/2003 |
| WO | WO 2004/105849 A1 | 12/2004 |
| WO | WO 2011/161218 A1 | 12/2011 |
| WO | WO 2015/153111 A1 | 10/2015 |

OTHER PUBLICATIONS

European search report and search opinion dated Jul. 2, 2015 for EP Application No. 12856685.8.
Office action dated May 21, 2015 for U.S. Appl. No. 13/711,440.
Office action dated Jun. 11, 2015 for U.S. Appl. No. 14/158,548.
U.S. Appl. No. 14/578,082, filed Dec. 19, 2014, Alvarez et al.
U.S. Appl. No. 14/583,021, filed Dec. 24, 2014, Romo et al.
International search report and written opinion dated Jan. 27, 2015 for PCT Application No. US2014/062284.
U.S. Appl. No. 14/196,953, filed Mar. 4, 2014, Alvarez et al.

(56) References Cited

OTHER PUBLICATIONS

U.S. Appl. No. 14/201,610, filed Mar. 7, 2014, Romo.
U.S. Appl. No. 14/301,871, filed Jun. 11, 2014, Alvarez et al.
U.S. Appl. No. 14/458,042, filed Aug. 12, 2014, Kintz.
U.S. Appl. No. 14/479,095, filed Sep. 5, 2014, Romo et al.
U.S. Appl. No. 14/523,760, filed Oct. 24, 2014, Alvarez et al.
U.S. Appl. No. 14/542,373, filed Nov. 14, 2014, Romo et al.
U.S. Appl. No. 14/542,403, filed Nov. 14, 2014, Yu et al.
U.S. Appl. No. 14/542,429, filed Nov. 14, 2014, Romo et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology. 2012.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Oct. 7, 2014 for U.S. Appl. No. 13/711,440.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.
Verdaasdonk, et al. Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).

\* cited by examiner

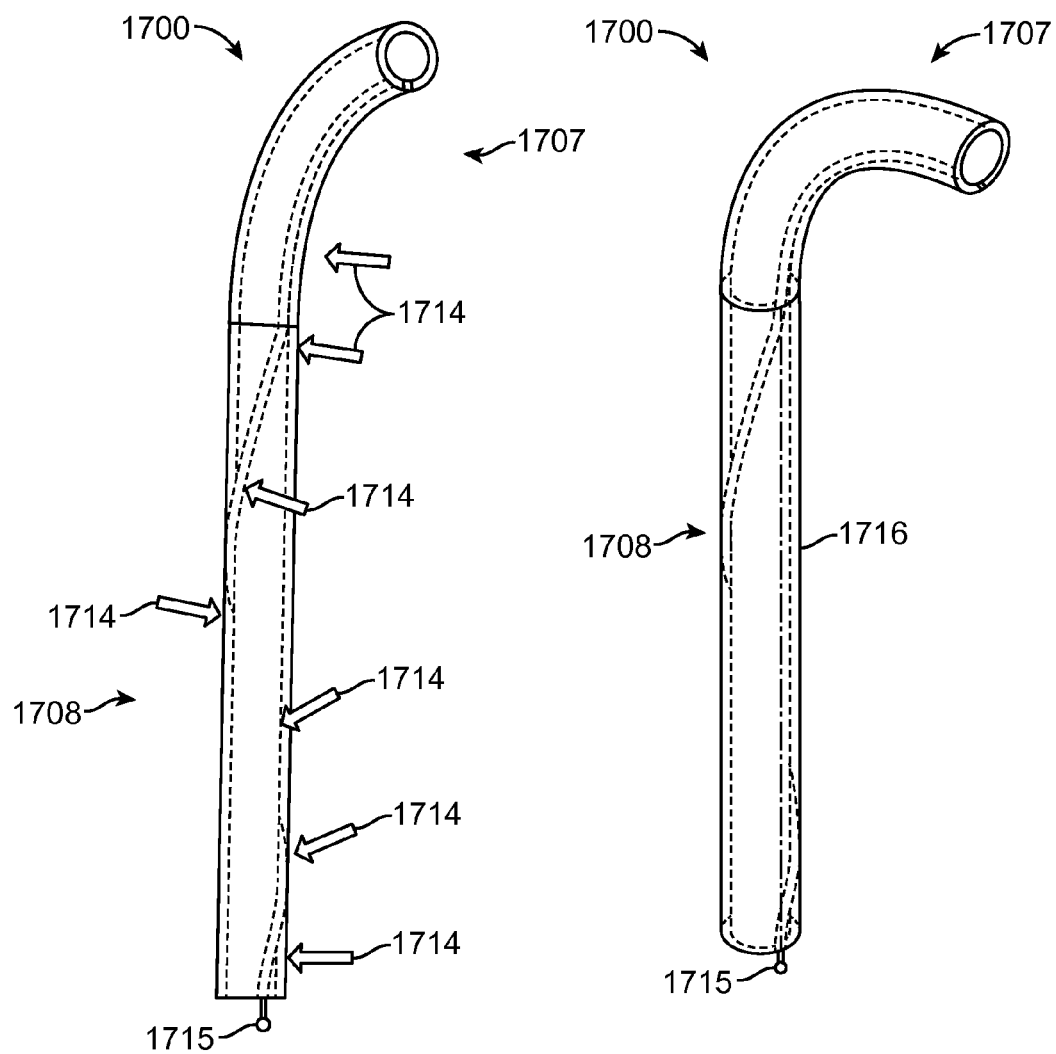

METHODS AND APPARATUS FOR CONSTRUCTING ENDOSCOPIC DEVICE WITH HELICAL LUMEN DESIGN

CROSS-REFERENCE TO RELATED APPLICATIONS

This application is a continuation of U.S. patent application Ser. No. 14/523,760, filed Oct. 24, 2014, which claims priority to U.S. Provisional Patent Application No. 61/895,312, filed Oct. 24, 2013; U.S. Provisional Patent Application No. 61/895,315, filed Oct. 24, 2013; U.S. Provisional Patent Application No. 61/895,602, filed Oct. 25, 2013; U.S. Provisional Patent Application No. 61/940,180, filed Feb. 14, 2014; U.S. Provisional Patent Application No. 62/019,816, filed Jul. 1, 2014; and U.S. Provisional Patent Application No. 62/037,520, filed Aug. 14, 2014; the entire contents of which are incorporated herein by reference.

This application is filed on the same day as and claims a common chain of priority as the following applications: U.S. Patent Application No. 14/542,373; U.S. patent application Ser. No. 14/542,403; and U.S. patent application Ser. No. 14/542,429.

BACKGROUND OF THE INVENTION

1. Field of the Invention

The field of the present application pertains to medical devices. More particularly, the field of the invention pertains to systems and tools for robotic-assisted endolumenal surgery.

2. Description of the Related Art

Endoscopy is a widely-used, minimally invasive technique for both imaging and delivering therapeutics to anatomical locations within the human body. Typically a flexible endoscope is used to deliver tools to an operative site inside the body—e.g., through small incisions or a natural orifice in the body (nasal, anal, vaginal, urinary, throat, etc.)—where a procedure is performed. Endoscopes may have imaging, lighting and steering capabilities at the distal end of a flexible shaft enabling navigation of non-linear lumens or pathways.

To assist with the navigation, the endoscopes often have a means to articulate a small distal bending section. Today's endoscopic devices are typically hand held devices with numerous levers, dials, and buttons for various functionalities, but offer limited performance in terms of articulation. For control, physicians control the position and progress of the endoscope by manipulating the leavers or dials in concert with twisting the shaft of the scope. These techniques require the physician to contort their hands and arms when using the device to deliver the scope to the desired position. The resulting arm motions and positions are awkward for physicians; maintaining those positions can also be physically taxing. Thus, manual actuation of bending sections is often constrained by low actuation force and poor ergonomics.

There are additional challenges with today's endoscopic devices. Today's endoscopes typically require support personnel to both deliver, operate and remove operative, diagnostic or therapeutic devices from the scope while the physician maintains the desired position. Today's endoscopes utilize pull wires that create issues with curve alignment and muscling. Some procedures require fluoroscopy or segmented CT scans to assist in navigating to the desired location, particularly for small lumen navigation.

Therefore, it would be beneficial to have a system and tools for endolumenal procedures that provide improved ergonomics, usability, and navigation.

SUMMARY OF THE INVENTION

In one aspect, the present invention provides for a system performing robotically-assisted surgical procedures that comprises a first robotic arm with a proximal end and a distal section, a first mechanism changer interface coupled to the distal section of the first robotic arm, a first instrument device manipulator coupled to the first mechanism changer interface, the first instrument device manipulator being configured to operate robotically-driven tools that are configured to perform surgical procedures at an operative site in a patient, and wherein the first instrument device manipulator comprises a drive unit.

In related devices, the drive unit comprises a motor. In some embodiments, the first instrument device manipulator is configured to be releasably disengaged from the mechanism changer interface and the first robotic arm.

In related devices, the first mechanism changer interface is configured to interface with a plurality of instrument device manipulators. In some embodiments, first mechanism changer interface is configured to convey electrical signals from the first robotic arm to the first instrument device manipulator.

In related devices, the present invention further comprises an endoscopic tool coupled to the first instrument device manipulator, the endoscopic tool comprising a primary elongated body. In some embodiments, an electromagnetic tracker is coupled to the distal section of the primary elongated body. In some embodiments, an accelerometer is coupled to the distal section of the primary elongated body.

In related devices, the primary elongated body comprises a working channel longitudinally aligned with a neutral axis of the primary elongated body, and a pull lumen aligned at an angle in a helix around the working channel. In some embodiments, the angle of the helix varies along the length of the primary elongated body. In some embodiments, the pull lumen contains an elongated tendon fixedly coupled to the distal section of the primary elongated body and responsive to the first instrument device manipulator.

In related devices, the endoscopic tool further comprises a secondary elongated body that is longitudinally aligned around the primary elongated body, wherein the primary elongated body comprises a proximal section and a distal section, and wherein a digital camera is coupled to the distal end. In some embodiments, the system further comprises a second robotic arm coupled to a second instrument device manipulator through a second mechanism changer interface, wherein the second instrument device manipulator is coupled to the endoscopic tool, and the first instrument device manipulator and the second instrument device manipulator are configured to align to form a virtual rail to operate the endoscopic tool. In some embodiments, the first instrument device manipulator operatively controls the secondary elongated body and the second instrument device manipulator operatively controls the primary elongated body. In some embodiments, the first robotic arm and the second robotic arm are coupled to a movable system cart. In some embodiments, the first robotic arm and the second robotic arm are coupled to an operating bed that is configured to hold the patient. In some embodiments, the system cart is configured to send sensor data to a command console and receive command signals from the command console. In some embodiments, the command console is separate from the system cart. In some embodiments, the command console comprises a display module and a control module for controlling the endoscopic tool. In some embodiments, the control module is a joystick controller.

BRIEF DESCRIPTION OF THE DRAWINGS

The invention will be described, by way of example, and with reference to the accompanying diagrammatic drawings, in which:

FIGS. 17I and 17J illustrate how the muscling and curve alignment phenomena is substantially resolved through the provision of a helixed section, in accordance with an embodiment of the present invention;

DETAILED DESCRIPTION OF THE PREFERRED EMBODIMENT

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

1. Overview.

An endolumenal surgical robotic system provides the surgeon with the ability to sit down in an ergonomic position and control a robotic endoscopic tool to the desired anatomical location within a patient without the need for awkward arm motions and positions.

The robotic endoscopic tool has the ability to navigate lumens within the human body with ease by providing multiple degrees of freedom at least two points along its length. The tool's control points provide the surgeon with significantly more instinctive control of the device as it navigates a tortuous path within the human body. The tip of the tool is also capable of articulation from zero to ninety degrees for all three hundred and sixty degrees of roll angles.

The surgical robotic system may incorporate both external sensor-based and internal vision-based navigation technologies in order to assist the physician with guidance to the desired anatomical location within the patient. The navigational information may be conveyed in either two-dimensional display means or three-dimensional display means.

2. System Components.

Figure 1:
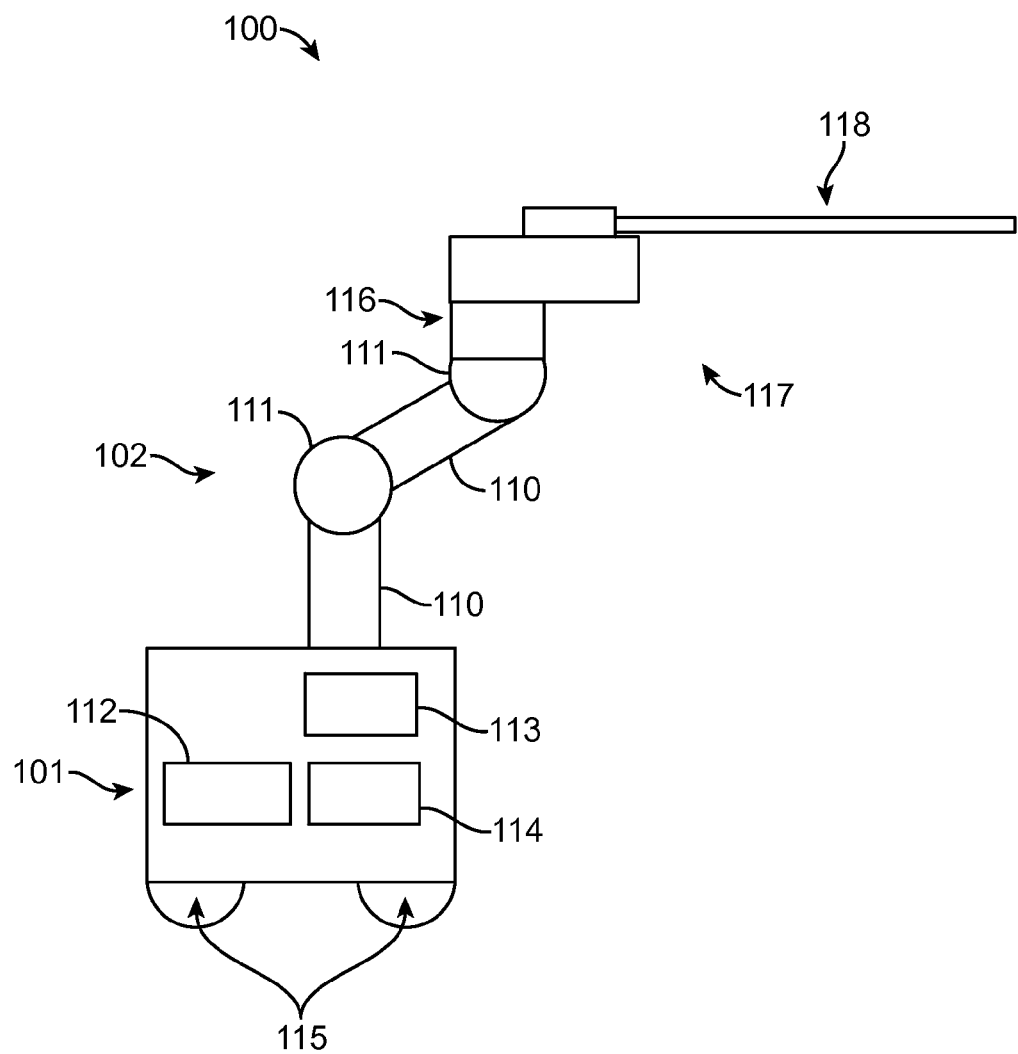
FIG. 1 illustrates a robotic endoscopic system, in accordance with an embodiment of the present invention.

FIG. 1 is a robotic endoscopic system, in accordance with an embodiment of the present invention. As shown in FIG. 1, robotic system 100 may comprises a system cart 101 with at least one mechanical arm, such as arm 102. The system cart 101 may be in communication with a remotely-located command console (not shown). In practice, the system cart 101 may be arranged to provide access to a patient, while a physician may control the system 100 from the comfort of the command console. In some embodiments, the system cart 100 may be integrated into the operating table or bed for stability and access to the patient.

Within system 100, arm 102 may be fixedly coupled to a system cart 101 that contains a variety of support systems, including control electronics, power sources and optical sources in some embodiments. The arm 102 may be formed from a plurality of linkages 110 and joints 111 to enable access to the patient's operative region. The system cart 103 may contain source of power 112, pneumatic pressure 113, and control and sensor electronics 114—including components such as central processing unit, data bus, control circuitry, and memory—and related actuators or motors that may drive arms such as arm 102. Power may be conveyed from the system cart 101 to the arm 102 using a variety of means known to one skilled in the art such as electrical wiring, gear heads, air chambers. The electronics 114 in system cart 101 may also process and transmit control signals communicated from a command console.

The system cart 101 may also be mobile, as shown by the wheels 115. In some embodiments, the system cart may capable of being wheeled to the desired location near the patient. System cart(s) 101 may be located in various locations in the operating room in order to accommodate space needs and facilitate appropriate placement and motion of modules and instruments with respect to a patient. This capability enables the arms to be positioned in locations where they do not interfere with the patient, doctor, anesthesiologist or any supportive surgical equipment required for the selected procedure. During procedures, the arms with instruments will work collaboratively via user control through separate control devices, which may include a command console with haptic devices, joystick, or customized pendants.

3. Mechanical Arms.

The proximal end of arm 102 may be fixedly mounted or coupled to the cart 101. Mechanical arm 102 comprises a plurality of linkages 110, connected by at least one joint per arm, such as joints 111. If mechanical arm 102 is robotic, joints 111 may comprise one or more actuators in order to affect movement in at least one degree of freedom. The arm 102, as a whole, preferably has more than three degrees of freedom. Through a combination of wires and circuits, each arm may also convey both power and control signals from system cart 101 to the instruments located at the end of their extremities.

In some embodiments, the arms may be fixedly coupled to the operating table with the patient. In some embodiments, the arms may be coupled to the base of the operating table and reach around to access patient.

In some embodiments, the mechanical arms may not be robotically-driven. In those embodiments, the mechanical arms are comprised of linkages and set up joints that use a combination of brakes and counter-balances to hold the position of the arms in place. In some embodiments, counter-balances may be constructed from gas springs or coil springs. Brakes, such as fail safe brakes, may be mechanical or electro-mechanical. In some embodiments, the arms may be gravity-assisted passive support arms.

Distally, each arm may be coupled to a removable Instrument Device Manipulator (IDM), such as 117, through a Mechanism Changer Interface (MCI), such as 116. In the preferred embodiment, the MCI 116 may contain connectors to pass pneumatic pressure, electrical power, electrical signals, and optical signals from the arm to the IDM 117. In some embodiments, MCI 116 may be as simple as a set screw or base plate connection.

IDM 117 may have a variety of means for manipulating a surgical instrument including, direct drive, harmonic drive, geared drives, belts and pulleys, or magnetic drives. One skilled in the art would appreciate that a variety of methods may be used control actuators on instrument devices.

Within the robotic system, the MCIs, such as 116, may be interchangeable with a variety of procedure-specific IDMs, such as 117. In this embodiment, the interchangeability of the IDMs allow robotic system 100 to perform different procedures.

Preferred embodiments may use a robotic arm with joint level torque sensing having a wrist at the distal end, such as Kuka AG's LBR5. These embodiments have a robotic arm with seven joints, with redundant joints provided to avoid potential arm collision with a patient, other robot arms, operating table, medical personal or equipment proximate to the operative field, while maintaining the wrist at the same pose so as not to interrupt an ongoing procedure. The skilled artisan will appreciate that a robotic arm with at least three degrees of freedom, and more preferably six or more degrees of freedom, will fall within the inventive concepts described herein, and further appreciate that more than one arm may be provided with additional modules, where each arm may be commonly or separately mounted on one or more carts.

4. Virtual Rail Configuration.

Arm 102 in system 100 may be arranged in a variety of postures for use in a variety of procedures. For example, in combination with another robotic system, the arm 102 of system 100 may be arranged to align its IDM to form a "virtual rail" that facilitates the insertion and manipulation of an endoscopic tool 118. For other procedures, the arms may be arranged differently. Thus, the use of arms in system 100 provides flexibility not found in robotic systems whose design is directly tied to specific medical procedure. The arms of system 100 provides potentially much greater stroke and stowage.

Figure 2A:
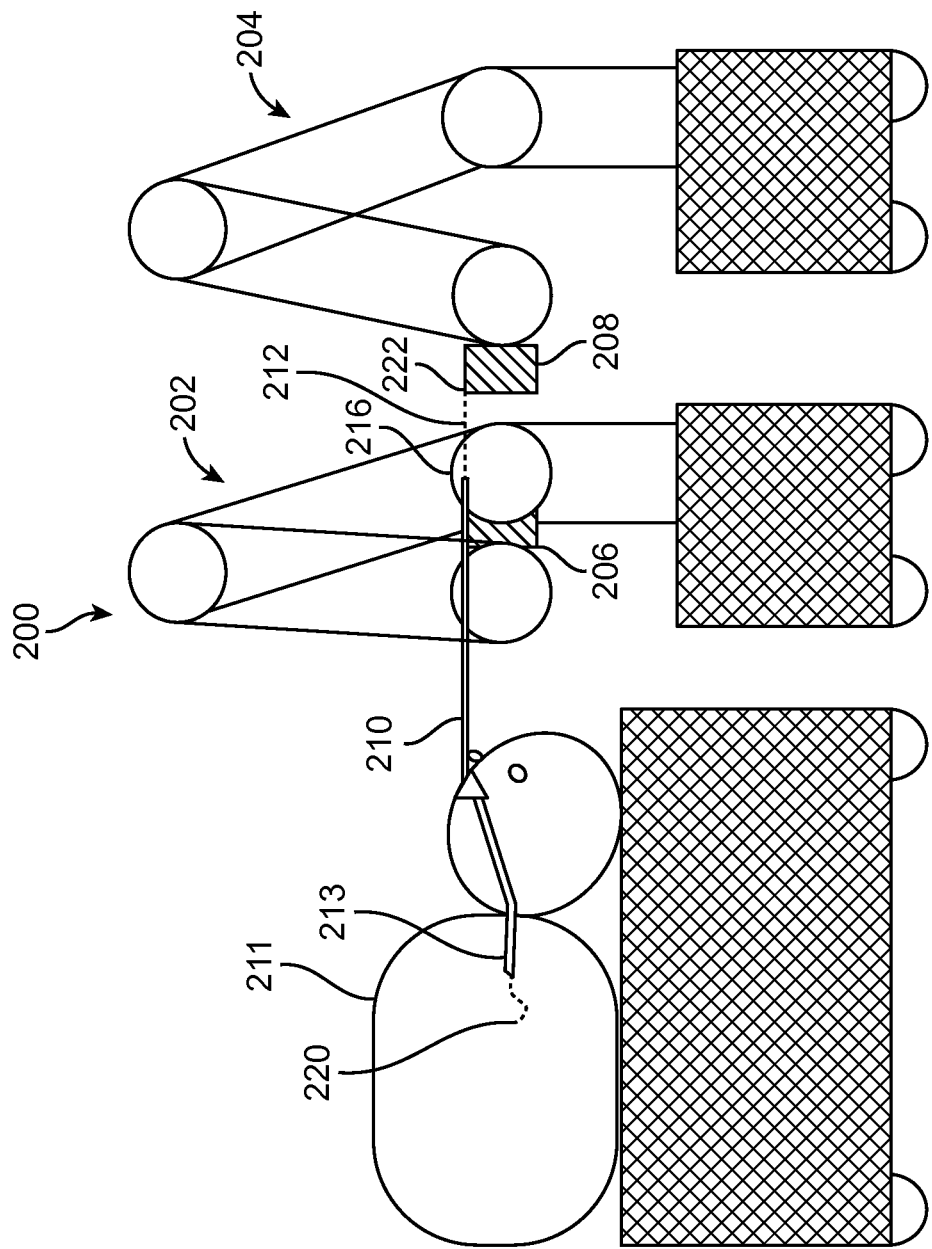
FIG. 2A illustrates a robotic surgery system in accordance with an embodiment of the present invention.

FIG. 2A illustrates a robotic surgery system 200 in accordance with an embodiment of the present invention. System 200 has first arm 202 and second arm 204 holding endoscopic tool bases 206 and 208, respectively. Tool base 206 has controllable endoscope sheath 210 operatively connected thereto. Tool base 208 has flexible endoscope leader 212 operatively connected thereto.

Arms 202 and 204 align tool bases 206 and 208 such that proximal end 216 of sheath 210 is distal of the proximal end 222 of leader 212, and such that leader 212 remains axially aligned with sheath 210 at an approximate angle of 180 degrees between the two arms, resulting in a "virtual rail" where the rail is approximately straight, or at 180 degrees. As will be described later, the virtual rail may have angles between 90-180 degrees. In one embodiment, sheath 210, with leader 212 slidingly disposed therethrough, is robotically inserted through, for example, a tracheal tube (not shown) in the mouth of and into patient 211, and ultimately into the patient's bronchial system, while continually maintaining the virtual rail during insertion and navigation. The arms may move sheath 210 and endoscope 212 axially relative to each other and in to or out of patient 211 under the control of a doctor (not shown) at a control console 203 (from FIG. 2B).

Navigation is achieved, for example, by advancing sheath 210 along with leader 212 into the patient 211, then leader 212 may be advanced beyond distal end 213 of the sheath, and the sheath 210 may then be brought even with the leader 212, until a desired destination is reached. Other modes of navigation may be used, such as and not by way of limitation using a guide wire through the working channel of the leader 212. The physician may be using any number of visual guidance modalities or combination thereof to aid navigation and performing the medical procedure, e.g., fluoroscopy, video, CT, MR etc. Distal end 220 of leader 212 may then be navigated to an operative site and tools are deployed through a longitudinally-aligned working channel within leader 212 to perform desired procedures. The virtual rail may be maintained during the navigation procedure and any subsequent operative procedures. Any number of alternative procedures that may require a tool or no tool at all can be performed using the flexible endoscope sliding through the sheath, as the skilled artisan will appreciate.

Figure 2B:
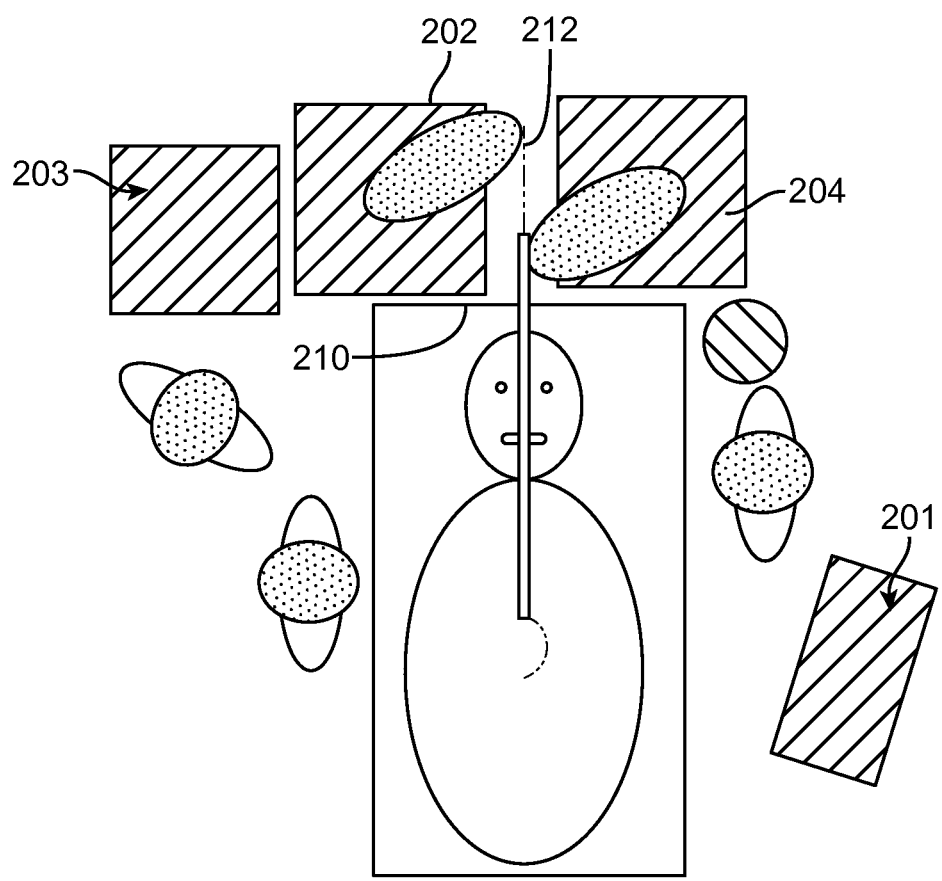
FIG. 2B illustrates an overhead view of system 200 where anesthesia cart 201 is provided towards the head of the patient.

FIG. 2B illustrates an overhead view of system 200 where anesthesia cart 201 is provided towards the head of the patient. Additionally, control console 203 with a user interface is provided to control sheath 210, endoscope leader 212, and the associated arms 202 and 204 and tool bases 206 and 208 (see FIG. 2A).

Figure 2C:
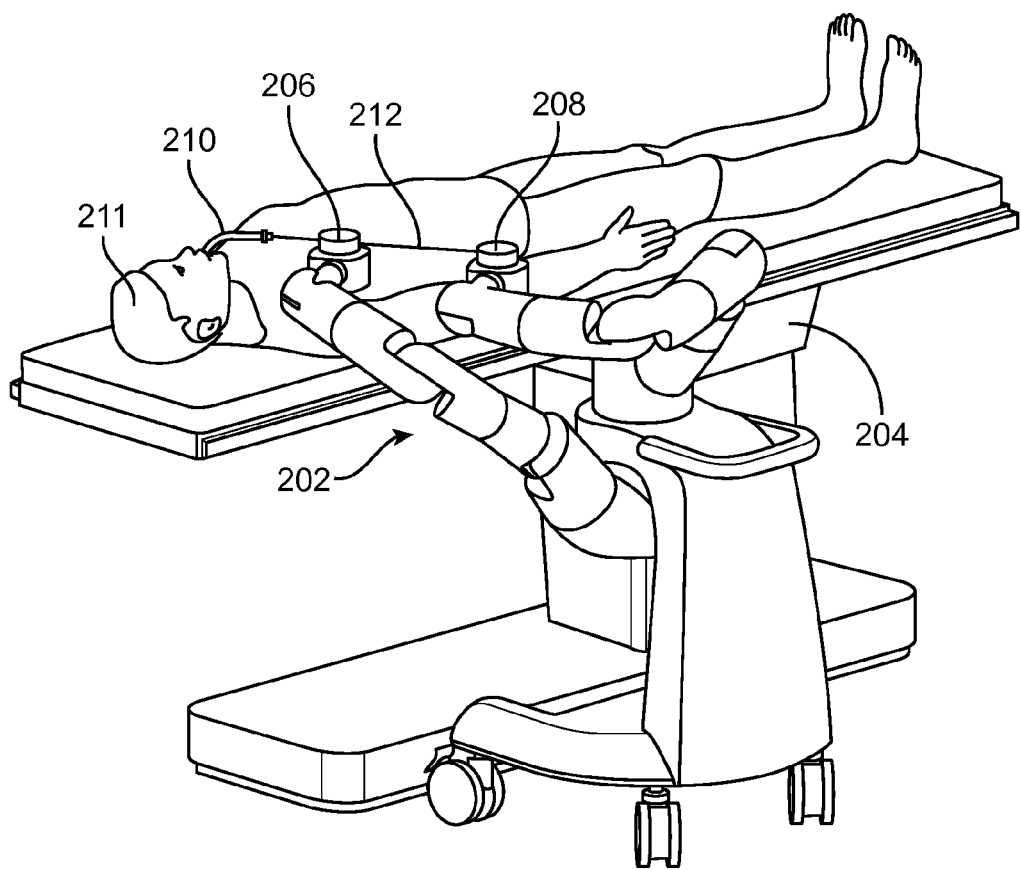
FIG. 2C shows an a view of system 200 in FIG. 2A.

FIG. 2C shows an angled view of system 200 in FIG. 2A. Tool modules 206 and 208 with associated sheath 210 and leader 212 are attached to arms 202 and 204 and arranged in a 180 degree virtual rail. The arms are shown on a single cart, which provides added compactness and mobility. As will be discussed later, tool bases 206 and 208 have pulley systems or other actuation systems to tension tendons in sheath 210 and leader 212 to steer their respective distal ends. Tool bases 206 and 208 may provide other desired utilities for the sheath and endoscope, such as pneumatic pressure, electrical, data communication (e.g., for vision), mechanical actuation (e.g., motor driven axels) and the like. These utilities may be provided to the tool bases through the arms, from a separate source or a combination of both.

Figure 2D:
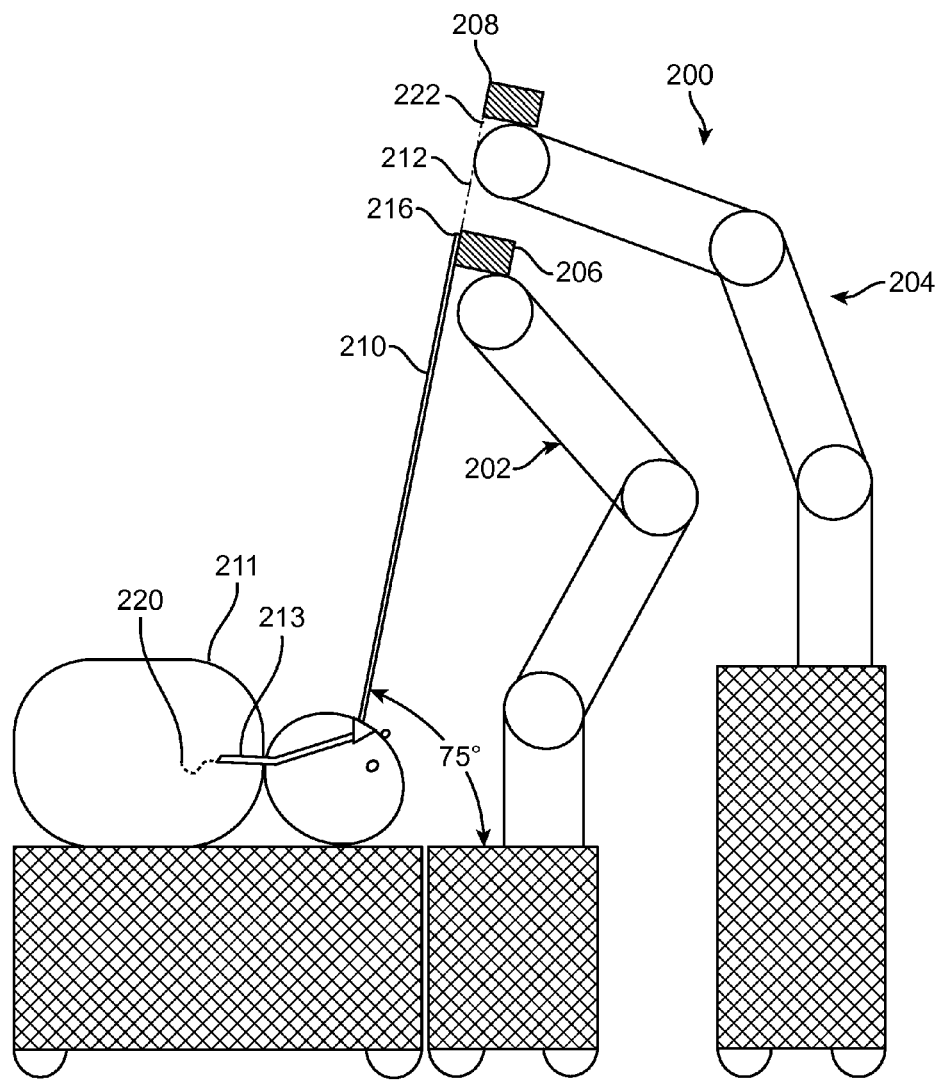
FIGS. 2D and 2E illustrate alternative arrangements of arms 202 and 204 showing the versatility of the robotic surgical system in accordance with embodiments of the present invention.
Figure 2E:
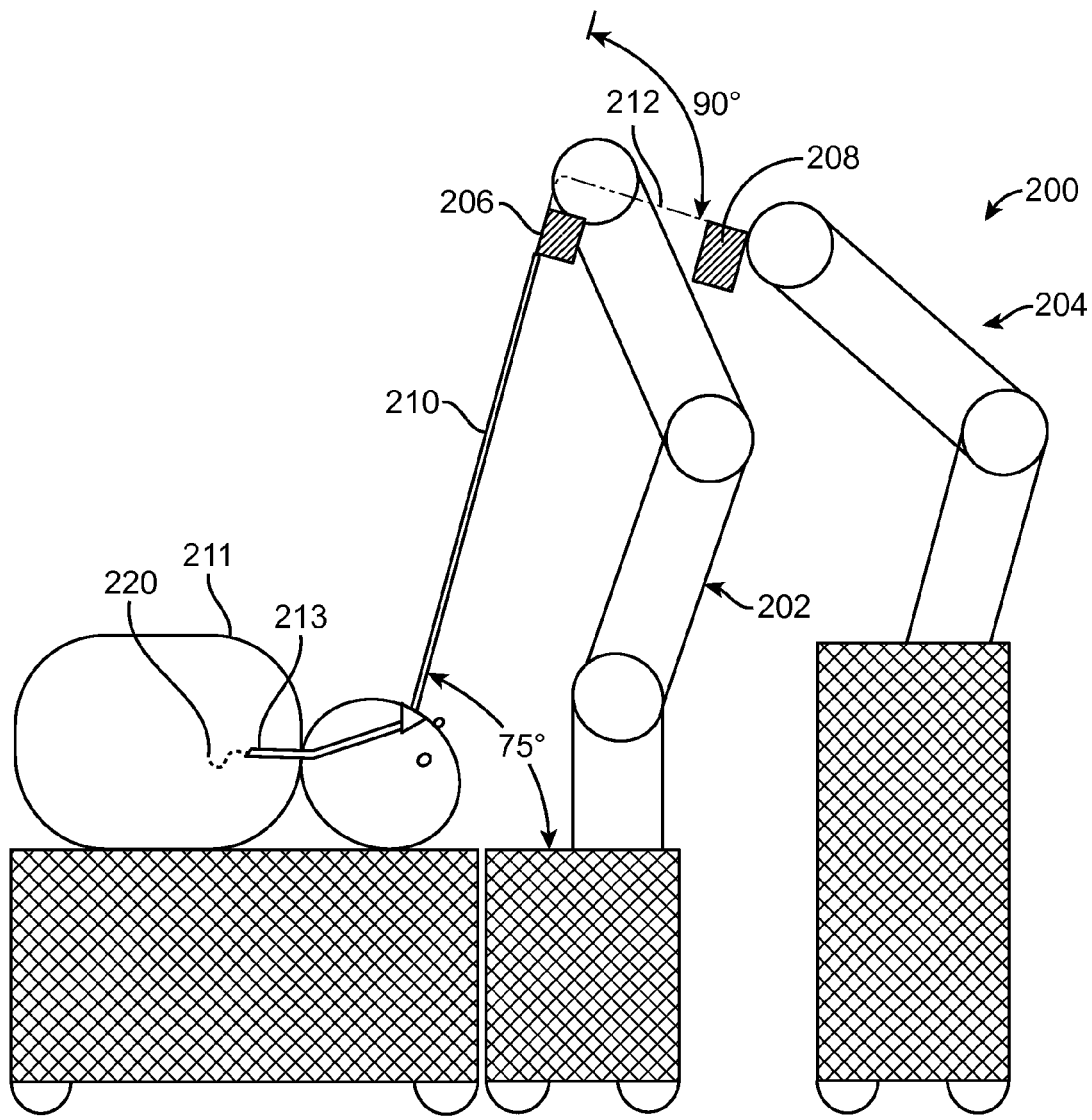

FIGS. 2D and 2E illustrate alternative arrangements of arms 202 and 204 showing the versatility of the robotic surgical system in accordance with embodiments of the present invention. In FIG. 2D, arms 202 and 204 may be extended to position the instrument (comprising sheath 210 and leader 212) to enter the mouth of patient 211 at 75 degrees from horizontal, while still maintaining a 180 degree virtual rail. This may be done during the procedure if required to accommodate space requirements within the room. The 75 degree angle was chosen for demonstrative purposes, not by way of limitation.

FIG. 2E shows an alternative arrangement of arms 202 and 204 where the tool bases 206 and 208 are aligned to create a virtual rail with a 90 degree angle, in accordance with an embodiment of the present invention. In this embodiment, the instrument (comprising sheath 210 and leader 212) enters the mouth of patient 213 at 75 degrees from horizontal. Tool bases 206 and 208 are aligned such that the leader 212 bends 90 degrees at tool base 206 prior to entering the mouth of patient 213. To facilitate the bend of leader 212, a rigid or semi-rigid structure, such as a tube, may be used to ensure smooth extension and retraction of the leader 212 within sheath 210. Extension and retraction of leader 212 within sheath 210 may be controlled by moving tool base 208 either closer or farther from tool base 206 along the linear path tracked by leader 212. Extension and retraction of sheath 210 may be controlled by moving tool base 206 closer or farther from patient 213 along the linear path tracked by sheath 210. To avoid unintended extension or retraction of leader 212 while extending or retracting sheath 210, tool base 208 may also be moved along a linear path parallel to sheath 210.

Virtual rails are useful in driving both rigid instrument and flexible instruments, and especially where there are telescoping requirements. The use of a virtual rail is not limited to a single rail but can consist of multiple virtual rails where the arms act in concert to maintain the individual virtual rails in performance of one or more procedures.

Figure 3A:
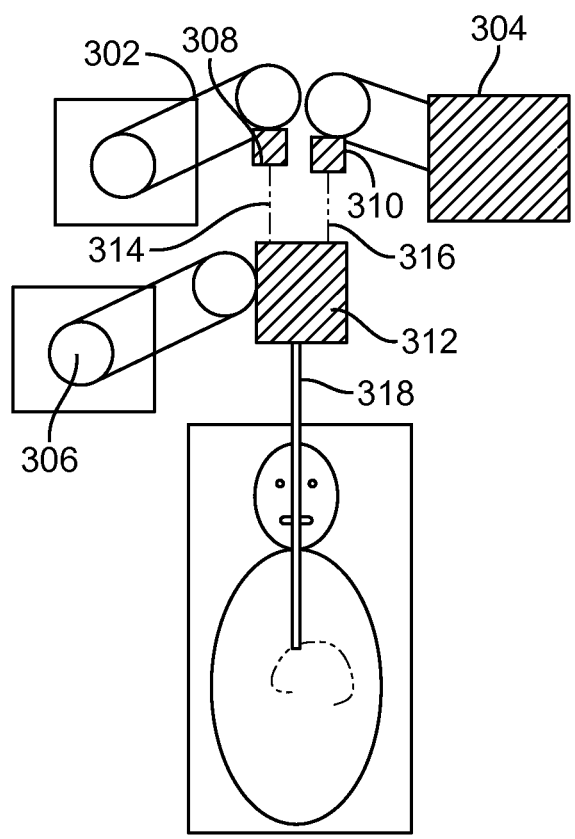
FIG. 3A illustrates an overhead view of a system with multiple virtual rails, in accordance with an embodiment of the present invention.

FIG. 3A illustrates an overhead view of a system with multiple virtual rails, in accordance with an embodiment of the present invention. In FIG. 3A, robot arms 302, 304 and 306 respectively hold tool bases 308, 310, and 312. Tool bases 308 and 310 may be operatively coupled to flexible tool 314 and tool 316. Tool 314 and tool 316 may be a telerobotically-controlled flexible endoscopic instruments. Tool base 312 may be operatively coupled to a dual lumen sheath 318, where each lumen receives tools 314 and 316. Arms 302 and 304 may each maintain a virtual rail with robotic arm 306, and movements of all three arms may be coordinated to maintain virtual rails and move tools 314, 316 and sheath 318 relative to each other and the patient.

Figure 3B:
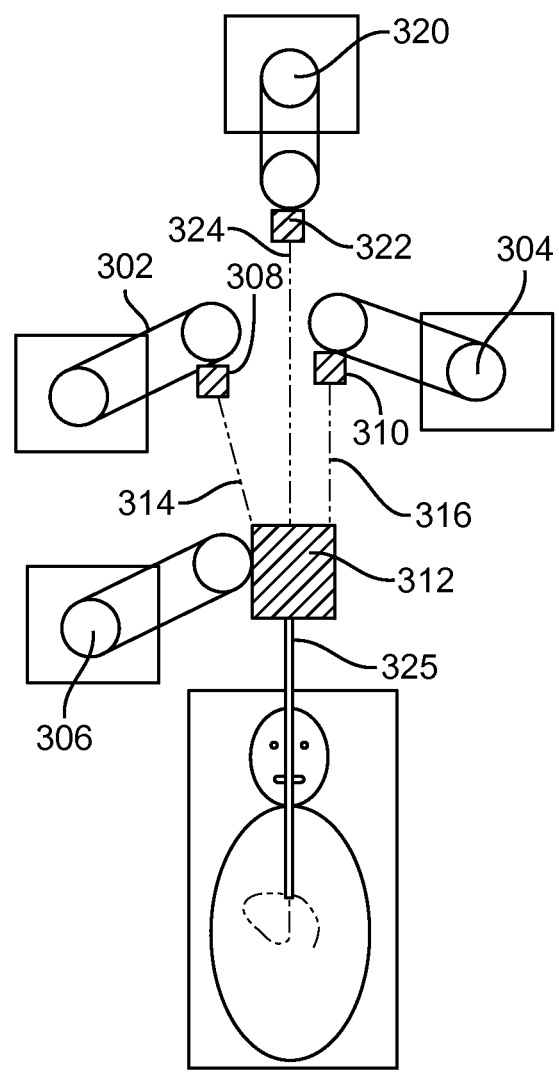
FIG. 3B illustrates the use of robotic surgery system from FIG. 3A with an additional robotic arm, associated tool base, and tool.

FIG. 3B illustrates the use of the robotic surgery system from FIG. 3A with an additional robotic arm 320 and associated tool base 322 and tool 324. In this embodiment sheath 325 may have three lumens. Alternatively, sheath 325 may comprise more than one sheath to provide access to tools 314, 316, and 324. As will be appreciated, the ability to increase or reduce the number of arms with associated modules and instruments permits a great number and flexibility of surgical configurations, which, in turn, permits re-purposing of expensive arms and use of multiple relatively-inexpensive modules to achieve great versatility at reduced expense.

Thus, to create the virtual rail, a plurality of arms and/or platforms may be utilized. Each platform/arm must be registered to the others, which can be achieved by a plurality of modalities including, vision, laser, mechanical, magnetic, or rigid attachment. In one embodiment, registration may be achieved by a multi-armed device with a single base using mechanical registration. In mechanical registration, an embodiment may register arm/platform placement, position, and orientation based on their position, orientation and placement relative to the single base. In another embodiment, registration may be achieved by a system with multiple base using individual base registration and "handshaking" between multiple robot arms. In embodiments with multiple bases, registration may be achieved by touching together arms from different bases, and calculating locations, orientation and placement based on (i) the physical contact and (ii) the relative locations of those bases. In some embodiments, registration targets may be used to match the position and orientations of the arms relative to each other. Through such registration, the arms and instrument driving mechanisms may be calculated in space relative to each other.

5. Mechanism Changer Interface.

Returning to FIG. 1, robotic surgical system 100 may be configured in a manner to provide a plurality of surgical system configurations, such as by changing IDM 117 and tool 118 (also known as an end effector). The system may comprise one or more mobile robotic platforms staged at different locations in the operative room, or at a convenient nearby location. Each platform may provide some or all of power, pneumatic pressure, illumination sources, data communication cables and control electronics for a robotic arm that is coupled to the platform, and the module may draw from these utilities as well. System 100 may alternatively have multiple arms 102 mounted on one or more mobile carts 101, or the arms may be mounted to the floor in order to provide a plurality of surgical configurations.

In addition to multiple arms and platforms, some embodiments are designed to readily exchange between multiple modules or end effector mechanisms. Various surgical procedures or steps within a procedure may require the use of different modules and the associated instrument sets, for example, exchanging between different sized sheath and endoscope combinations. Interchangeability allows the system to reconfigure for different clinical procedures or adjustments to surgical approaches.

Figure 4:
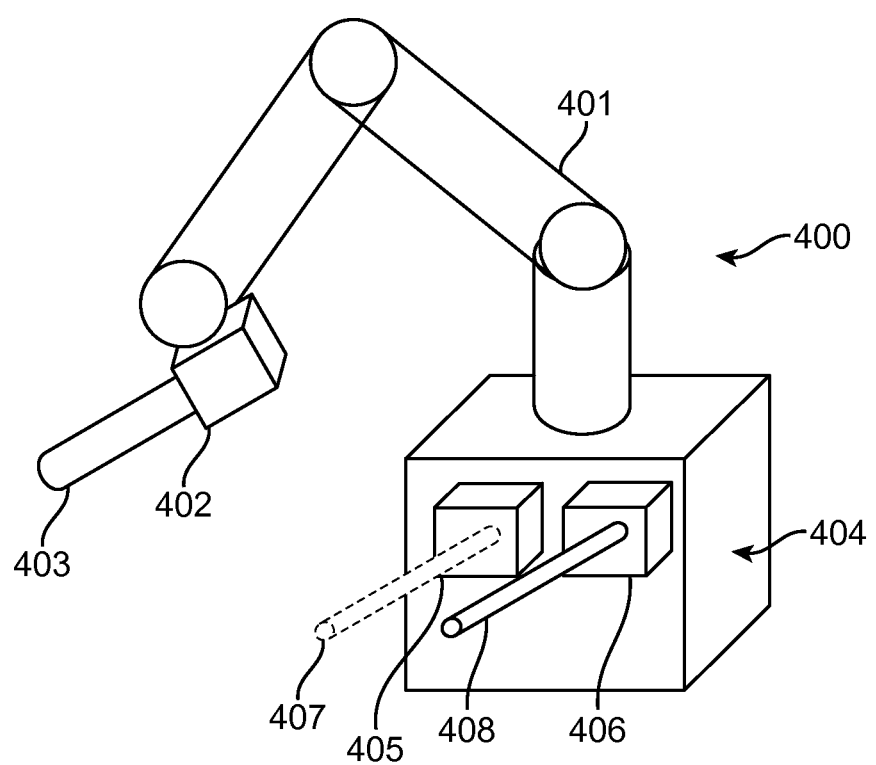
FIG. 4 illustrates a robotic surgery system with interchangeable IDMs and tools, in accordance with an embodiment of the present invention.

FIG. 4 illustrates a robotic surgery system with interchangeable IDMs and tools, in accordance with an embodiment of the present invention. Surgical system 400 has a mechanical arm 401 to which IDM 402 and tool 403 are attached. Attached to system cart 404, IDMs 405 and 406, and associated tools 407 and 408 may be exchanged onto robotic arm 401 or picked up by a different robotic arm (not shown) to be used alone in concert with another IDM and tool. Each IDM may be a dedicated electromechanical system which may be used to drive various types of instruments and tools for specified procedures. To drive instruments, each IDM may comprise an independent drive system, which may include a motor. They may contain sensors (e.g., RFID) or memory chips that record their calibration and application related information. A system calibration check may be required after a new mechanism is connected to the robot arm. In some embodiments, an IDM may control an endoscopic sheath or flexible endoscopic leader.

In FIG. 4, system 400 may exchange IDM 402 for IDMs 405 and 406 by itself through the use of global registration and sensors. In some embodiments, IDMs 406 and 408 are stored on system cart 404 at predetermined "docking stations" which are configured with identification and proximity sensors. Sensors at these stations may make use of technologies such as RFID, optical scanners (e.g., bar codes), EEPROMs, and physical proximity sensors to register and identify which IDMs are "docked" at the docking station. As robotic arm 401 and the IDM docking stations reside on system cart 404, the identification and proximity sensors allow the IDMs that are resting in the docking stations to be registered relative to the robotic arm(s). Similarly, in embodiments with multiple arms on a single system cart, multiple arms may access the IDMs on the docking station using the combination of registration system and sensors discussed above.

FIG. 5 illustrates a mechanism changer interface in a robotic system, in accordance with an embodiment of the present invention. FIG. 5A specifically illustrates an implementation of a mechanism changer interface coupled to a robotic arm in a robotic system, in accordance with an embodiment of the present invention. As shown in FIG. 5A, the distal portion of robotic arm 500 comprises an articulating joint 501 coupled to a "male" mechanism changer interface 502. Articulating joint 501 provides an additional degree of freedom with respect to manipulating an instrument device mechanism (not shown) that is configured to couple to robotic arm 500. Male mechanism changer interface 502 provides a male connector interface 503 that provides a strong, physical connection to the reciprocal female receptacle connector interface on the IDM (not shown). The spherical indentations on the male connector interface 503 physically couple to reciprocal indentations on the female receptacle interface on the IDM. The spherical indentations may be extended when pneumatic pressure is conveyed along robotic arm 500 into male mechanism changer interface 502. The male mechanism changer interface 502 also provides connections 504 for transferring for pneumatic pressure to the IDM. Additionally, this embodiment of the mechanism changer interface provides for alignment sensors 505 that ensure that the male mechanism changer interface 502 and its reciprocal female interface are properly aligned.

Figure 5A:
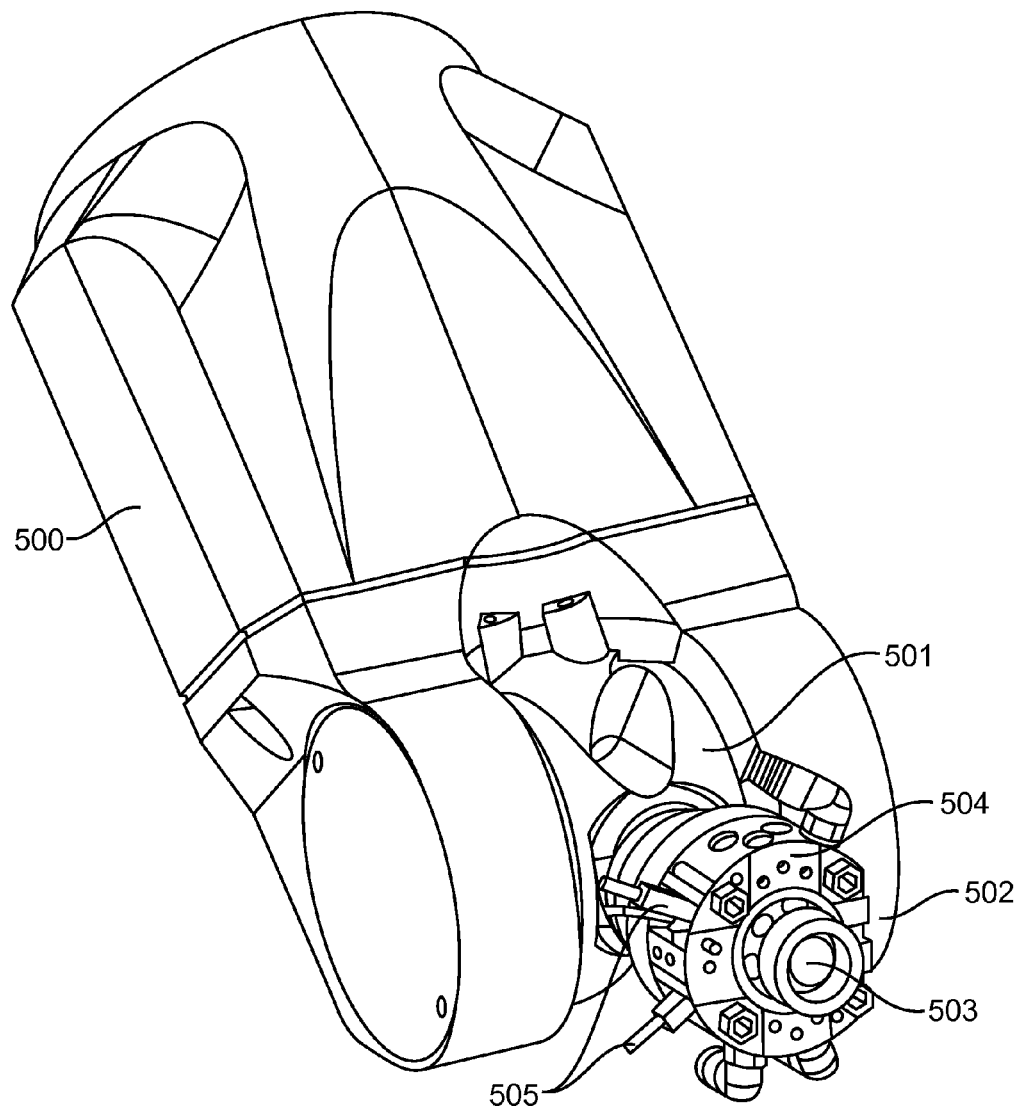
FIG. 5A illustrates an implementation of a mechanism changer interface coupled to a robotic arm in a robotic system, in accordance with an embodiment of the present invention.
Figure 5B:
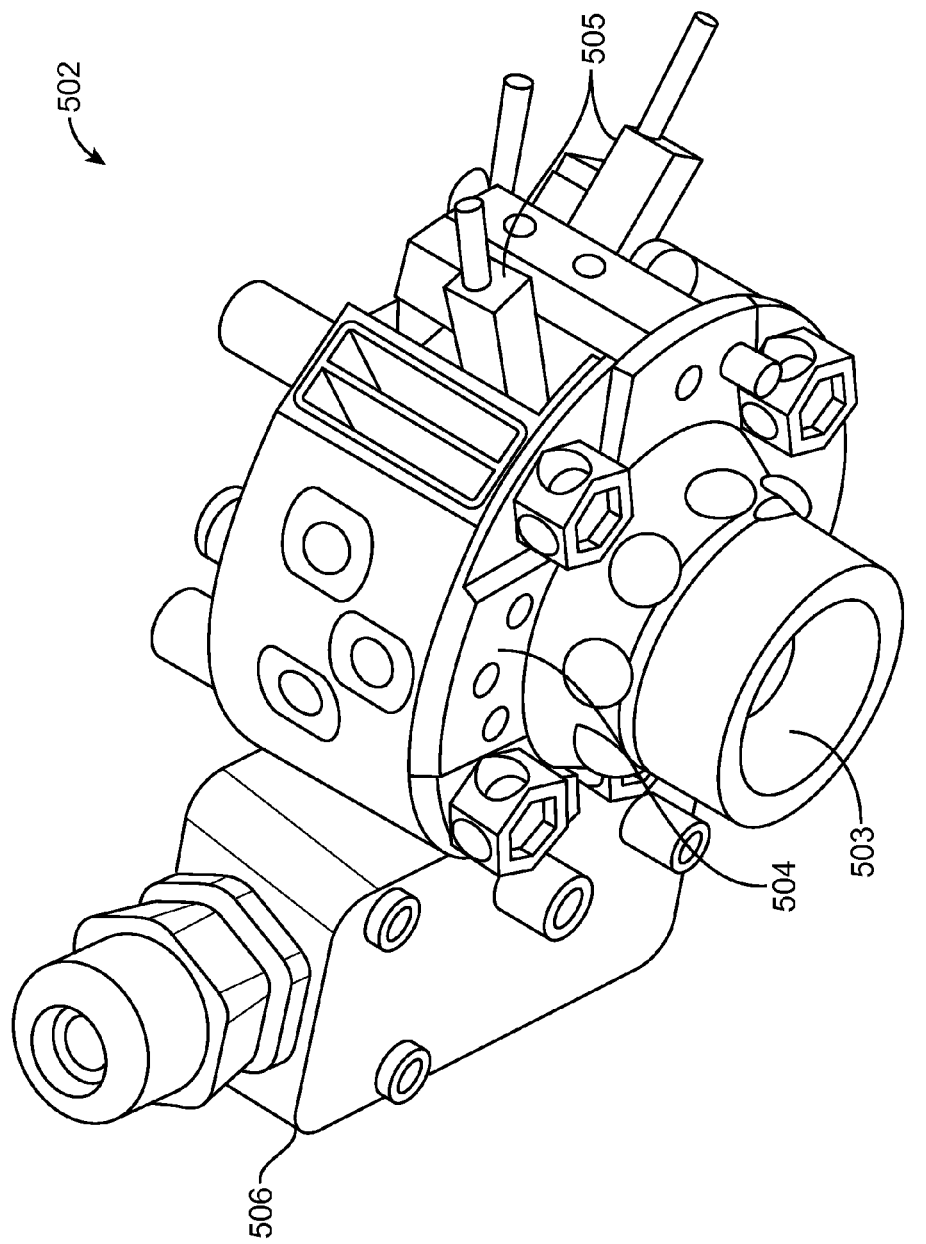
FIG. 5B illustrates an alternative view of male mechanism changer interface 502 from FIG. 5A.

FIG. 5B illustrates an alternative view of male mechanism changer interface 502 separated from robotic arm 500. As discussed with respect to FIG. 5A, male mechanism changer interface 502 provides for a flange-like male connector interface 503, pneumatic connectors 504, and alignment sensors 505. Additionally, an electrical interface 506 for connecting electrical signals to the reciprocal interface on the IDM (not shown).

Figure 5C:
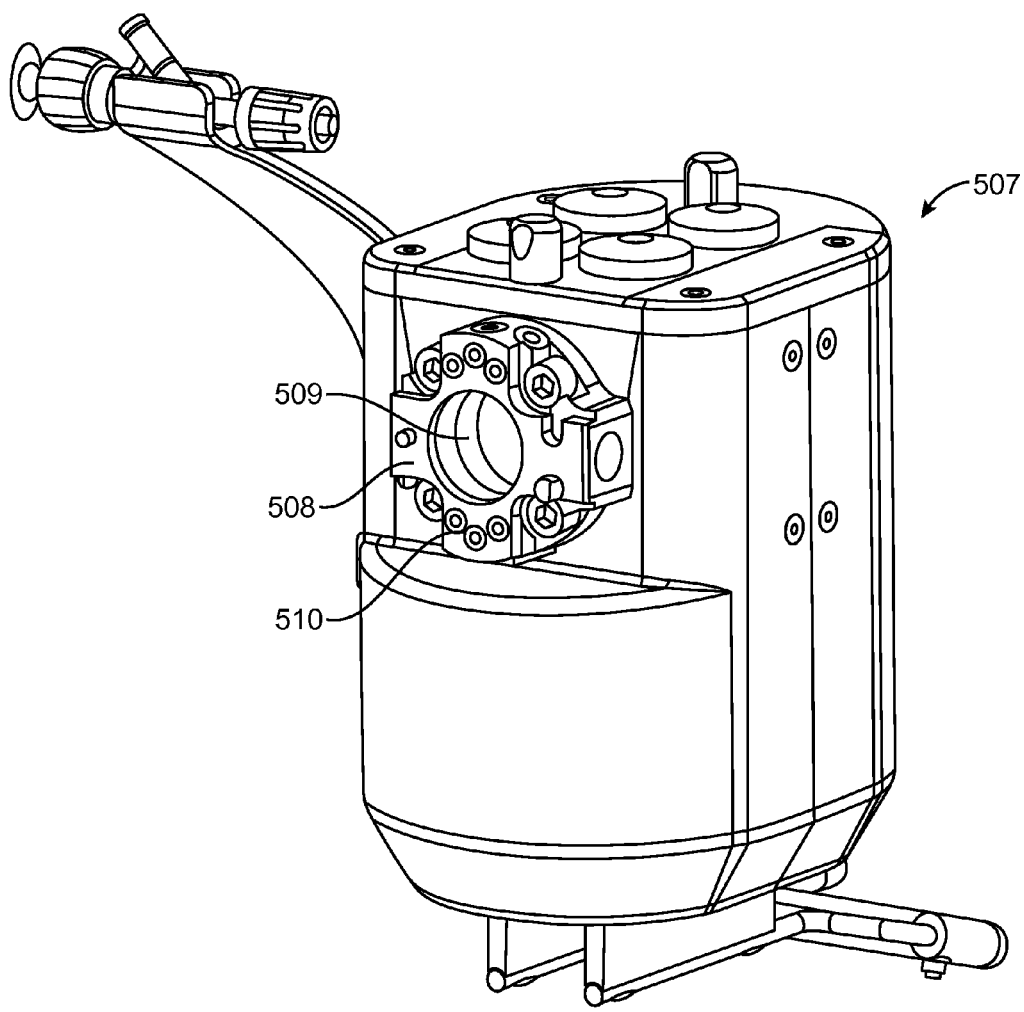
FIG. 5C illustrates a reciprocal female mechanism changer interface coupled to an instrument device manipulator for connecting with male mechanism changer interface 502 from FIGS. 5A and 5B.

FIG. 5C illustrates a reciprocal female mechanism changer interface coupled to an instrument device manipulator for connecting with male mechanism changer interface 502 from FIGS. 5A and 5B. As shown in FIG. 5C, instrument device manipulator 507 is coupled to a female mechanism changer interface 508 that is configured to connect to male mechanism changer interface 502 on robotic arm 500. Female mechanism changer interface 508 provides for female receptacle interface 509 that is designed to couple to the flange-like male connector interface 503 of male mechanism changer interface 502. The female receptacle interface 509 also provides a groove to grip the spherical indentations on the male connector interface 503. When pneumatic pressure is applied, spherical indentations on male connector 503 are extended, and male connector 503 and receptacle interfaces 509 securely couple the IDM 507 to the robotic arm 500. Reciprocal female mechanism changer interface 508 also provides with pneumatic connectors 510 to accept the pneumatic pressure conveyed from connectors 504.

Figure 5D:
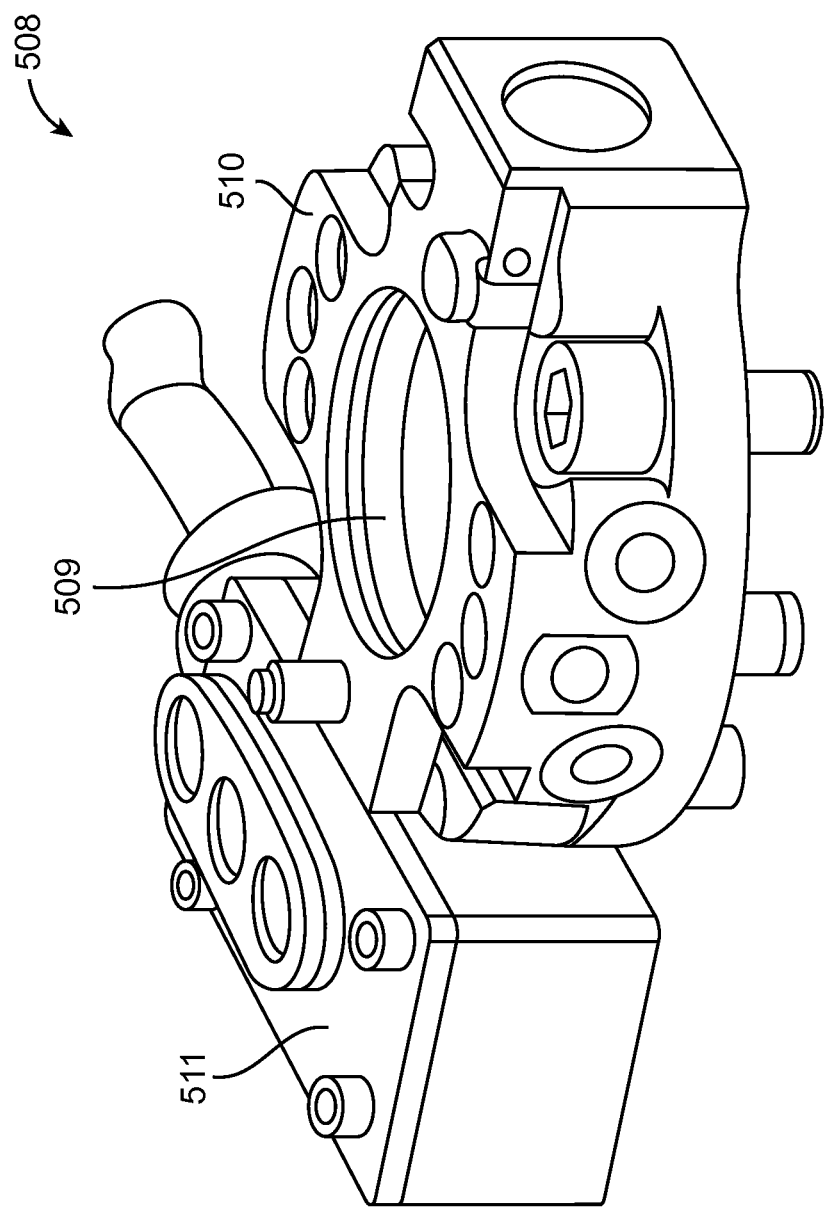
FIG. 5D illustrates an alternative view of female mechanism changer interface 508 from FIG. 5C.

FIG. 5D illustrates an alternative view of female mechanism changer interface 508 from FIG. 5C. As discussed earlier, reciprocal mechanism changer interface 508 contains a receptacle interface 509, pneumatic connectors 510 for interfacing with mechanism changer interface 502 on robotic arm 500. In addition, mechanism changer interface 508 also provides for an electrical module 511 for transmitting electrical signals—power, controls, sensors—to module 506 in mechanism changer interface 502.

Figure 6:
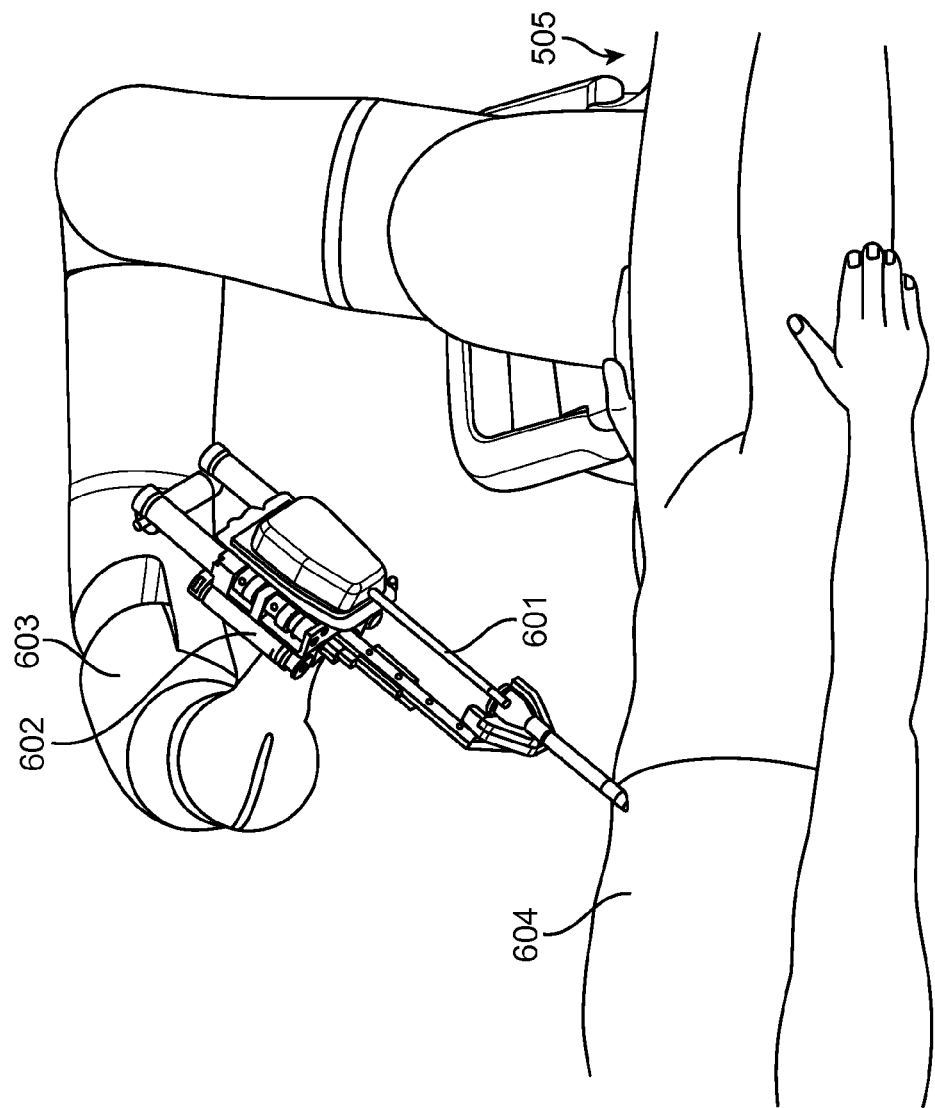
FIG. 6 illustrates a robotic surgery system that uses a single port laparoscopic instrument connected through an instrument interface on a single robotic arm that is directed at the abdomen of a patient, in accordance with an embodiment of the present invention.

FIGS. 6, 7, 8A, and 8B illustrate interchangeable modules that may be operated using system 400 from FIG. 4. FIG. 6 illustrates an embodiment of the present invention that uses a single port laparoscopic instrument 601 connected through an instrument interface 602 on a single robotic arm 603 that is directed at the abdomen 604 of a patient 605.

Figure 7:
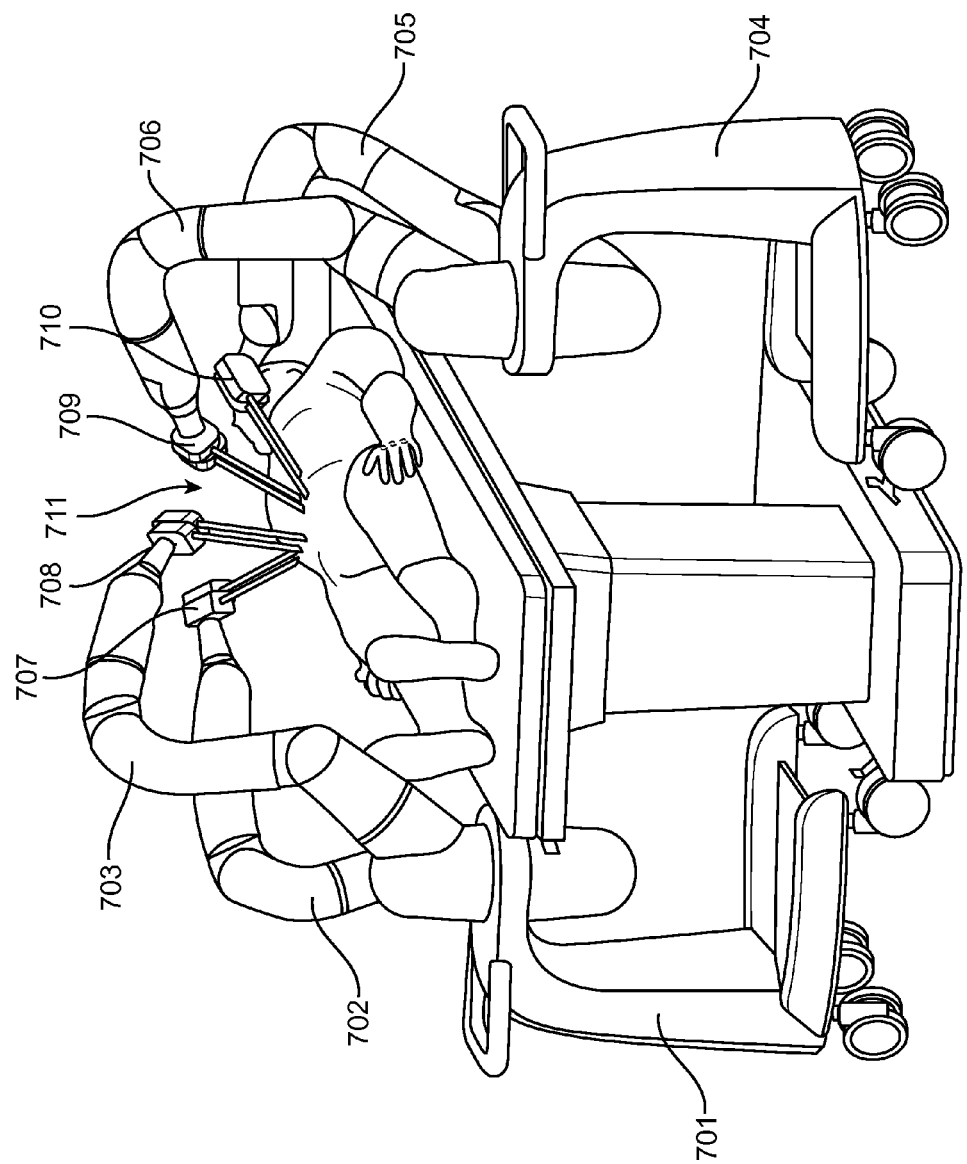
FIG. 7 illustrates a robotic surgery system with two sets of robotic subsystems, each with a pair of arms, in accordance with an embodiment of the present invention.

FIG. 7 illustrates an embodiment of the present invention with two sets of robotic subsystems 701 and 704, each with a pair of arms 702, 703 and 705, 706 respectively. Connected through instrument interfaces at the distal end of arms 702, 703, 705, 706 are laparoscopic instruments 707, 708, 709, 710 respectively, all instruments working together to perform procedures in an individual patient 711.

Figure 8A:
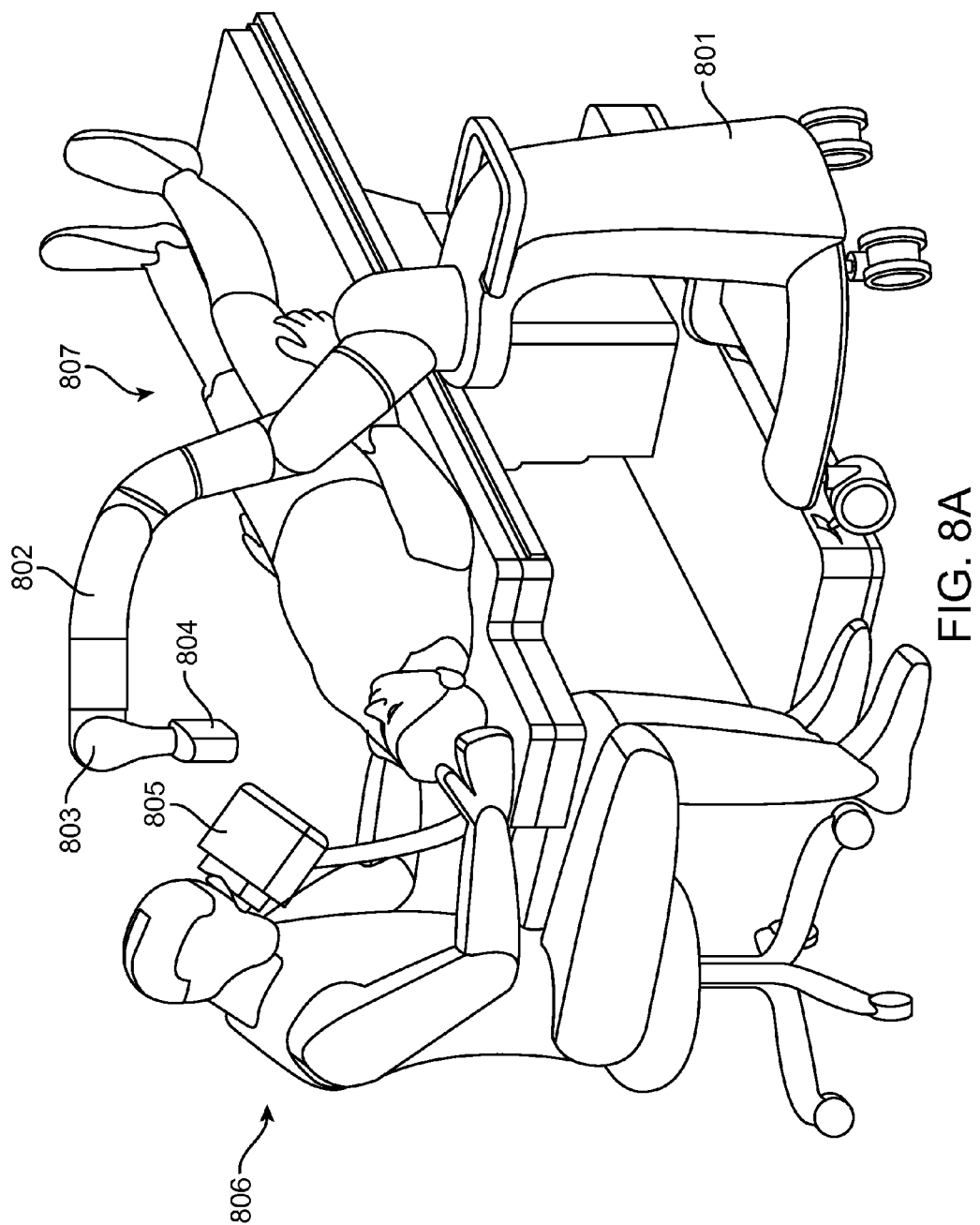
FIG. 8A illustrates a robotic surgery system with a subsystem with a single robotic arm, where a microscope tool is connected to the robotic arm through an instrument interface, in accordance with an embodiment of the present invention.

FIG. 8A illustrates an embodiment of the present invention with a subsystem 801 with a single robotic arm 802, where a microscope tool 804 connected to the robotic arm 802 through an instrument interface 803. In some embodiments, the microscopic tool 804 may be used in conjunction with a second microscope tool 805 used by a physician 806 to aid in visualizing the operational area of a patient 807.

Figure 8B:
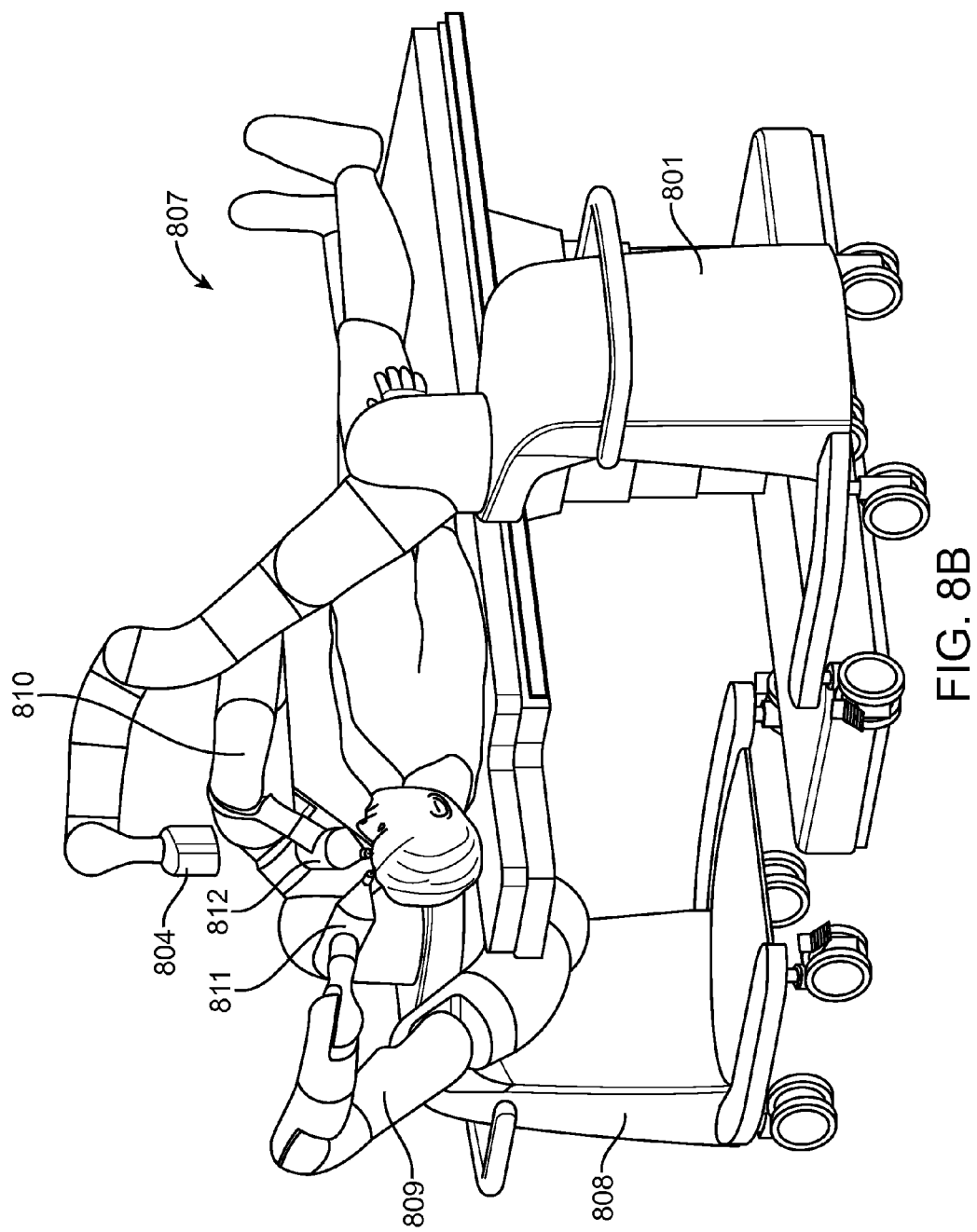
FIG. 8B illustrates a robotic surgery system where subsystem 801 from FIG. 8A may be used in conjunction with another subsystem to perform microsurgery, in accordance with an embodiment of the present invention.

FIG. 8B illustrates an embodiment of the present invention where subsystem 801 from FIG. 8A may be used in conjunction with subsystem 808 to perform microsurgery. Subsystem 808 provides arms 809 and 810, each with microsurgical tools 811 and 812 connected through instrument interfaces on each respective arm. In some embodiments, the one or more arms may pick up and exchange tools at a table or other suitable holding mechanism within reach of the robotic arm, such as a docking station.

In some embodiments, the mechanism changer interface may be a simple screw to secure an associated IDM. In other embodiments, the mechanism changer interface may be a bolt plate with an electrical connector.

6. Instrument Device Manipulator (IDM).

Figure 9A:
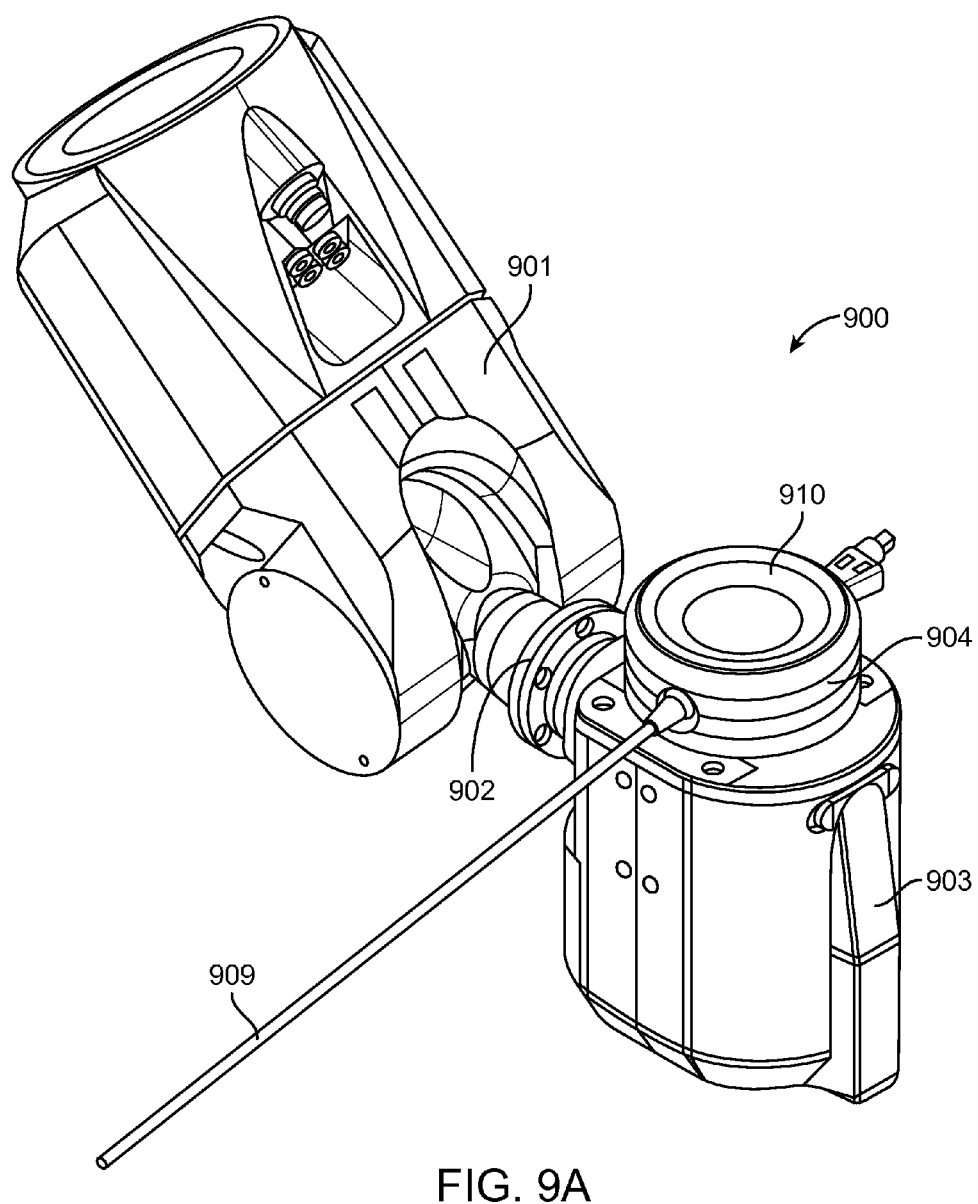
FIG. 9A illustrates a portion of a robotic medical system that includes a manipulator, in accordance with an embodiment of the present invention.

FIG. 9A illustrates a portion of a robotic medical system that includes a manipulator, in accordance with an embodiment of the present invention. System 900 includes a partial view of a robotic arm 901, an articulating interface 902, an instrument device manipulator ("IDM") 903, and an endoscopic tool 904. In some embodiments, the robotic arm 901 may be only a linkage in a larger robotic arm with multiple joints and linkages. The articulating interface 902 couples IDM 903 to robotic arm 901. In addition to coupling, the articulating interface 902 may also transfer pneumatic pressure, power signals, control signals, and feedback signals to and from the arm 901 and the IDM 903.

The IDM 903 drives and controls the endoscopic tool 904. In some embodiments, the IDM 903 uses angular motion transmitted via output shafts in order to control the endoscopic tool 904. As discussed later, the IDM 903 may comprise a gear head, motor, rotary encoder, power circuits, control circuits.

Endoscopic tool 904 may comprise a shaft 909 with a distal tip and proximal end. A tool base 910 for receiving the control signals and drive from IDM 903 may be coupled to the proximal end of the shaft 909. Through the signals received by the tool base 910, the shaft 909 of endoscopic tool 904 may be controlled, manipulated, and directed based on the angular motion transmitted via output shafts 905, 906, 907, and 908 (see FIG. 9B) to the tool base 910 of the endoscopic tool 904.

Figure 9B:
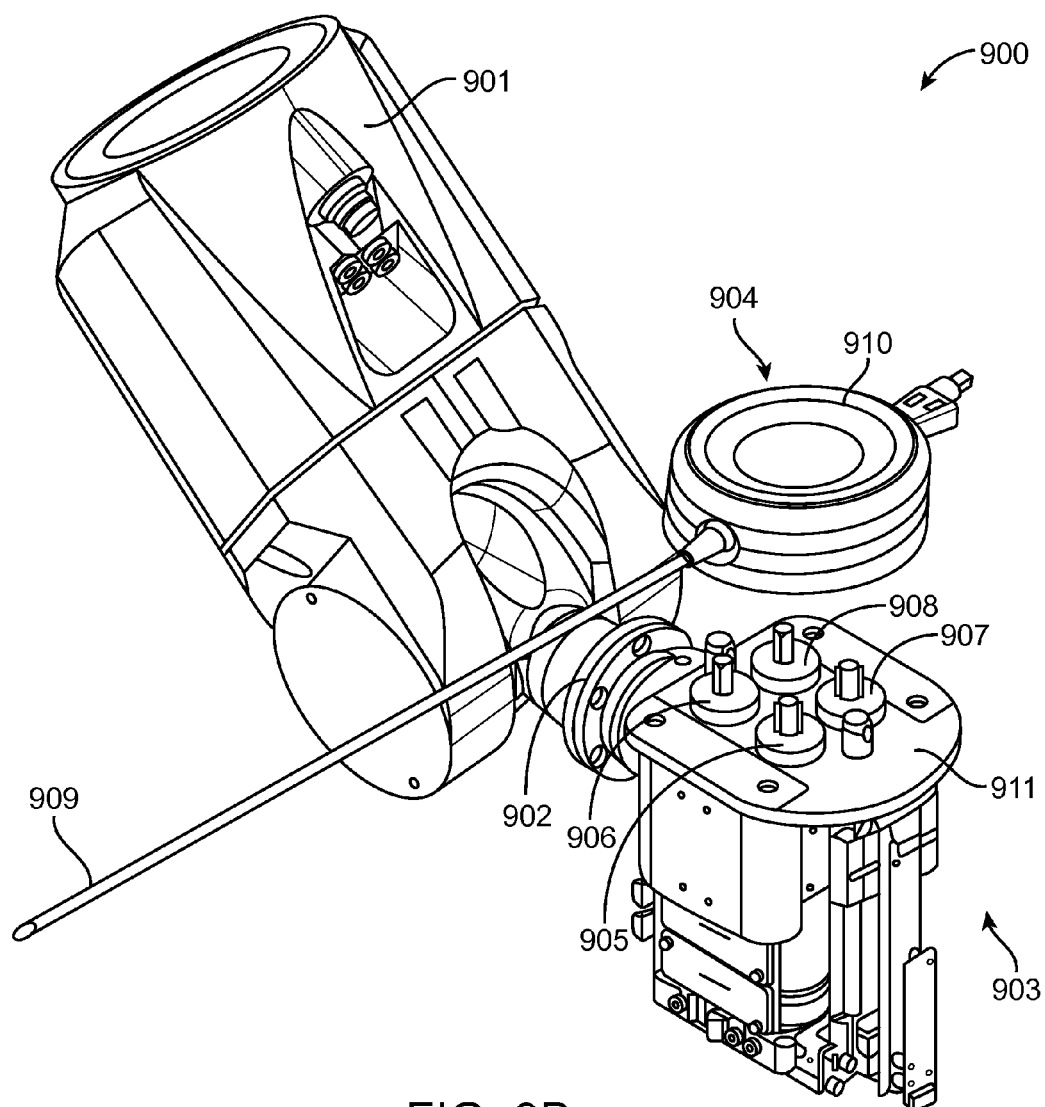
FIG. 9B illustrates an alternative view of the robotic medical system disclosed in FIG. 9A.

FIG. 9B illustrates an alternative view of the robotic medical system disclosed in FIG. 9A. In FIG. 9B, the endoscopic tool 904 has been removed from the IDM 903, to reveal the output shafts 905, 906, 907, and 908. Additionally, removal of the outer skin/shell of IDM 903 reveals the components below the IDM top cover 911.

Figure 10:
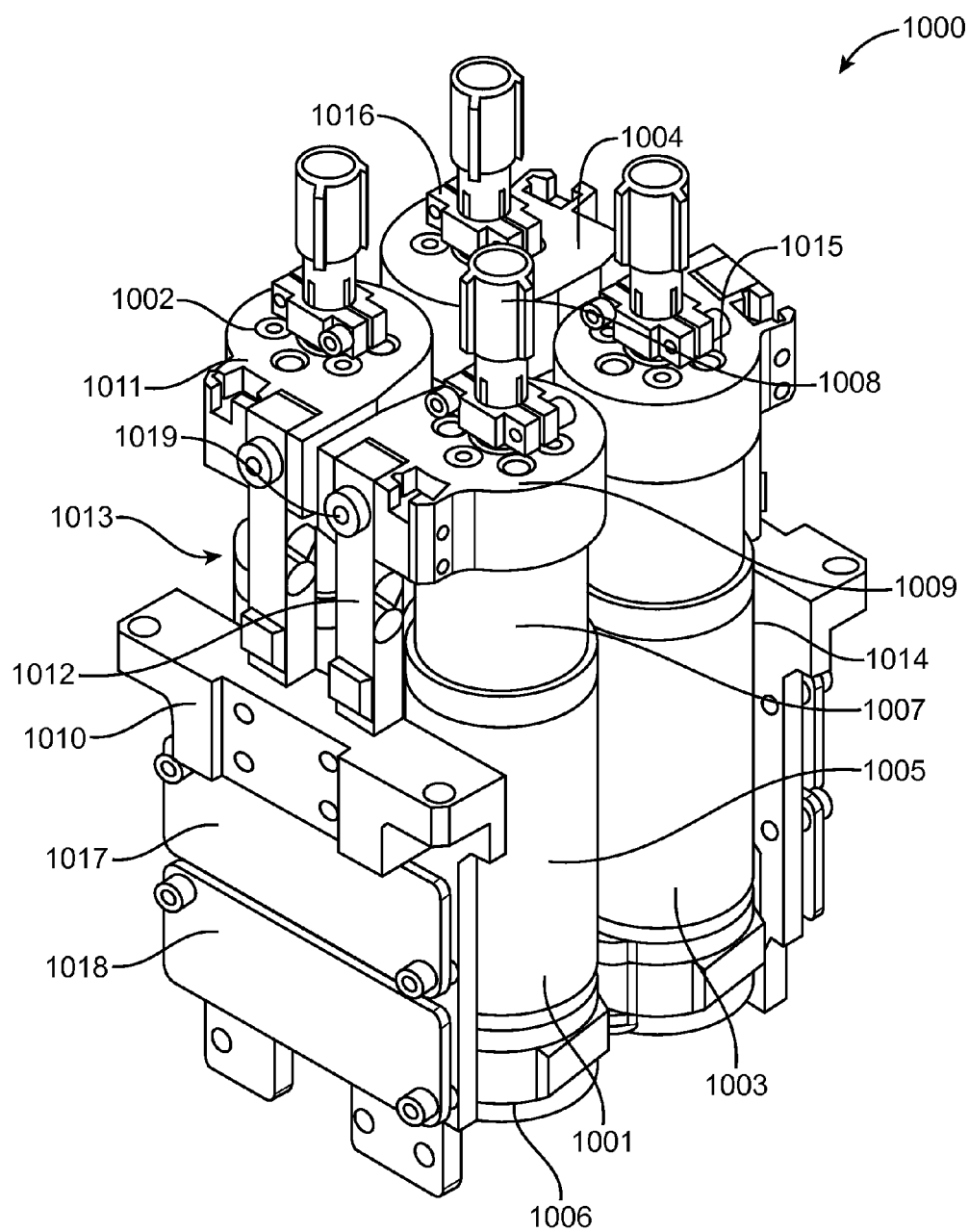
FIG. 10 illustrates an alternative view of the independent drive mechanism from FIGS. 9A, 9B with a tension sensing apparatus in accordance with an embodiment of the present invention.

FIG. 10 illustrates an alternative view of the independent drive mechanism from FIGS. 9A, 9B with a tension sensing apparatus in accordance with an embodiment of the present invention. In cutaway view 1000 of IDM 903, parallel drive units 1001, 1002, 1003, and 1004 are the structurally largest components in the IDM 903. In some embodiments, from the proximal to the distal end, a drive unit 1001 may be comprised of a rotary encoder 1006, a motor 1005, and a gear head 1007. Drive units 1002, 1003, and 1004 may be constructed similarly—comprising of motors, encoders, and gear heads underneath the top cover 911. In some embodiments, the motor used in the drive unit is a brushless motor. In other embodiments, the motor may be a direct current servo motor.

Rotary encoder 1006 monitors and measures the angular speed of the driveshaft of motor 1005. In some embodiments, rotary encoder 1006 may be a redundant rotary encoder. The structure, capabilities, and use of an appropriate redundant encoder is disclosed in U.S. Provisional Patent Application No. 62/037,520, filed Aug. 14, 2014, the entire contents of which are incorporated by reference.

The torque generated by the motor 1005 may be transmitted to gear head 1007 through a shaft coupled to the rotor of motor 1005. In some embodiments, the gear head 1007 may be attached to the motor 1005 in order to increase torque of the motor output, at the cost of the rotational speed. The increased torque generated by gear head 1007 may be transmitted into gear head shaft 1008. Similarly, drive units 1002, 1003, and 1004 transmit their respective torque out through gear head shafts 906, 907, and 908.

Each individual drive unit may be coupled to a motor mount at its distal end and a strain gauge mount towards its proximal end. For example, the distal end of drive unit 1001 may be clamped to motor mount 1009 and strain gauge mount 1010. Similarly, drive unit 1002 may be clamped to motor mount 1011, while also both being clamped to strain gauge mount 1010. In some embodiments, the motor mounts are constructed from aluminum to reduce weight. In some embodiments, the strain gauge mounts may be adhered to a side of the drive unit. In some embodiments, the strain gauge mounts may be constructed from aluminum to reduce weight.

Electrical strain gauges 1012 and 1013 are potted and soldered to the strain gauge mount 1010 and attached using screws to motor mounts 1009 and 1011 respectively. Similarly, a pair of strain gauges (not shown) proximal to drive units 1003 and 1004 are potted and soldered to strain gauge mount 1014 and attached to motor mounts 1015 and 1016 respectively using screws. In some embodiments, the electrical strain gauges may be held in place to their respective motor mount using side screws. For example, side screws 1019 may be inserted into motor mount 1009 to hold in place strain gauge 1012. In some embodiments, the gauge wiring in the electrical strain gauges may be vertically arranged in order to detect any vertical strain or flex in the drive unit which may be measured as horizontal displacement by the motor mount (1009, 1011) relative to the strain gauge mount (1010).

The strain gauge wiring may be routed to circuits on the strain gauge mounts. For example, strain gauge 1012 may be routed to circuit board 1017 which may be mounted on strain gauge mount 1010. Similarly, strain gauge 1013 may be routed to circuit board 1018 which may be also mounted on strain gauge mount 1010. In some embodiments, circuit boards 1017 and 1018 may process or amplify the signals from strain gauges 1012 and 1013 respectively. The close proximity of circuit boards 1017 and 1018 to strain gauges 1012 and 1013 helps to reduce the signal to noise ratio in order to obtain more accurate readings.

Figure 11A:
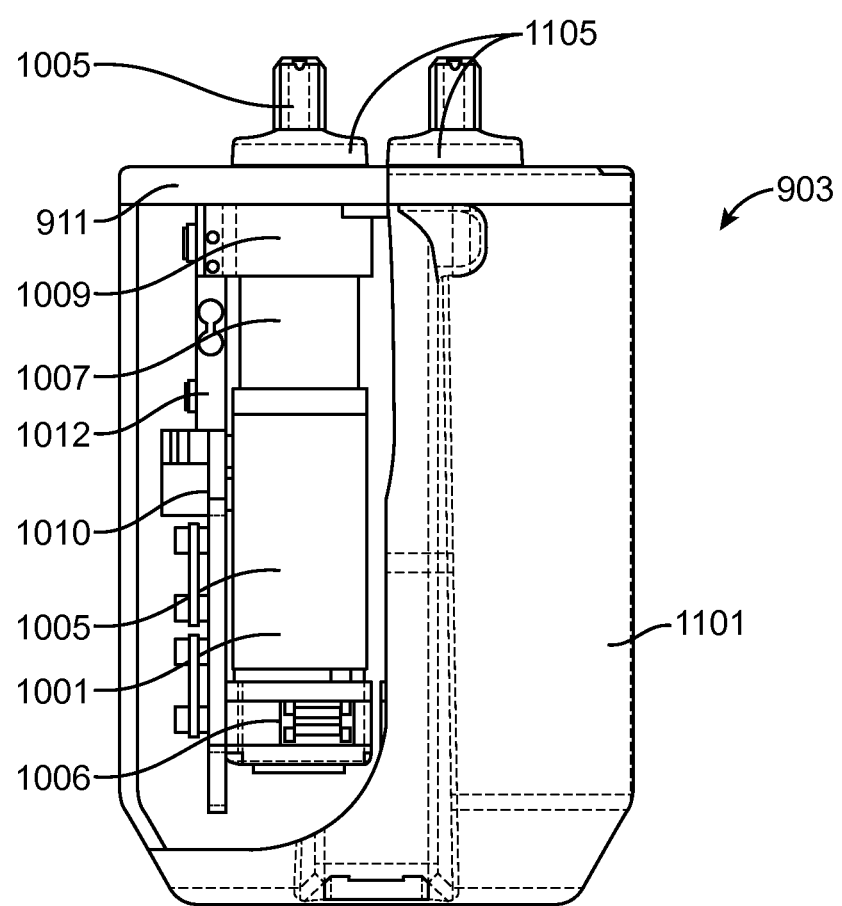
FIG. 11A illustrates a cutaway view of the independent drive mechanism from FIGS. 9A, 9B, and 10 from an alternate angle.

FIG. 11A illustrates a cutaway view of the independent drive mechanism from FIGS. 9A, 9B, and 10 from an alternate angle. As shown in FIG. 11A, a portion of outer shell/skin 1101 has been cut away to reveal the innards of IDM 903. As discussed earlier, the drive unit 1001 comprises of motor 1005, rotary encoder 1006, and gear head 1007. The drive unit 1001 may be coupled to the motor mount 1009 and passes through the top cover 911 through which the output shaft 905 may be driven at the desired angular speed and torque. The motor mount 1009 may be coupled to a vertically aligned strain gauge 1012 using side screws. In addition to coupling to motor mount 1009, the stain gauge 1012 may be potted into the strain gauge mount 1010. In some embodiments, the output shaft 905 includes a labyrinth seal over a gear head shaft.

Figure 11B:
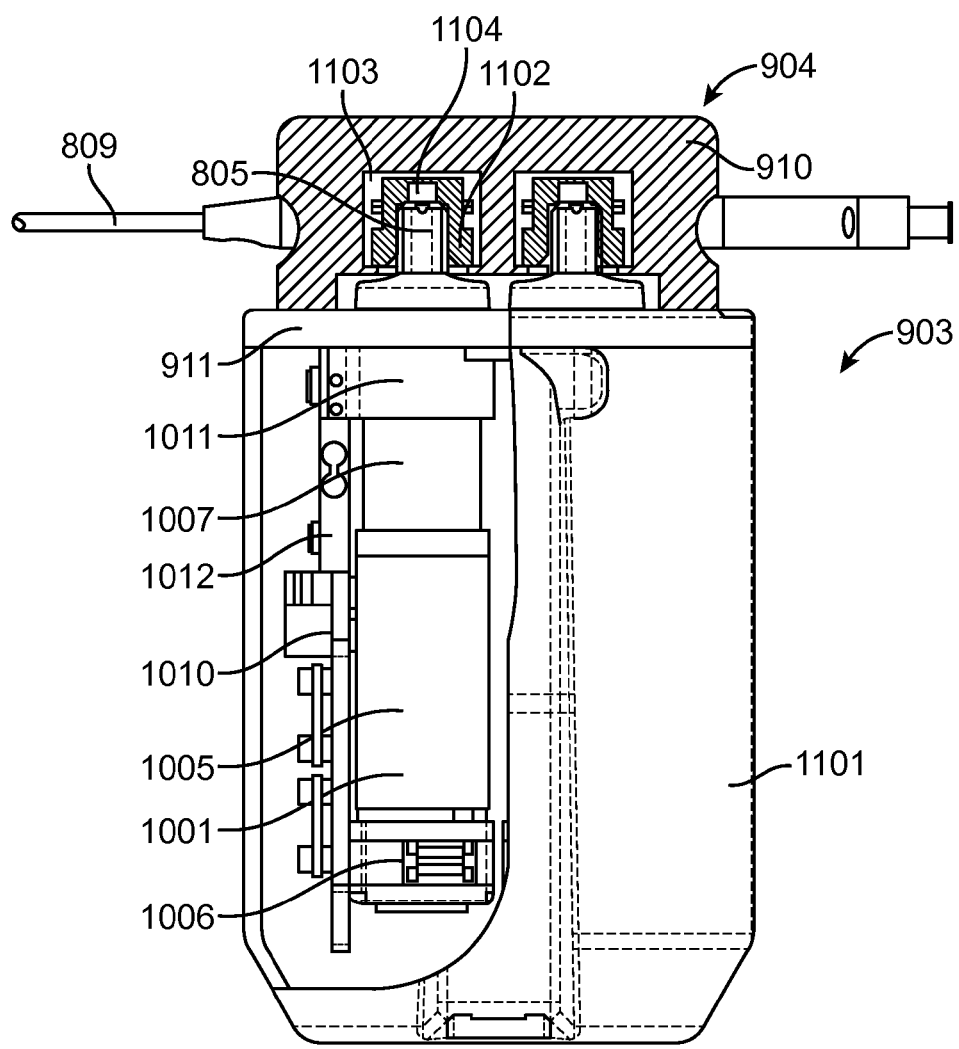
FIG. 11B illustrates a cutaway view of the previously discussed independent drive mechanism in combination with an endoscopic tool, in accordance with an embodiment of the present invention.

FIG. 11B illustrates a cutaway view of the previously discussed independent drive mechanism in combination with an endoscopic tool, in accordance with an embodiment of the present invention. As shown in FIG. 11B, endoscopic tool 904, mounted on IDM 903, contains pulleys that are longitudinally aligned with the output shafts of the IDM 903, such as pulley 1102 which may be concentric with output shaft 905. Pulley 1102 may be housed inside of a precision cut chamber 1103 within tool base 910 such that the pulley 1102 may be not rigidly fixed inside chamber 1103 but rather "floats" within the space in the chamber 1103.

The splines of the pulley 1102 are designed such that they align and lock with splines on output shaft 905. In some embodiments, the splines are designed such that there may be only a single orientation for the endoscopic tool to be aligned with IDM 903. While the splines ensure pulley 1102 is concentrically aligned with output shaft 905, pulley 1102 may also incorporate use of a magnet 1104 to position and axially hold the floating pulley 1102 in alignment with output shaft 905. Locked into alignment, rotation of the output shaft 905 and pulley 1102 tensions the pull wires within endoscopic tool 904, resulting in articulation of shaft 909.

Figure 12:
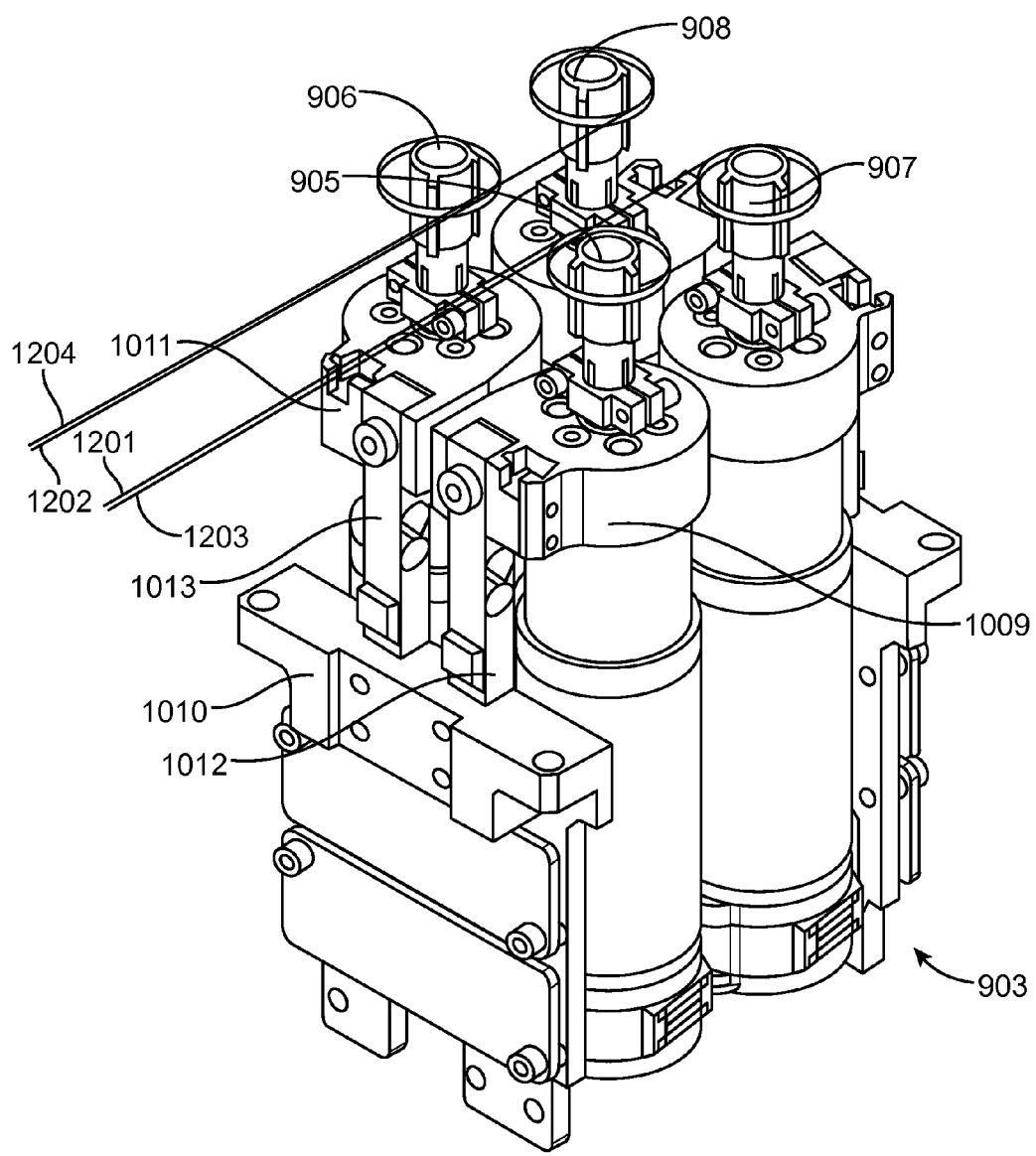
FIG. 12 illustrates an alternative view of the previously-discussed independent drive mechanism with pull wires from an endoscopic tool in accordance with an embodiment of the present invention.

FIG. 12 illustrates an alternative view of the previously-discussed independent drive mechanism with pull wires from an endoscopic tool in accordance with an embodiment of the present invention. In some embodiments, the endoscopic tool may use pull wires in order to articulate and control the shaft. In those embodiments, these pull wires 1201, 1202, 1203, and 1204 may be tensioned or loosened by the output shafts 905, 906, 907, and 908 respectively of the IDM 903. Accordingly, the pull wires may be robotically controlled via the control circuitry in IDM 903.

Just as the output shafts 905, 906, 907, and 908 transfer force down pull wires 1201, 1202, 1203, and 1204 through angular motion, the pull wires 1201, 1202, 1203, and 1204 transfer force back to the output shafts and thus to the motor mounts and drive units. For example, tension in the pull wires directed away from the output shaft results in forces pulling the motor mounts 1009 and 1011. This force may be measured by the strain gauges, such as 1012 and 1013, since the strain gauges are both coupled to motor mounts 1009 and 1011 and potted in the strain gauge mount 1010.

Figure 13:
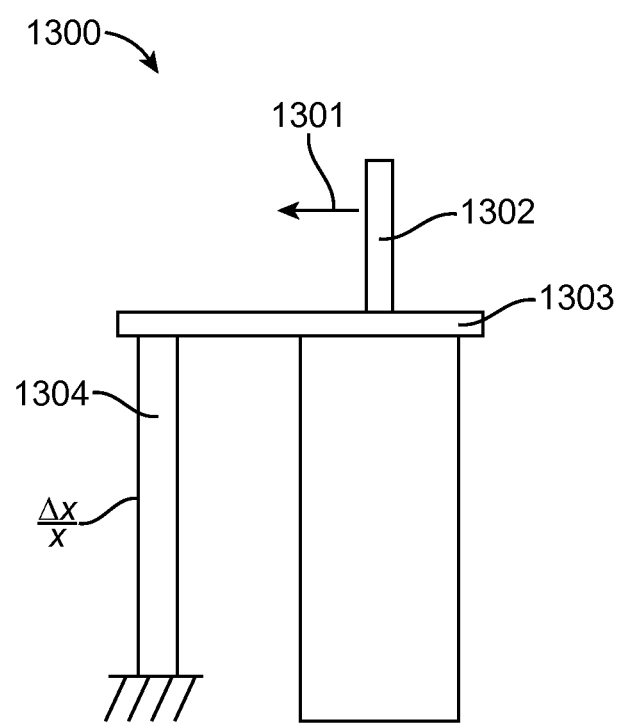
FIG. 13 illustrates a conceptual diagram that shows how horizontal forces may be measured by a strain gauge oriented perpendicular to the forces, in accordance with an embodiment of the invention.

FIG. 13 illustrates a conceptual diagram that shows how horizontal forces may be measured by a strain gauge oriented perpendicular to the forces, in accordance with an embodiment of the invention. As shown in diagram 1300, a force 1301 may directed away from the output shaft 1302. As the output shaft 1302 is coupled to the motor mount 1303, the force 1301 results in horizontal displacement of the motor mount 1303. The strain gauge 1304, coupled to both the motor mount 1303 and ground 1305, may thus experience strain as the motor mount 1303 causes the strain gauge 1304 to flex (causing strain) in the direction of the force 1301. The amount of strain may be measured as a ratio of the horizontal displacement of the tip of strain gauge 1304 to the overall horizontal width of the strain gauge 1304.

Accordingly, the strain gauge 1304 may ultimately measure the force 1301 exerted on the output shaft 1302.

In some embodiments, the assembly may incorporate a device to measure the orientation of instrument device manipulator 903, such as an inclinometer or accelerometer. In combination with the strain gauges, measurements from the device may be used to calibrate readings from the strain gauges, since strain gauges may be sensitive to gravitational load effects resulting from their orientation relative to ground. For example, if instrument device manipulator 903 is oriented on its side, the weight of the drive unit may create strain on the motor mount which may be transmitted to the strain gauge, even though the strain may not result from strain on the output shafts.

In some embodiments, the output signals from the strain gauge circuit boards may be coupled to another circuit board for processing control signals. In some embodiments, power signals are routed to the drive units on another circuit board from that of processing control signals.

As discussed earlier, the motors in drive units 1001, 1002, 1003, and 1004 ultimately drive output shafts, such as output shafts 905, 906, 907, and 908. In some embodiments, the output shafts may be augmented using a sterile barrier to prevent fluid ingress into the instrument device manipulator 903. In some embodiments, the barrier may make use of a labyrinth seal (1105 from FIG. 11A) around the output shafts to prevent fluid ingress. In some embodiments, the distal end of the gear head shafts may be covered with output shafts in order to transmit torque to a tool. In some embodiments, the output shafts may be clad in a steel cap to reduce magnetic conductance. In some embodiments, the output shafts may be clamped to the gear head shafts to assist transfer of torque.

Instrument device mechanism 903 may also be covered in a shell or skin, such as outer shell/skin 1101. In addition to being aesthetically pleasing, the shell provides fluid ingress protection during operation, such as during medical procedures. In some embodiments, the shell may be constructed using cast urethane for electromagnetic shielding, electromagnetic compatibility, and electrostatic discharge protection.

In an embodiment of the present invention, each of those output shafts in individually tension may pull wires in an endoscopic tool that makes use of steerable catheter technology. Tensile force in the pull wires may be transmitted to the output shafts 905, 906, 907 and 908 and down to a motor mount, such as motor mounts 1009 and 1011.

7. Endoscopic Tool Design.

Figure 14:
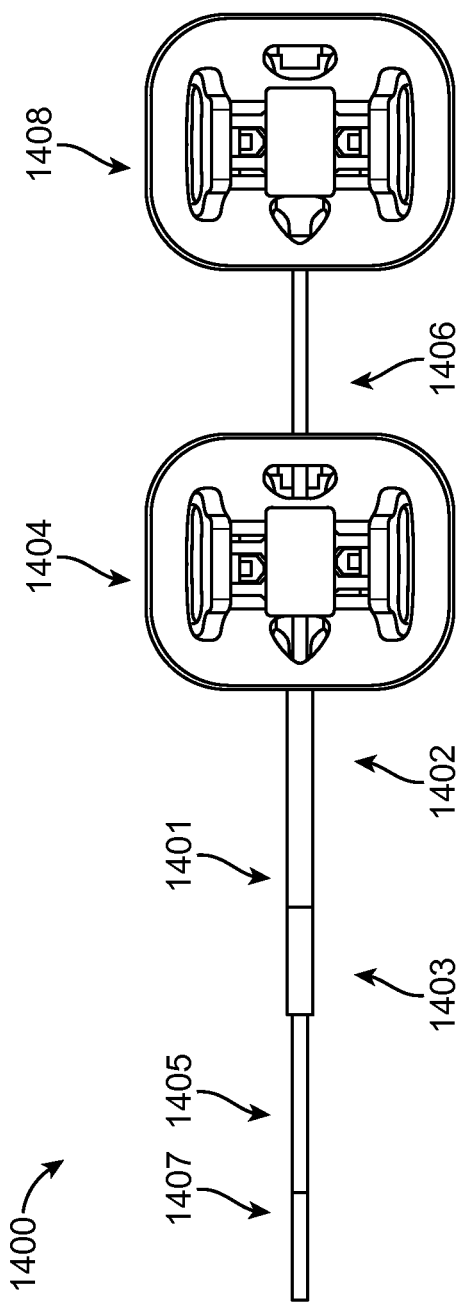
FIG. 14 is an illustration of an endoscopic tool that may be used in conjunction with a robotic system 100 from FIG. 1, in accordance with an embodiment of the present invention.

In a preferred embodiment, robotic system 100 from FIG. 1 may drive a tool customized for endolumenal procedures, such as endoscopic tool 118. FIG. 14 is an illustration of an endoscopic tool that may be used in conjunction with a robotic system 100 from FIG. 1, in accordance with an embodiment of the present invention. Endoscopic tool 1400 may be arranged around nested longitudinally-aligned tubular bodies, referred to as a "sheath" and a "leader". The sheath 1401, the tubular tool with the larger outer diameter, may be comprised of a proximal sheath section 1402, a distal sheath section 1403, and a central sheath lumen (not shown). Through signals received in the sheath base 1404, the distal sheath portion 1403 may be articulated in the operator's desired direction. Nested within the sheath 1401 may be a leader 1405 with a smaller outer diameter. The leader 1405 may comprise a proximal leader section 1406 and a distal leader section 1407, and a central working channel. Similar to sheath base 1404, leader base 1408 controls articulation of the distal leader section 1407 based on control signals communicated to leader base 1408, often from the IDMs (e.g., 903 from FIG. 9A).

Both the sheath base 1404 and leader base 1408 may have similar drive mechanisms, to which control tendons within sheath 1401 and leader 1405 are anchored. For example, manipulation of the sheath base 1404 may place tensile loads on tendons in the sheath 1401, therein causing deflection of distal sheath section 1403 in a controlled manner. Similarly, manipulation of the leader base 1408 may place tensile loads on the tendons in leader 1405 to cause deflection of distal leader section 1407. Both the sheath base 1404 and leader base 1408 may also contains couplings for the routing of pneumatic pressure, electrical power, electrical signals or optical signals from the IDMs to the sheath 1401 and leader 1404.

Control tendons within the sheath 1401 and leader 1405 may be routed through the articulation section to an anchor positioned distal to the articulation section. In a preferred embodiment, the tendons within sheath 1401 and leader 1405 may consist of a stainless steel control tendon routed through a stainless steel coil, such as a coil pipe. One skilled in the arts would appreciate that other materials may be used for the tendons, such as Kevlar, Tungsten and Carbon Fiber. Placing loads on these tendons causes the distal sections of sheath 1401 and leader 1405 to deflect in a controllable manner. The inclusion of coil pipes along the length of the tendons within the sheath 1401 and leader 1405 may transfer the axial compression back to the origin of the load.

Using a plurality of tendons, the endoscopic tool 1400 has the ability to navigate lumens within the human body with ease by providing a plurality of degrees of freedom (each corresponding to an individual tendon) control at two points—distal sheath section 1403 and distal leader section 1407—along its length. In some embodiments, up to four tendons may be used in either the sheath 1401 and/or leader 1405, providing up to eight degrees of freedom combined. In other embodiments, up to three tendons may be used, providing up to six degrees of freedom.

In some embodiments, the sheath 1401 and leader 1405 may be rolled 360 degrees, providing for even more tool flexibility. The combination of roll angles, multiple degrees of articulation, and multiple articulation points provides the surgeon with a significant improvement to the instinctive control of the device as it navigates a tortuous path within the human body.

Figure 15A:
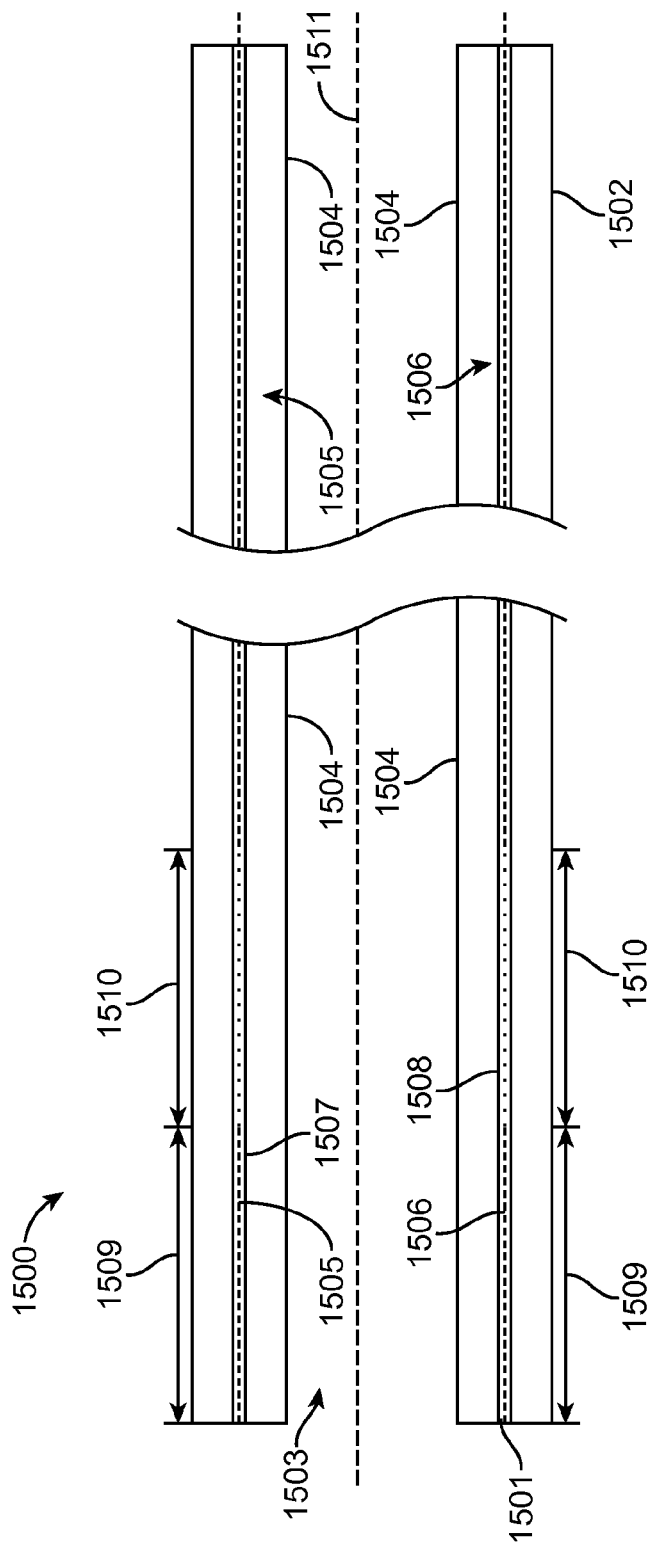
FIGS. 15A, 15B, 15C, 16A, and 16B generally illustrate aspects of a robotically-driven endoscopic tool, in accordance with an embodiment of the present invention.

FIGS. 15A, 15B, 15C, 16A, and 16B generally illustrate aspects of a robotically-driven endoscopic tool, such a sheath 210 and leader 212 from FIG. 2, in accordance with an embodiment of the present invention. FIG. 15A illustrates an endoscopic tool with sheath 1500 having distal end 1501 and proximal end 1502 and lumen 1503 running between the two ends. Lumen 1503 may be sized to slidingly receive a flexible endoscope (such as leader 1600 from FIG. 16). Sheath 1500 has walls 1504 with tendons 1505 and 1506 running inside the length of walls 1504 of sheath 1500. Tendons 1505 and 1506 may slidingly pass through conduits 1507 and 1508 in walls 1504 and terminate at distal end 1501. In some embodiments, the tendons may be formed from steel. Appropriate tensioning of tendon 1505 may compress distal end 1501 towards conduit 1507, while minimizing bending of the helixed section 1510. Similarly, appropriate tensioning of tendon 1506 may compress distal end 1501 towards conduit 1508. In some embodiments, lumen 1503 may not be concentric with sheath 1500.

Tendons 1505 and 1506 and associated conduits 1507 and 1508 from sheath 1500 from FIG. 15A preferably do not run straight down the entire length of sheath 1500, but helix around sheath 1500 along helixed section 1510 and then run longitudinally straight (i.e., approximately parallel to the neutral axis) along distal section 1509. It will be appreciated that helixed section 1510 may begin from the proximal end of distal section 1509 extending proximally down sheath 1510 and may terminate at any desired length for any desired or variable pitch. The length and pitch of helixed section 1510 may be determined based on the desired properties of sheath 1500, taking into account desired flexibility of the shaft, and increased friction in the helixed section 1510. Tendons 1505 and 1506 may run approximately parallel to central axis 1511 of sheath 1500 when not in the helixed section, such as the proximal and distal sections of the endoscope 1500.

In some embodiments, the tendon conduits may be at ninety degrees to each other (e.g., 3-, 6-, 9- and 12-o'clock). In some embodiments, the tendons may be spaced one hundred and twenty degrees from each other, e.g., three total tendons. In some embodiments, the tendons may be not be equally spaced. In some embodiments, they may be to one side of the central lumen. In some embodiments, the tendon count may differ from three or four.

Figure 15B:
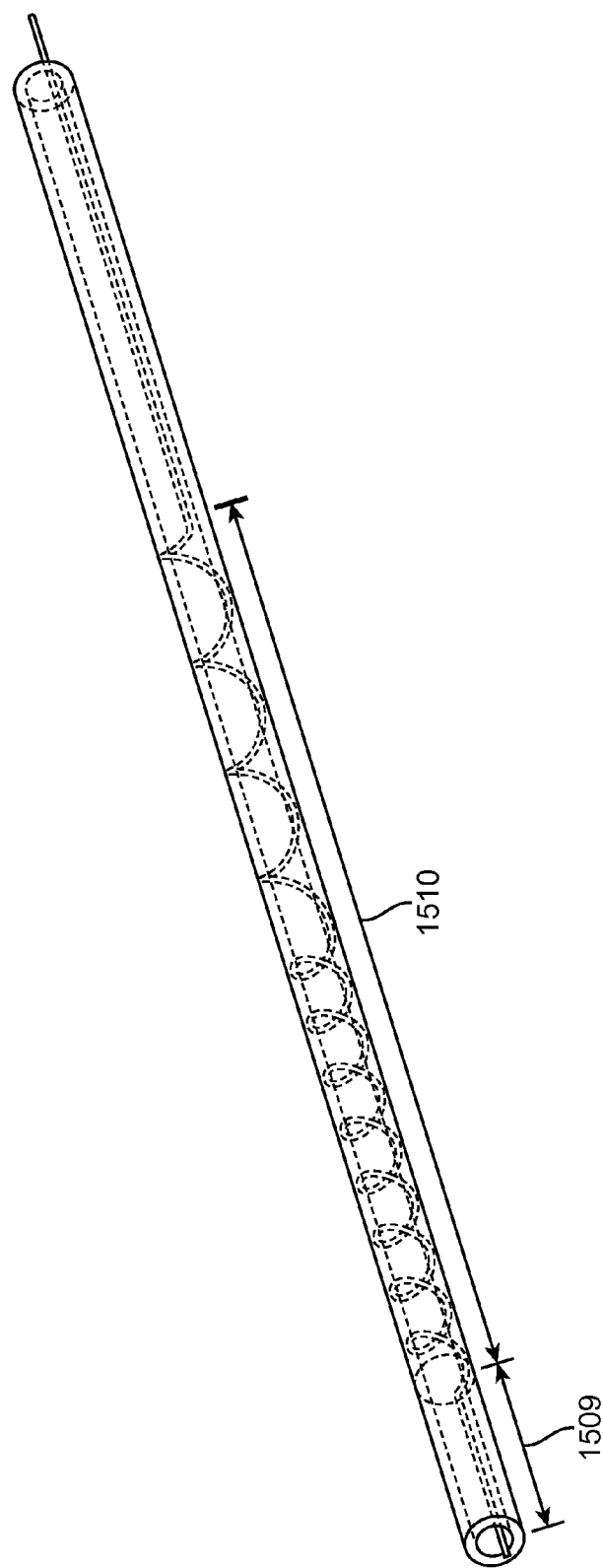
Figure 15C:
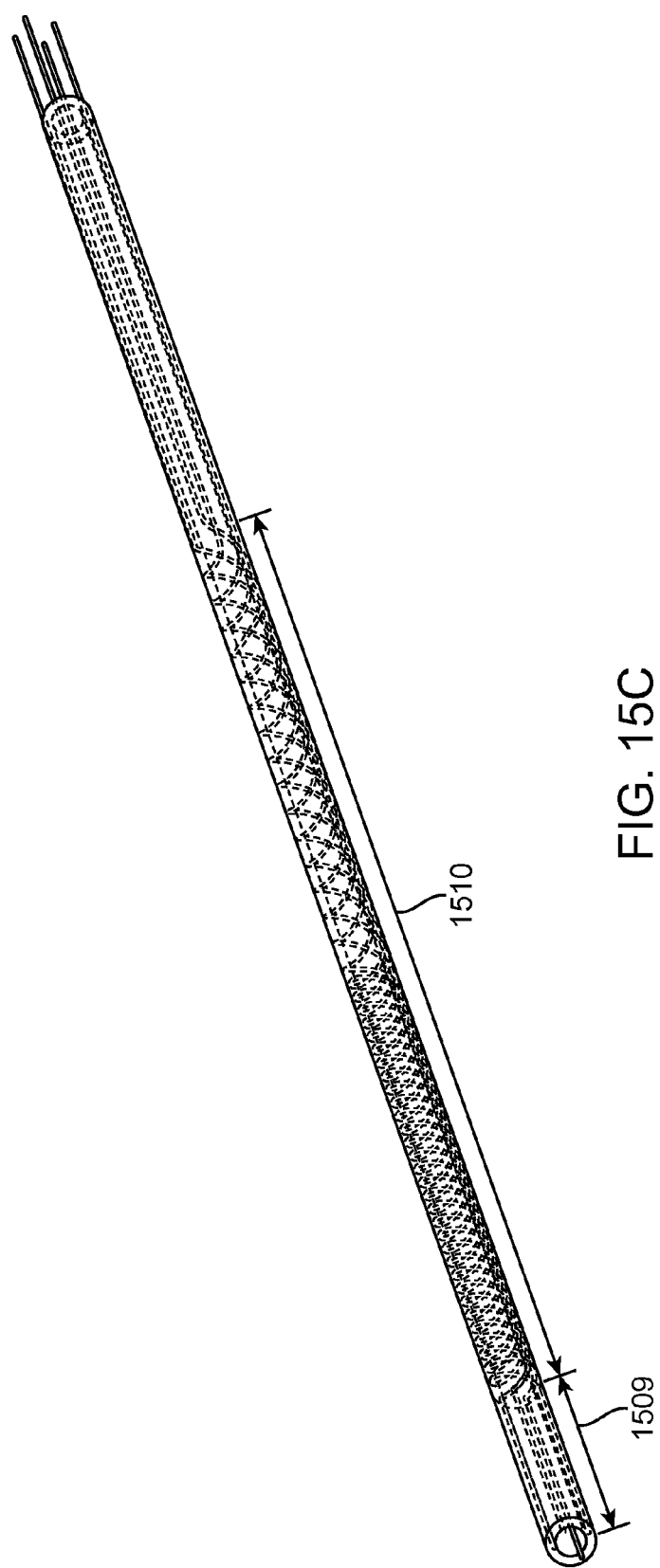

FIG. 15B shows a three-dimensional illustration of an embodiment of sheath 1500 with only one tendon for the purpose of clarifying the distinction between non-helixed section 1509 and a variable pitch helixed section 1510. While one tendon may be used, it may be preferable to use multiple tendons. FIG. 15C shows a three-dimensional illustration of an embodiment of sheath 1500 with four tendons extending along distal section 1509, variable pitch helixed section 1510.

Figure 16A:
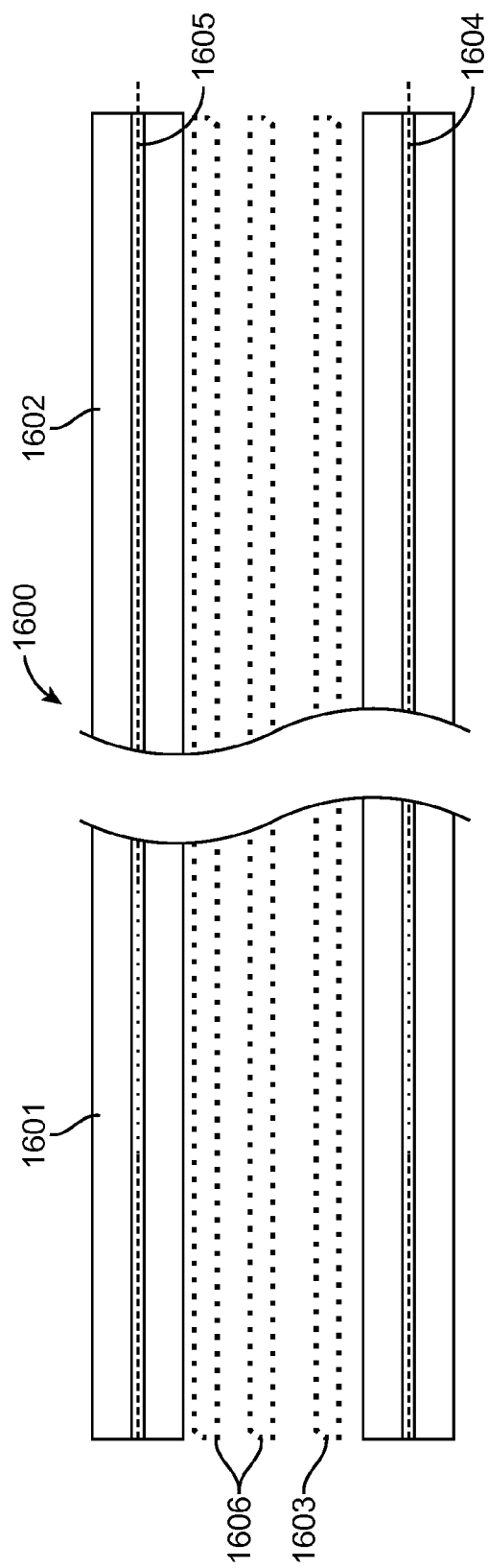

FIG. 16A illustrates an endoscopic leader 1600 with distal end 1601 and proximal end 1602, that may be sized to slidingly reside within the sheath 1500 from FIG. 15. Leader 1600 may include at least one working channel 1603 passing through it. Proximal end 1502 of sheath 1500 and proximal end 1602 of leader 1600 are, respectively, operatively connected to tool bases 206 and 208 from FIG. 2 respectively. Tendons 1604 and 1605 slidingly pass through conduits 1606 and 1607 respectively in walls 1608 and terminate at distal end 1601.

Figure 16B:
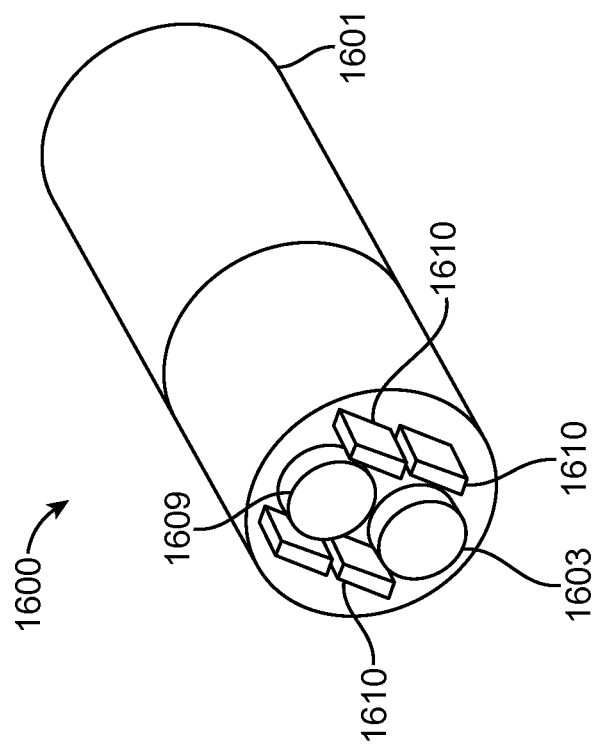

FIG. 16B illustrates the distal end 1601 of leader 1600, an exemplary embodiment, that has imaging 1609 (e.g., CCD or CMOS camera, terminal end of imaging fiber bundle etc.), light sources 1610 (e.g., LED, optic fiber etc.) and may include at least one working channel opening 1603. Other channels or operating electronics 1606 may be provided along leader 1600 to provide various known capabilities at the distal end, such as wiring to camera, insufflation, suction, electricity, fiber optics, ultrasound transducer, EM sensing, and OCT sensing.

In some embodiments, the distal end 1601 of leader 1600 may include a "pocket" for insertion of a tool, such as those disclosed above. In some embodiments, the pocket may include an interface for control over the tool. In some embodiments, a cable, such as an electrical or optical cable, may be present in order communicate with the interface.

In some embodiments, both sheath 1500 from FIG. 15A and leader 1600 from FIG. 16A may have robotically-controlled steerable distal ends. The structure of sheath 1500 and leader 1600 enabling this control may be substantially the same. Thus, discussion for the construction of sheath 1500 will be limited to that of the sheath 1500 with the understanding that the same principles apply to the structure of the leader 1600.

Therefore, tendons 1604 and 1605 and associated conduits 1606 and 1607 from the leader 1600 from FIG. 16A do not run longitudinally straight (i.e., approximately parallel to the neutral axis) down the length of leader 1600, but helix along different portions of leader 1600. As with the helixed tendons and conduits in sheath 1500, the helixed sections of leader 1600 may be determined based on the desired properties of the leader, taking into account desired flexibility of the shaft, and increased friction in the helixed section. Tendons 1604 and 1605 run approximately parallel to central axis of leader 1600 when not in the helixed section.

The helixed section, as described more fully below, may help isolate the bending to the distal section, while minimizing any bending that occurs along the shaft proximal to the distal section. In some embodiments of the present invention, the helix pitch of the conduits in sheath 1500 and leader 1600 may be varied along the length of the helixed section, which, as more fully described below will alter the stiffness/rigidity of the shaft.

The use of helixed conduits and helixed tendons in sheath 1500 and leader 1600 present significant advantages over previous flexible instruments without helixed conduits, particularly when navigating non-linear pathways in anatomical structures. When navigating curved pathways, it may be preferable for sheath 1500 and leader 1600 to remain flexible over most of the lengths thereof, and to have a controllably steerable distal end section, while also minimal secondary bending of the instrument proximal to the distal bending section. In previous flexible instruments, tensioning the tendons in order to articulate the distal end resulted in unwanted bending and torqueing along the entire length of the flexible instrument, which may be referred to as "muscling" and "curve alignment" respectively.

Figure 17A:
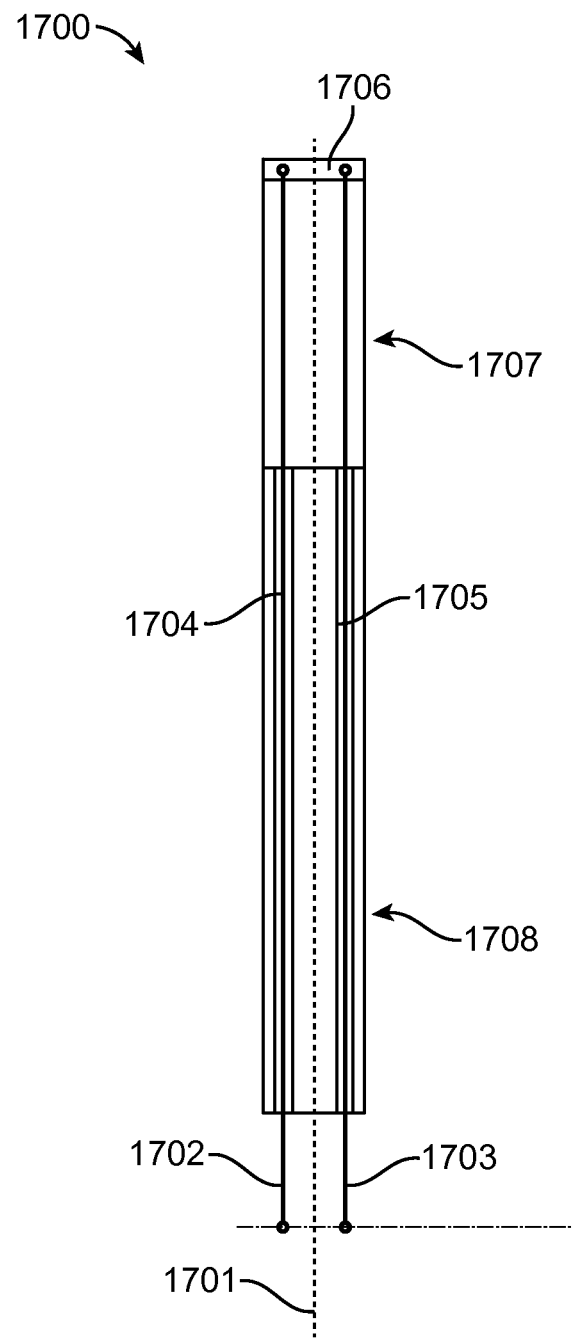
FIGS. 17A to 17D illustrates how prior art flexible instruments exhibit undesirable "muscling" phenomenon when tendons are pulled.

FIGS. 17A to 17D illustrates how prior art flexible instruments exhibit undesirable "muscling" phenomenon when tendons are pulled. In FIG. 17A, a previous endoscope 1700 may have four tendons or control wires along the length of the endoscope 1700 that run approximately parallel to the neutral axis 1701. Only tendons 1702 and 1703 are shown in cross section traveling through conduits 1704 and 1705 (also known as control lumens) in the shaft wall, each of which are fixedly connected to a control ring 1706 on the distal end of the endoscope 1700. Endoscope 1700 may be intentionally designed to have a bending section 1707 and shaft 1708. In some flexible instruments, the shaft 1708 may incorporate stiffer materials, such as stiffeners.

Figure 17B:
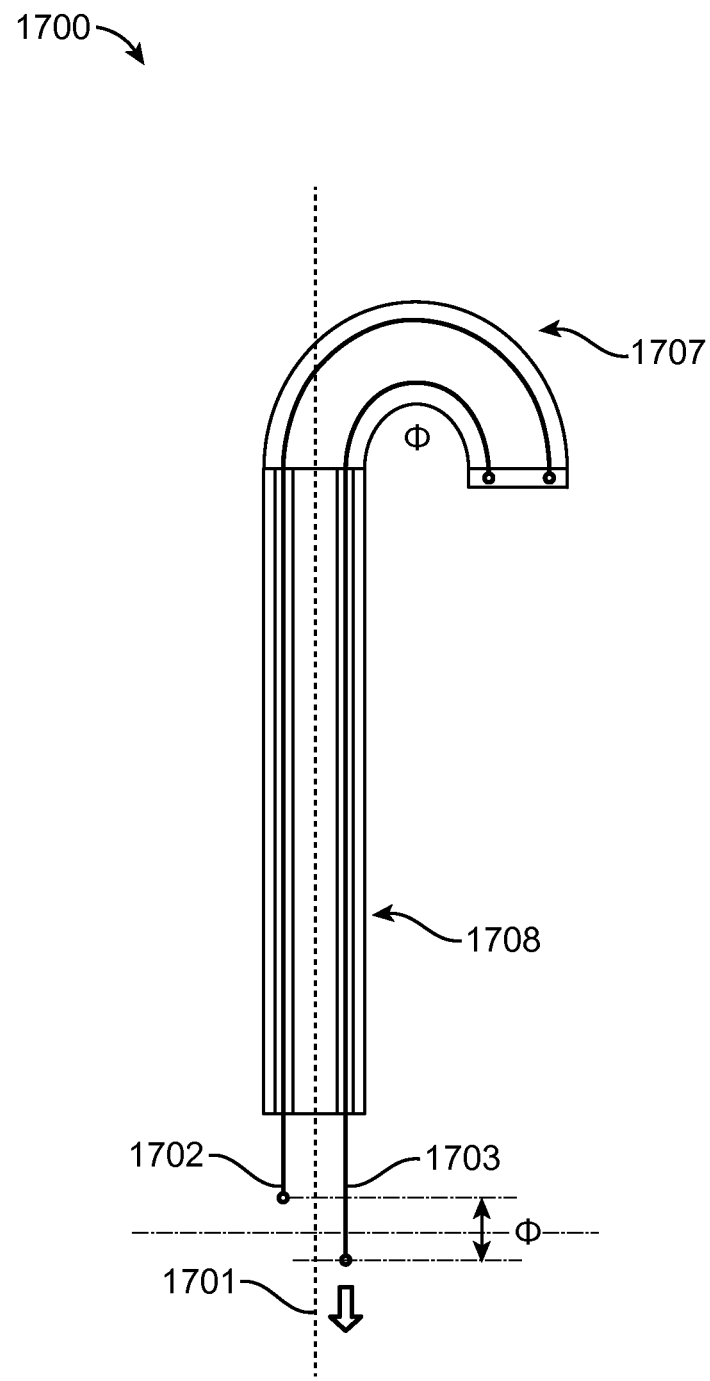

FIG. 17B illustrates an idealized articulation of bending section 1707. By pulling or exerting tension on tendon 1703, articulation of only the distal bending section 1707 results in an amount represented by $\phi$, where the length difference at the proximal ends of tendons 1702 and 1703 would be a $f(\phi)$. In contrast, the shaft 1708 would remain straight along the neutral axis 1701. This may be achieved by having a proximal region 1708 of a significantly higher stiffness than the distal region of 1707.

Figure 17C:
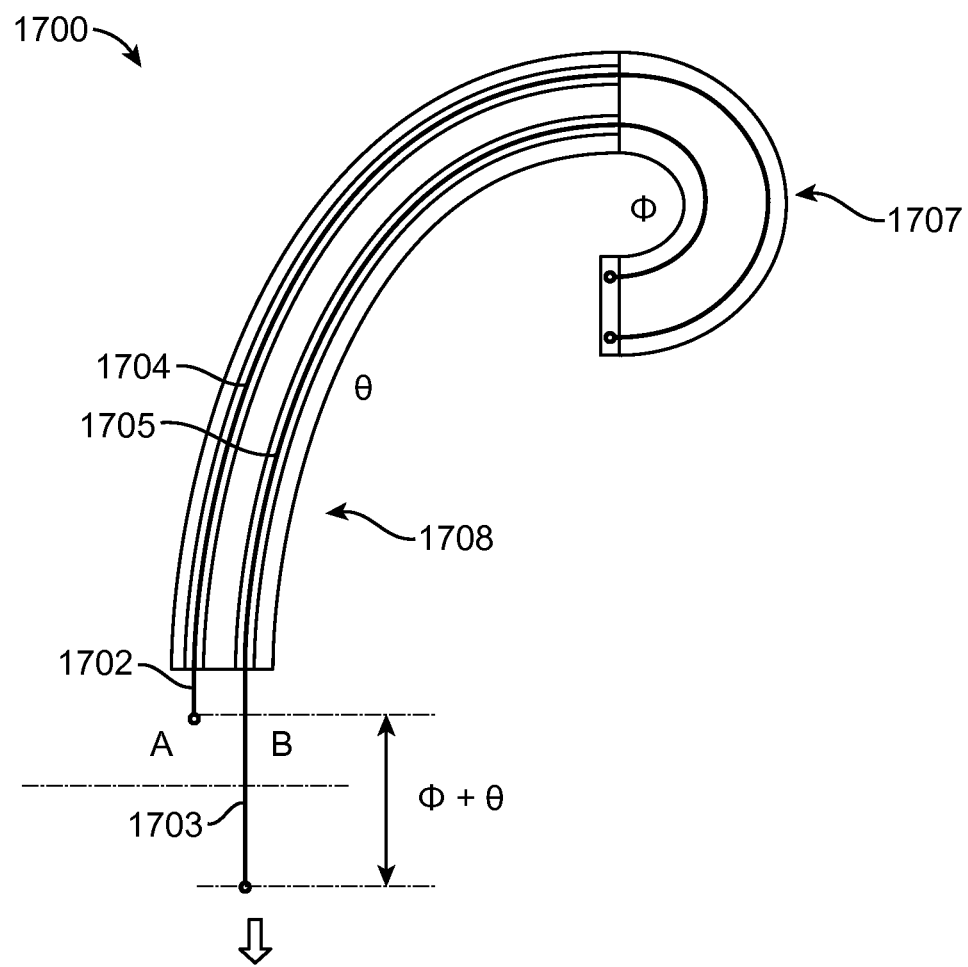

FIG. 17C illustrates the real world result from tensioning tendon 1703. As shown in FIG. 17C, pulling tendon 1703 results in compressive forces along the entire length of the shaft as the tension is non-localized. In an idealized situation, were tendon 1703 along the neutral axis 1701, the entire compressive load would transmit equally down the central axis and most or all bending would occur at the bending section 1707. However, where the tendon 1703 runs along the periphery of the shaft 1708, such as in endoscope 1700, the axial load is transferred off the neutral axis 1701 in the same radial orientation of the neutral axis which creates a cumulative moment along the neutral axis. This causes the shaft 1708 to bend (depicted as θ), where the bend in the shaft 1708 will be in the same direction as the bend in the bending section 1707. The length along conduit 1704 and conduit 1705 must change as the endoscope 1700 and distal bend section 1707 bend. The amount tendons 1702 and 1703 extend from the proximal end is f(φ,θ), as tendon 1703 will need to shorten and tendon 1702 will need to lengthen. This phenomenon, where the shaft 1707 and distal bending section 1708 bend from pulling tendon 1703, is referred to as "muscling."

Figure 17D:
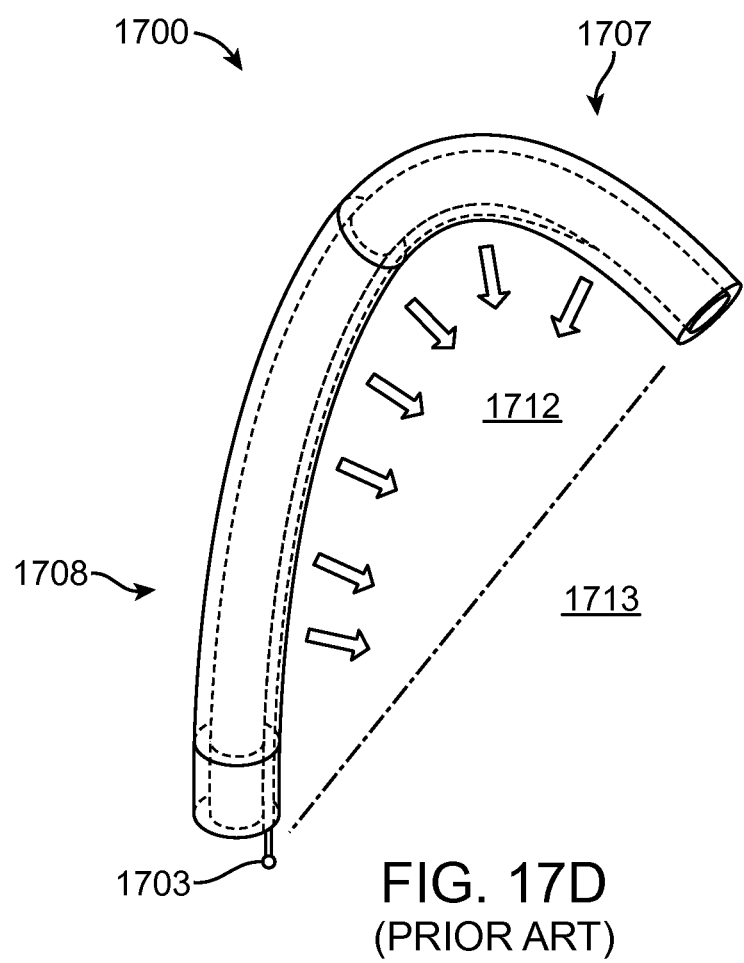

FIG. 17D illustrates the forces that contribute to muscling in three-dimensions. As shown by FIG. 17D, tensioning tendon 1703 along endoscope 1700 causes the tendon 1703 to directionally exert forces 1712 towards one side of the instrument. The direction of forces 1712 reflect that the tension in tendon 1703 causes the tendon to seek to follow a straight line from the tip of the distal bending section 1707 to the base of the shaft 1708, i.e., the lowest energy state as represented by the dotted line 1713. As will be appreciated, if the shaft 1708 is rigid (i.e., not susceptible to bending under the applicable forces), only the distal bending section 1707 will bend. However, in many applications it is not desirable to make the shaft rigidity sufficiently different from the distal end to adequately minimize the muscling phenomenon.

Figure 17E:
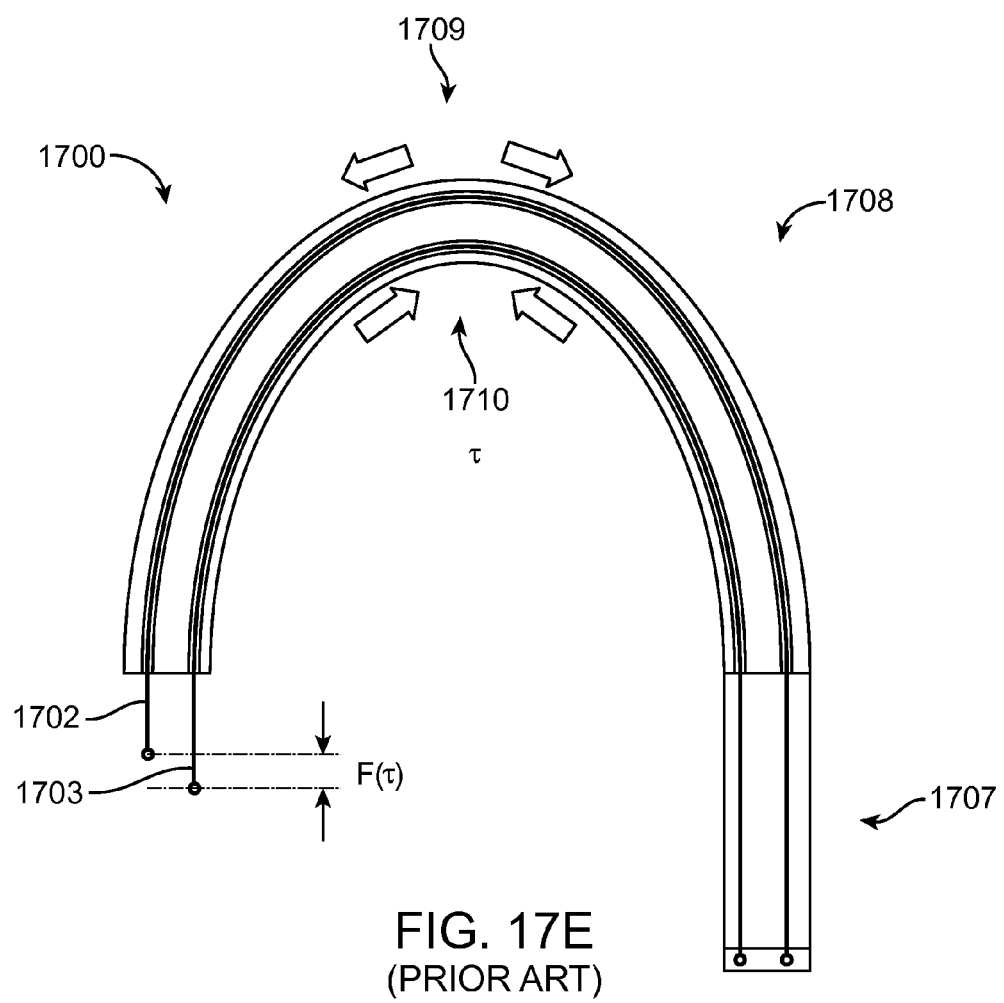
FIGS. 17E to 17H illustrate how prior art flexible instruments suffer from curve alignment phenomenon during use in non-linear pathways.

FIGS. 17E to 17H illustrate how previous flexible instruments suffer from curve alignment phenomenon during use in non-linear pathways. FIG. 17E shows a previous flexible endoscope 1700 at rest within a non-linear path, represented by having a bend τ along the shaft 1708 of endoscope 1700. For example, this may result from the instrument navigating past a bend in the bronchial lumens. Due to the non-linear bend, tendons 1702 and 1703 in endoscope 1700 need to lengthen or shorten at the proximal end by a length to accommodate the non-linear bend, which length is represented by F(τ). Extension and compressive forces exist on the lumens/conduits at the top and bottom of the bend, as depicted by arrows 1709 (extension forces) and 1710 (compressive forces) respectively. These forces exist because the distance along the top of the bend is longer than the neutral axis, and the distance along the inside of the bend is shorter than the neutral axis.

Figure 17F:
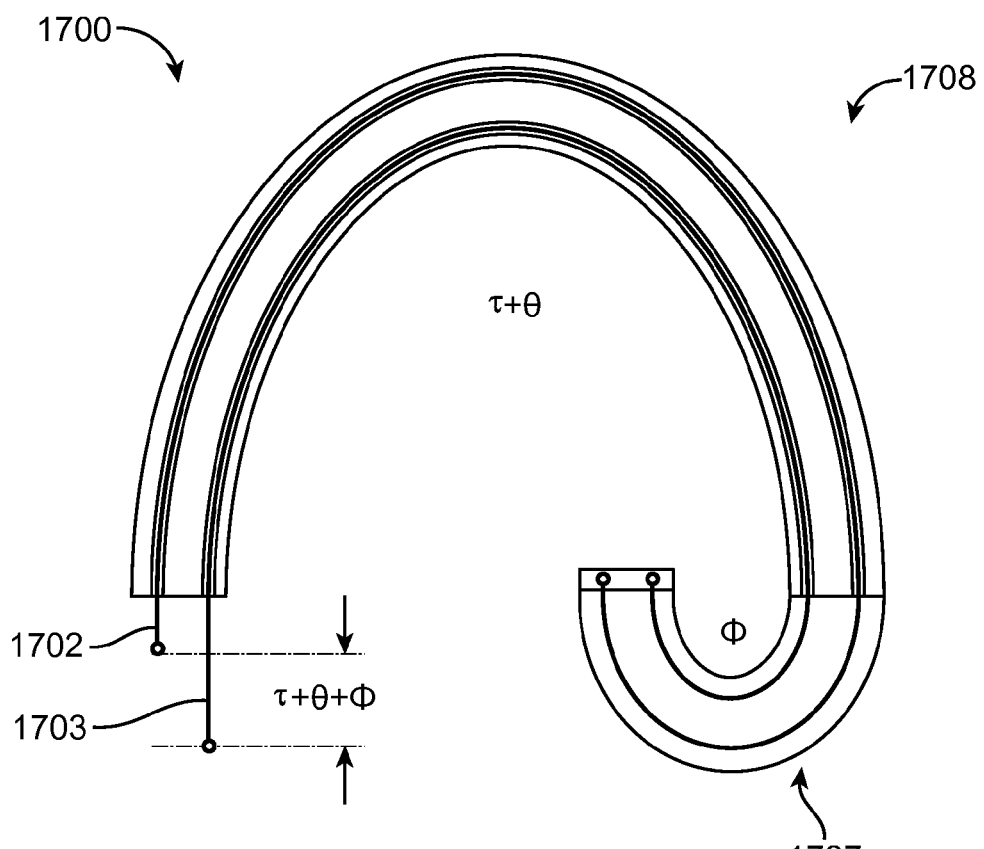

FIG. 17F illustrates the mechanics of articulating the distal bending section 1707 of the endoscope 1700 in the same direction as bend τ, where one would pull tendon 1703. This results in compressive forces along the length of the flexible instrument (as previously described), and tendon 1703 also exerts downward forces against the non-linear conduit through which it passes, which applies an additive compression in the shaft 1708 previously compressed by the anatomical tortuosity. Since these compressive leads are additive, the shaft 1708 will further bend in the same direction as the distal bending section 1707. The additional compressive force along the non-linear conduit may be undesirable because: (i) it may unintentionally force the flexible instrument against the anatomy; (ii) potential for injury distracts the operator because he/she has to constantly monitor what the shaft is doing, when he/she should be able to "assume" the anatomy is governing the profile of the instrument shaft; (iii) it is an inefficient way to bend the instrument, (iv) it is desired to isolate bending at the distal section to aid in predictability and controllability (i.e., ideal instrument will have bending section that bends as commanded and is not a function of the anatomical non-linear path), and (v) it forces a user to pull on a tendon 1103 an unpredictable additional length (φ+θ+τ).

Figure 17G:
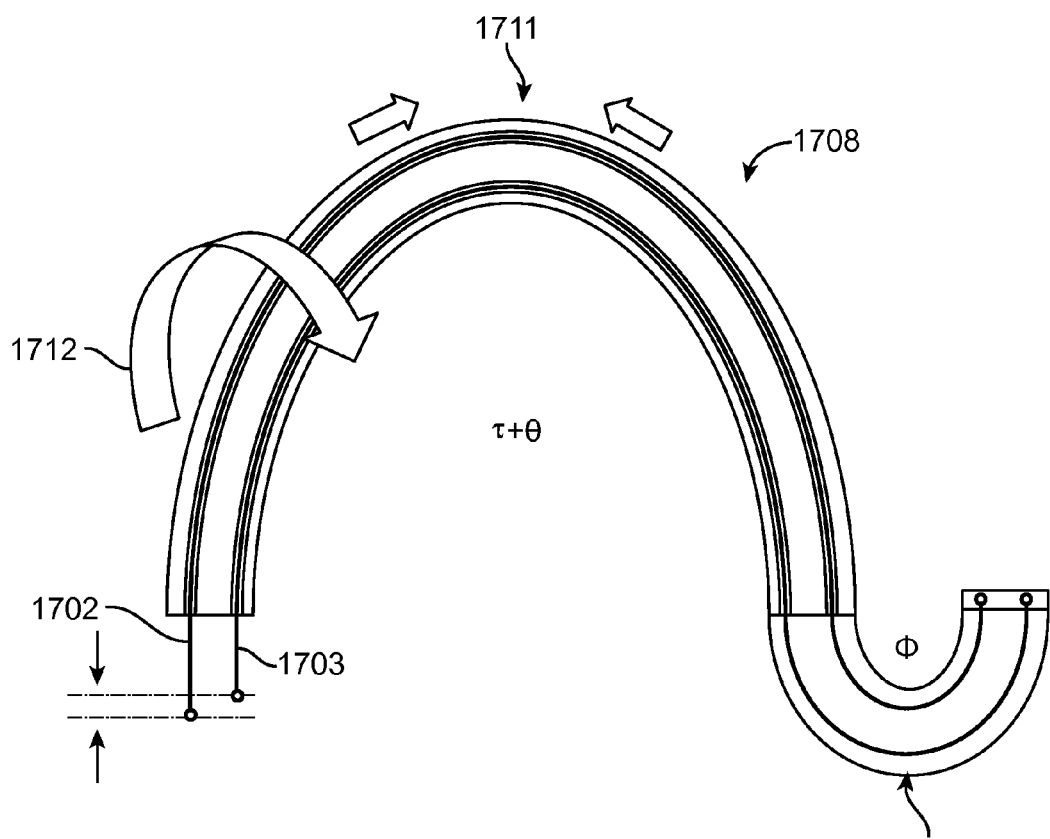
Figure 17H:
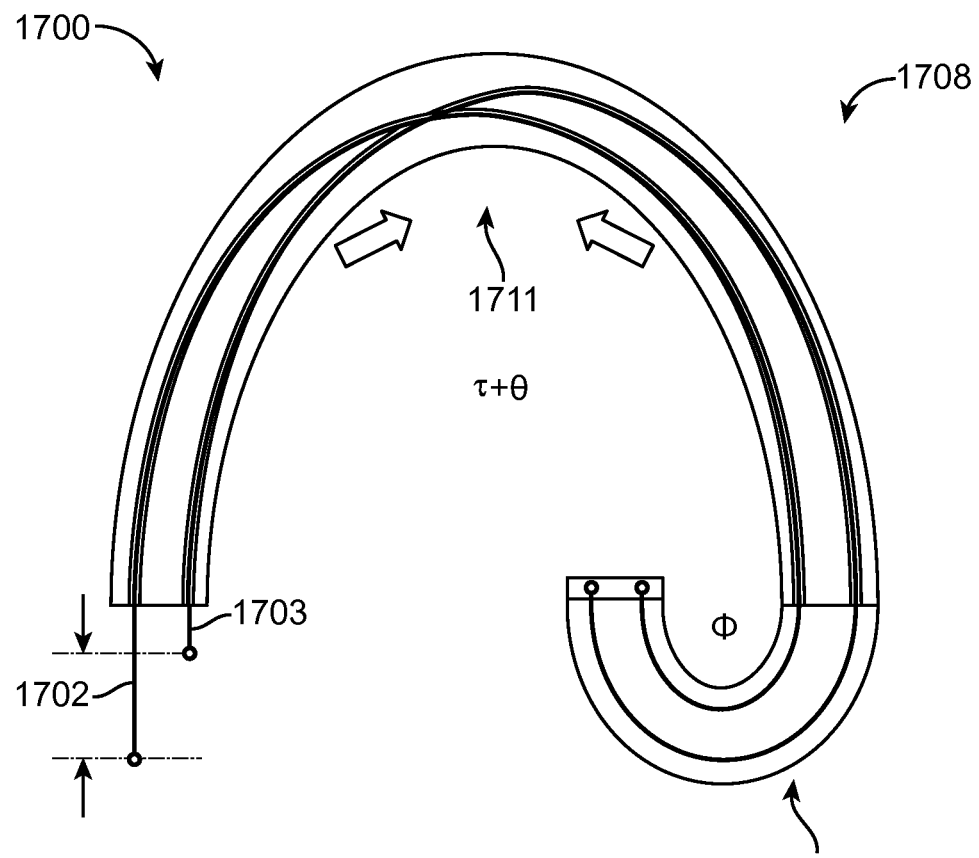

FIG. 17G illustrates a scenario where one desires to articulate the distal end opposite to bend τ, requiring pulling tendon 1702. Pulling tendon 1702 applies a compressive load 1711 along the top of the curve, which is in contrast to the extension loads for the bend in its resting state as shown in FIG. 17E. Tendons 1702 will attempt to return to its lowest energy state, i.e., where the compressive load 1711 rests on the inside of the bend τ, and cause the shaft 1708 to rotate in the direction of the arrow 1712 so that the tendon 1702 rests on the inside of the bend τ. As shown in FIG. 17H, the rotation 1712 from tension on tendon 1702 moves the compressive load 1711 to return to the inside of the bend and causes the distal bending section 1707 to curl back in the direction of bend τ, resulting in articulation opposite to that intended. The tension on tendon 1702, and the ensuing rotation 1712, in practice returns endoscope 1700 to the same state as in FIG. 17F. The phenomenon where the distal end articulation curves back towards bend τ is known as "curve alignment." It will be appreciated that curve alignment results from the same forces that cause muscling, wherein those forces result in undesirable lateral motion in the case of muscling and undesirable rotational motion in the case of curve alignment. It is noted that the discussions of the theory of muscling and curve alignment is provided not by way of limitation, and embodiments of the present invention are not in any way limited by this explanation.

FIGS. 17I and 17J illustrate how the muscling and curve alignment phenomena is substantially resolved through the provision of a helixed section in an embodiment of the present invention, such as 1510 in FIG. 15. As shown in FIG. 17I, helixing the control lumens around endoscope 1700, such as in helixed section 1510 from FIG. 15, radially distributes compressive loads 1714 from a single tendon 1715 around endoscope 1700. Because a tensioned tendon 1715 symmetrically transmits the compressive load 1714 in multiple directions around the neutral axis, the bending moments imposed on the shaft are also symmetrically distributed around the longitudinal axis of the shaft, which counterbalance and offset opposing compressive and tensile forces. The distribution of the bending moments results in minimal net bending and rotational forces, creating a lowest energy state that is longitudinally parallel to the neutral axis, as represented by the dotted line 1816. This eliminates or substantially reduces the muscling and curve alignment phenomena.

In some embodiments, the pitch of helixing can be varied to affect friction and the stiffness of the helixed section. For example, the helixed section 1510 may be shorter to allow for a larger non-helixed section 1509, resulting in a larger articulating section and possibly less friction.

Helical control lumens, however, create several trade-offs. Helical control lumens still do not prevent buckling from tension in the tendons. Additionally, while muscling is greatly reduced, "spiraling"—the curving of the shaft into a spiral, spring-like pattern due to tension in the tendons—is very common. Moreover, helical control lumens requires compensation for additional frictional forces as the tendon travels through the lumen for longer distances.

Figure 18:
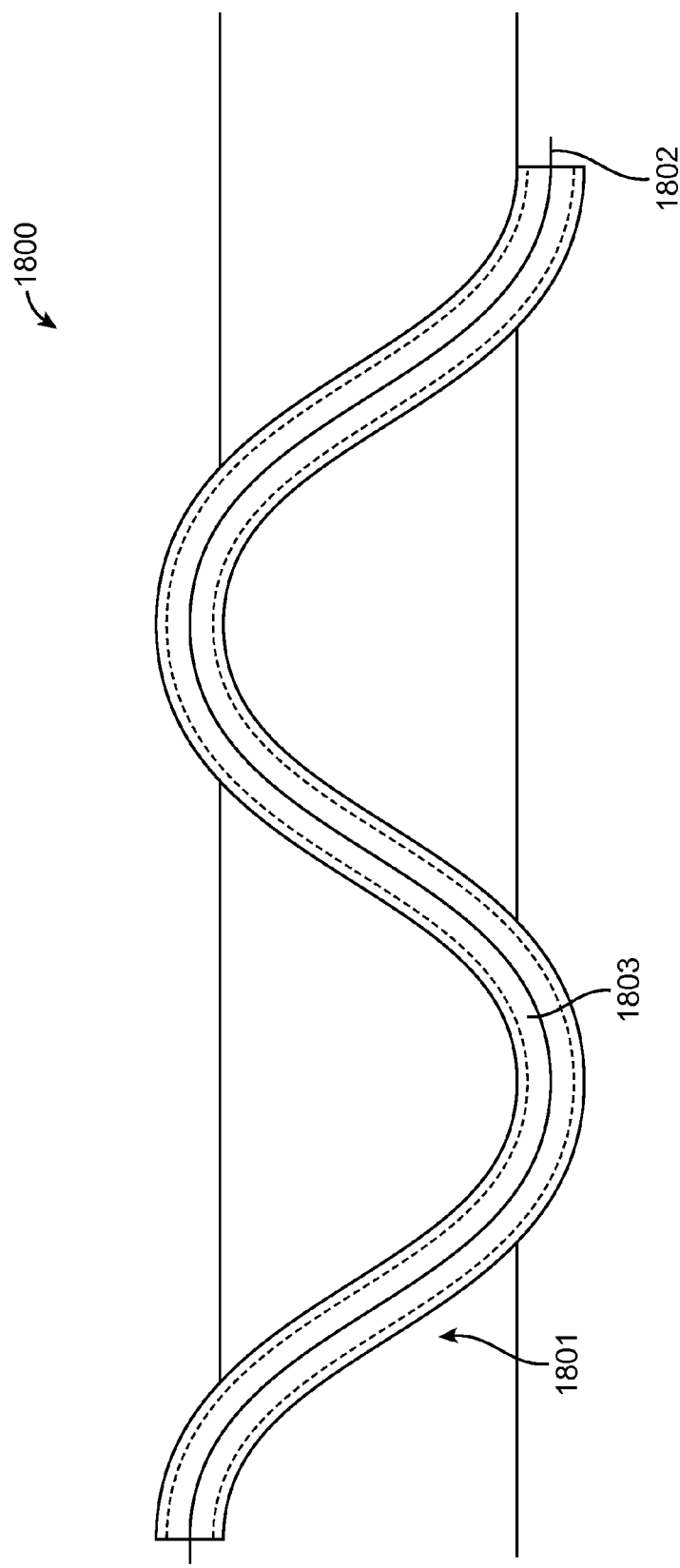
FIG. 18 illustrates the structure of a flexible endoscopic tool with an axially stiff tube within a lumen, in accordance with an embodiment of the present invention.

FIG. 18 illustrates the structure of a flexible endoscopic tool with an axially stiff tube within a lumen, in accordance with an embodiment of the present invention. In FIG. 18, a section of an endoscopic tool has a single lumen 1801 with a pull wire 1802 wrapped in a helical pattern around the shaft 1800. Inside the lumen, an axially stiff tube 1803 "floats" around the pull wire 1802 and within the lumen 1801. Anchored at the beginning and end of the helical portion of the shaft 1800, the floating tube 1803 extends and compresses in response to tension in pull wire 1802 and external tortuosity, relieving the walls of lumen 1801 from the extension and compression forces. In some embodiments, the tube 1803 may be anchored by control rings at the beginning and end of the lumen. Alternatively, tube 1803 may be anchored using solder, welding, gluing, bonding, or fusing methods to the beginning and end of the lumen. In some embodiments, geometric engagement, such as flared geometries, may be used to anchor tube 1803. In various embodiments, the tube 1803 may be formed from hypodermic tubes, coil pipes, Bowden cables, torque tubes, stainless steel tubes, or nitinol tubes.

The embodiment in FIG. 18 may be constructed by fixedly attaching the tubes to a distal end piece and proximal end piece and collectively twisting the tubes by rotating either or both end pieces. In this embodiment, the rotation of the end piece(s) ensures that the tubes are helixed in the same pitch, manner, and orientation. After rotation, the end pieces may be fixedly attached to the lumen to prevent further rotation and restrict changes to the pitch of the helixing.

Figure 19:
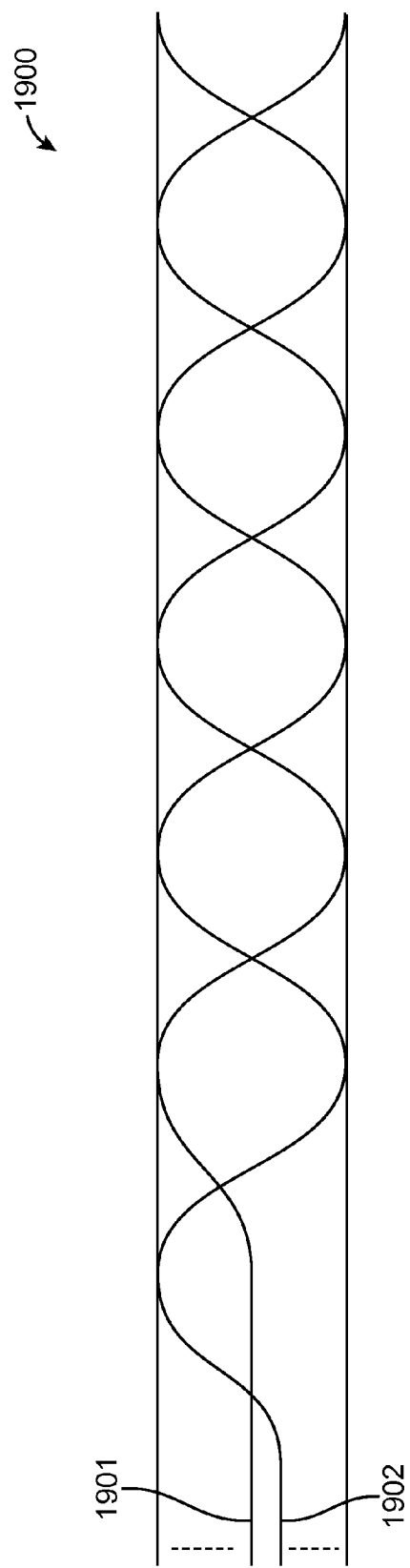
FIG. 19 illustrates the structure of a helical pattern within a lumen of a flexible endoscopic tool, in accordance with an embodiment of the present invention.

FIG. 19 illustrates the structure of a helical pattern within a lumen of a flexible endoscopic tool, in accordance with an embodiment of the present invention. In FIG. 19, lumen 1900 contains structures 1901 and 1902 that form a helical or spiraled pattern along its walls. In preferred embodiments, the structures are formed from materials that are axially stiff and tube-like in shape. In some embodiments, the structures may be formed from hypodermic tubes ("hypo tube"), coil pipes, or torque tubes. As shown by structures 1901 and 1902, the structures may have different starting points along the walls of lumen 1900. The materials, composition, and characteristics of structures 1901 and 1902 may also be selected and configured for desired stiffness and length. The pitch of the helical pattern formed by structures 1901 and 1902 may also be configured for a desired stiffness and flexibility of lumen 1900. In some embodiments, lumen 1900 may be the main central lumen of a flexible endoscope, such as leader 1600 from FIG. 16.

Figure 20A:
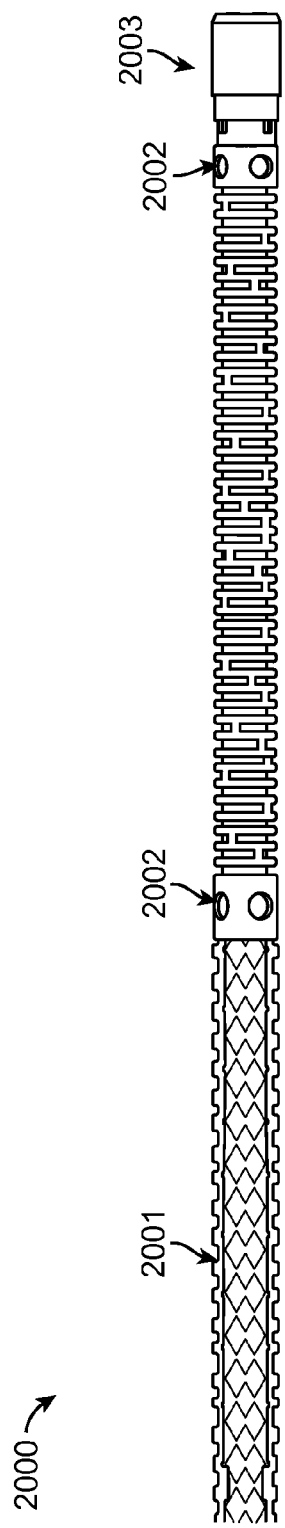
FIG. 20A illustrates an endoscopic tool from a robotic endolumenal system, in accordance with an embodiment of the present invention.

FIG. 20A illustrates an endoscopic tool from a robotic endolumenal system, in accordance with an embodiment of the present invention. Endoscopic tool 2000 may comprise of a flexible shaft section 2001 proximal to a support base (not shown) and a flexible articulating section 2002 coupled to a distal tip 2003. Similar to the leader 2005, endoscopic tool 2000 may be articulated by placing tensile loads on tendons within the shaft.

Figure 20B:
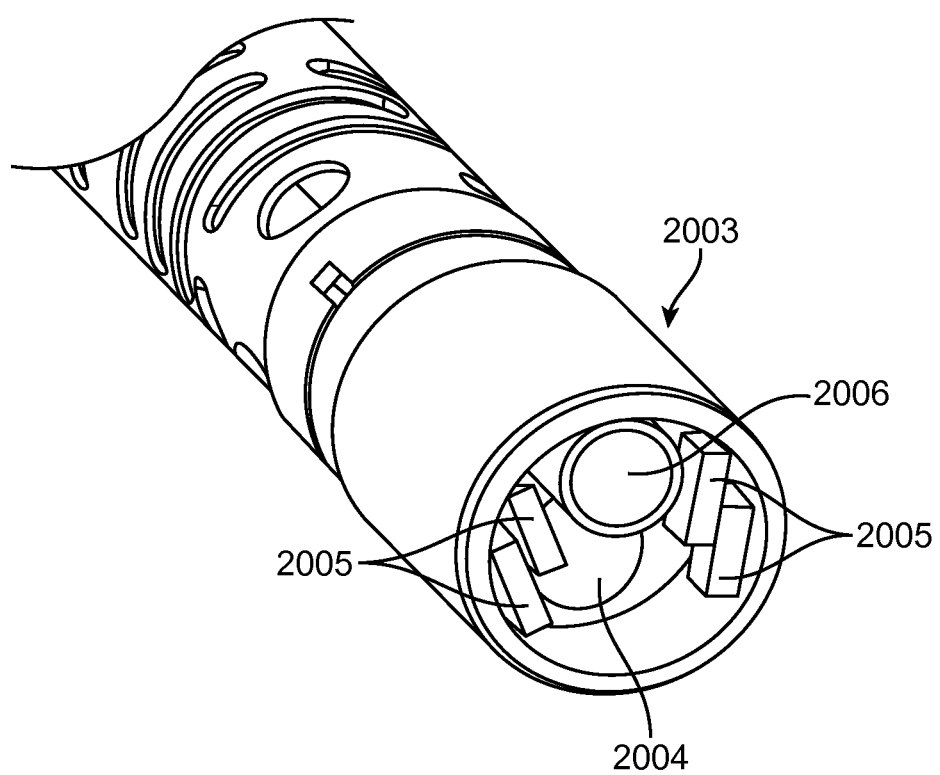
FIG. 20B illustrates an alternative view of endoscopic tool 2000 from FIG. 20A.

FIG. 20B illustrates an alternative view of endoscopic tool 2000 from FIG. 20A. As shown in FIG. 20B, the distal tip 2003 may comprise a working channel 2004, four light emitting diodes 2005, and a digital camera 2006. In conjunction with the LEDs 2005, the digital camera 2006 may be used, for example, to capture real-time video to assist with navigation within anatomical lumens. In some embodiments, the distal tip 2003 may comprise an integrated camera assembly which houses a digital imaging means and illumination means.

The working channel 2004 may be used for the passage of intraoperative instruments, such as bending flexures for precise articulation at an operative site. In other embodiments, working channels may be incorporated to provide additional capabilities such as flush, aspiration, illumination or laser energy. The working channel may also facilitate the routing of control tendon assemblies and other lumens needed for the aforementioned additional capabilities. The working channel of the endoscopic tool may also be configured to deliver a variety of other therapeutic substances.

Such substances may be cryogenic for ablation, radiation, or stem cells. These substances may be precisely delivered precisely to a target site using the insertion, articulation, and capability of the endoscopic tool of the present invention. In some embodiments, the working channel may be as small at 1.2 millimeters in diameter.

In some embodiments, an electromagnetic (EM) tracker may be incorporated into the distal tip 2003 in order to assist with localization. As will be discussed later, in a static EM field generator may be used to determine the location of the EM tracker, and thus distal tip 2003 in real-time.

Images from camera 2006 may be ideal for navigating through anatomical spaces. Thus, obscuring of the camera 2006 from internal bodily fluids, such as mucus, may cause problems when navigating. Accordingly, the distal end 2003 of endoscopic tool 2000 may also include means for cleaning the camera 2006, such as means for irrigation and aspiration of the camera lens. In some embodiments, the working channel may contain a balloon that may be inflated with fluid around the camera lens and aspirated once the lens was clear.

The endoscopic tool 2000 enables the delivery and manipulation of small instruments within the endolumenal space. In a preferred embodiment, the distal tip may be miniaturized in order to perform endolumenal procedures, maintaining an outer diameter of no more than three millimeters (i.e., nine French).

Figure 21:
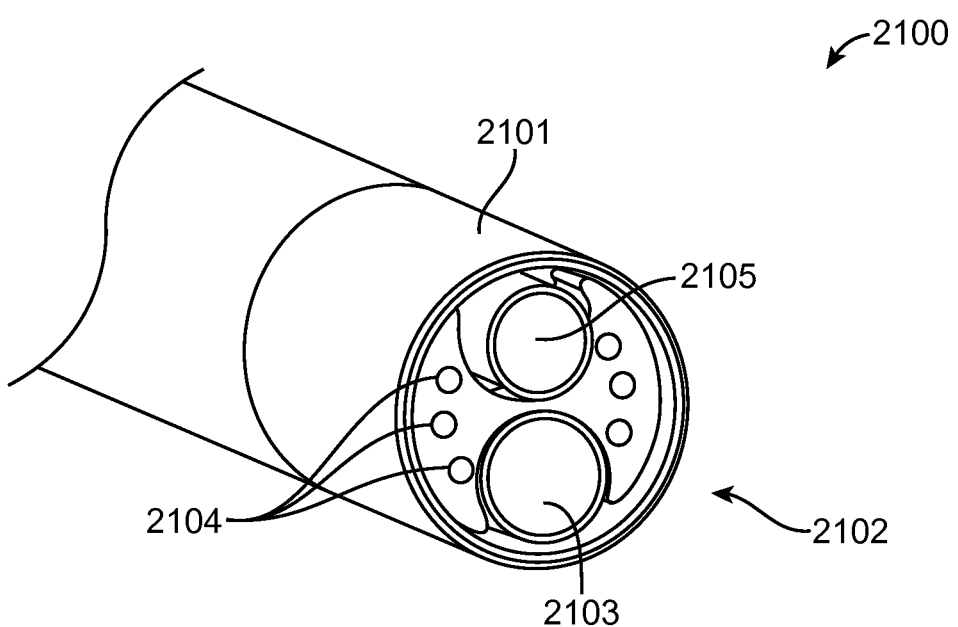
FIG. 21 illustrates the distal end of an endoscopic tool, in accordance with an embodiment of the present invention.

FIG. 21 illustrates the distal end of an endoscopic tool, in accordance with an embodiment of the present invention. As in FIG. 21A, endoscopic tool 2100 includes a distal end 2101 with an outer casing 2102. Casing 2102 may be constructed from a number of materials including stainless steel and polyether ether ketone (PEEK). The distal end 2101 may be packed with a working channel 2103 for slidingly providing tool access and control. The distal end 2101 may also provide for an array of light emitting diodes 2104 for illumination with use of the camera 2105. In some embodiments, the camera may be part of a larger sensor assembly that includes one or more computer processors, a printed circuit board, and memory. In some embodiments, the sensor assembly may also include other electronic sensors such as gyroscopes and accelerometers (usage discussed later).

8. Endoscopic Tool Manufacture.

In background, steerable catheters are traditionally manufactured by braiding wires or fibers, i.e., braid wire, around a process mandrel with pull lumens in a braiding machine, i.e., braider, and a polymer jacket applied over the braid wires. Embodiments of the sheath and leader endoscopic tools may be constructed using aspects of steerable catheter construction methodologies.

Figure 22:
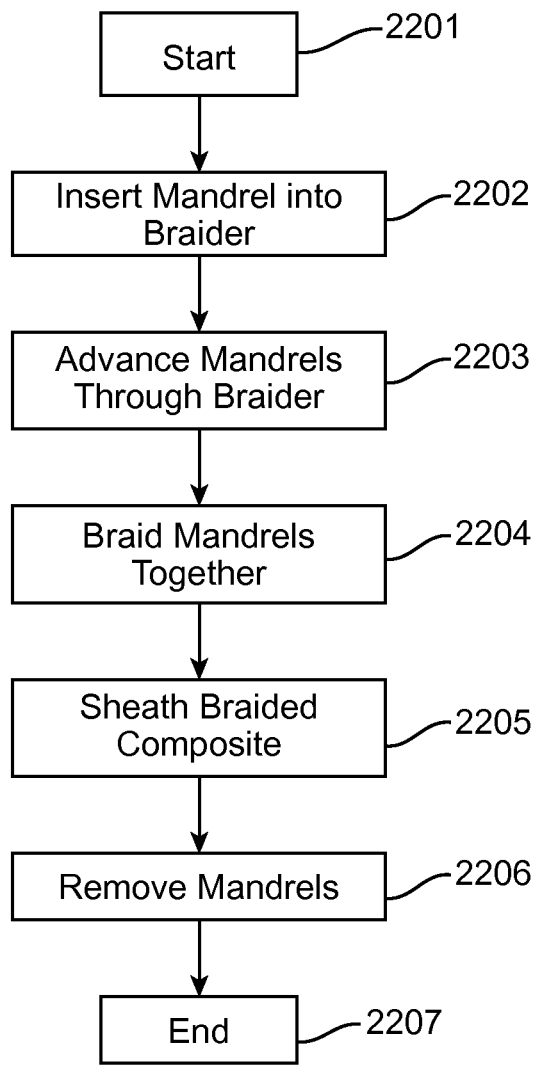
FIG. 22 illustrates a flowchart for a method of constructing an endoscopic device with helical lumens, in accordance with an embodiment of the present invention.

FIG. 22 illustrates a flowchart for a method of constructing an endoscopic device with helixed lumens, in accordance with an embodiment of the present invention. To start, in step 2201, a main process mandrel may be selected to create a cavity in the endoscope for a central lumen that may be used a working channel. Supplemental mandrels may be selected to create cavities in the wall of the endoscope for use as control (pull) lumens. The main process mandrel may exhibit larger outer diameters (OD) than the supplemental mandrels to reflect the relative size differential between a working channel and pull lumens. The supplemental mandrels may be constructed a metal or thermoset polymer that may or may not be coated with a lubricious coating, such as PTFE.

In step 2202, the main process mandrel may be inserted into a feed tube of a braider that rotates relative to a fixed braid cone support tube and braid cone holder. Similarly, the supplemental mandrels may also be inserted into the feed tube in parallel fashion to the main process mandrel. In traditional endoscope construction, smaller supplemental mandrels are passed through the center of the horn gears for braiding.

In step 2203, using a puller with a tread, the main process mandrel may be advanced through the feed tube. As the main process mandrel progresses, it eventually emerges through a center hole in a nose cone. Similarly, the supplemental mandrels are advanced through to also emerge through outer holes in the nose cone. This contrasts with traditional endoscope construction, where supplemental mandrels are typically advanced through separate feed tubes to emerge from the center of the horn gears.

In step 2204, the main process mandrel and supplemental mandrels are braided together using braid wire as they emerge through the nose cone. The nose cone provides a round, smooth shape on which the braid wire from the surrounding horn gears may easily slide around the main process mandrel during the braiding process. As both the main process mandrel and supplemental mandrels emerge from the nose cone, the nose cone rotates, ensuring that the supplemental mandrels in the outer holes are braided in a spiraled fashion around the main process mandrel. As the main process mandrel and supplemental mandrels are being braided together, the horn gears translate and rotate to lay braid wire around both the main process mandrel and supplemental mandrels at a pre-determined pattern and density.

This method of braiding is significantly different from traditional methods of endoscope construction, where the nose cone is typically held in a position that is radially fixed relative to the braid cone holder using a set screw keyed to the braid cone holder. Thus, specialized hardware is required for the braiding process in order to manufacture catheter-like endoscopes with helical control lumens.

Figure 23:
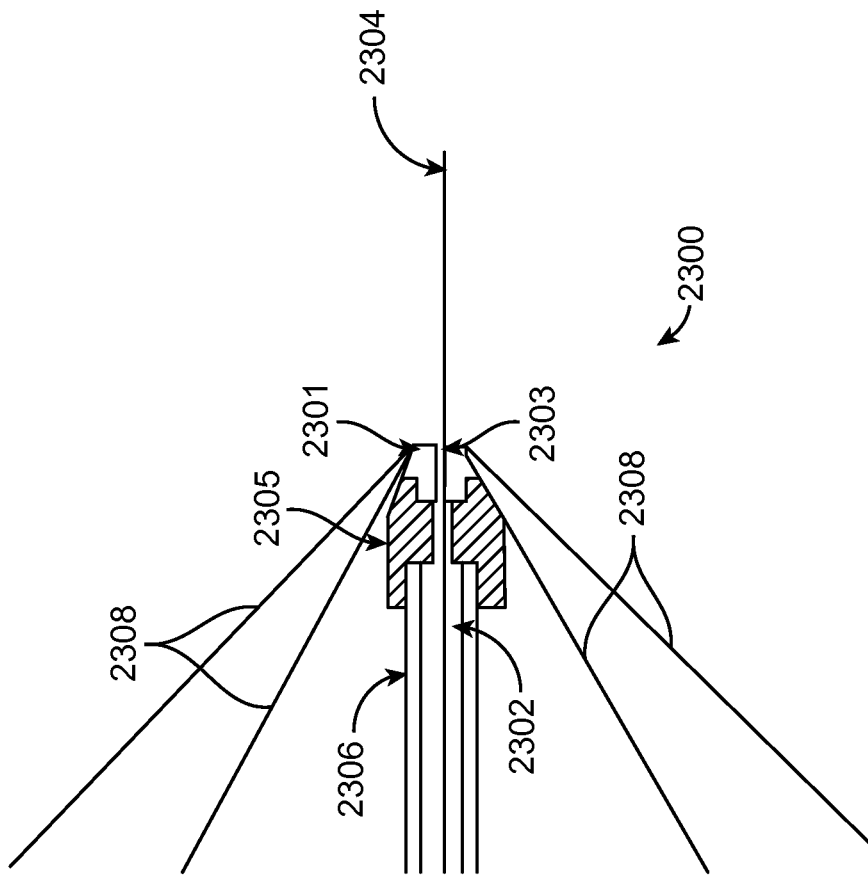
FIG. 23 illustrates a system for manufacturing a flexible endoscope, in accordance with an embodiment of the present invention.
Figure 23:
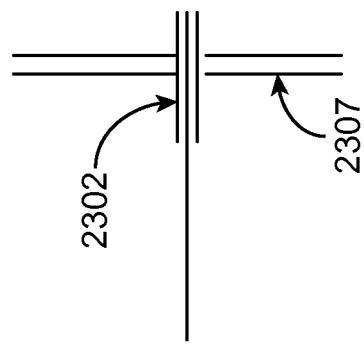

FIG. 23 illustrates a specialized system for manufacturing an endoscope with helical pull lumens, in accordance with an embodiment of the present invention. In system 2300, the nose cone 2301 may be fixedly coupled to a rotating feed tube 2302 using a set screw that holds the nose cone 2301 in a fixed position relative to the feed tube 2302. Thus, nose cone 2301 rotates as the feed tube 2302 rotates. In contrast, traditional systems typically use a set screw to fixedly couple the nose cone 2301 to the braid cone support holder 2305, which does not rotate.

The center hole 2303 of the nose cone 2301 may be aligned with the rotating feed tube 2302 in order to smoothly pull the main process mandrel 2304 through both structures. In some embodiments, the rotating feed tube 2302 has an outside diameter less than the interior diameter of the braid cone support tube 2306, also known as a mandrel guide tube, and an interior diameter larger than the circumferential space of the center hole 2303 of the nose cone 2301. The rotating feed tube 2302 may generally be large enough for the main process mandrel 2304 and the supplemental mandrels to be passed through to the nose cone 2301 without entanglement. In some embodiments, the rotating feed tube 2302 may be long enough to pass through the center of the horn gears of the braider. In some embodiments, the rotating feed tube 2302 may be attached to a mechanism that may hold bobbins of material for the supplemental mandrels that will be passed through the feed tube 2302 to supplemental holes around the nose cone 2301.

In some embodiments, the feed tube 2302 may be attached to a drive mechanism that controls the rate of rotation of the feed tube 2302 and thus the rotation of the nose cone 2301. In some embodiments, the drive mechanism may be a rotating gear 2307. As the braider is braiding the braid wires 2308 around the main process mandrel 2304, the drive mechanism is either geared to the braider itself or independently controlled to vary or hold constant the rate of rotation of the rotating feed tube 2302 and thus the rate of rotation of the nose cone 2301. The rate of rotation and the rate of braiding will govern the pitch of the supplemental mandrels on the main process mandrel 2304. As discussed earlier, this may affect the flexibility, stiffness, and "pushability" of the device.

Figure 24:
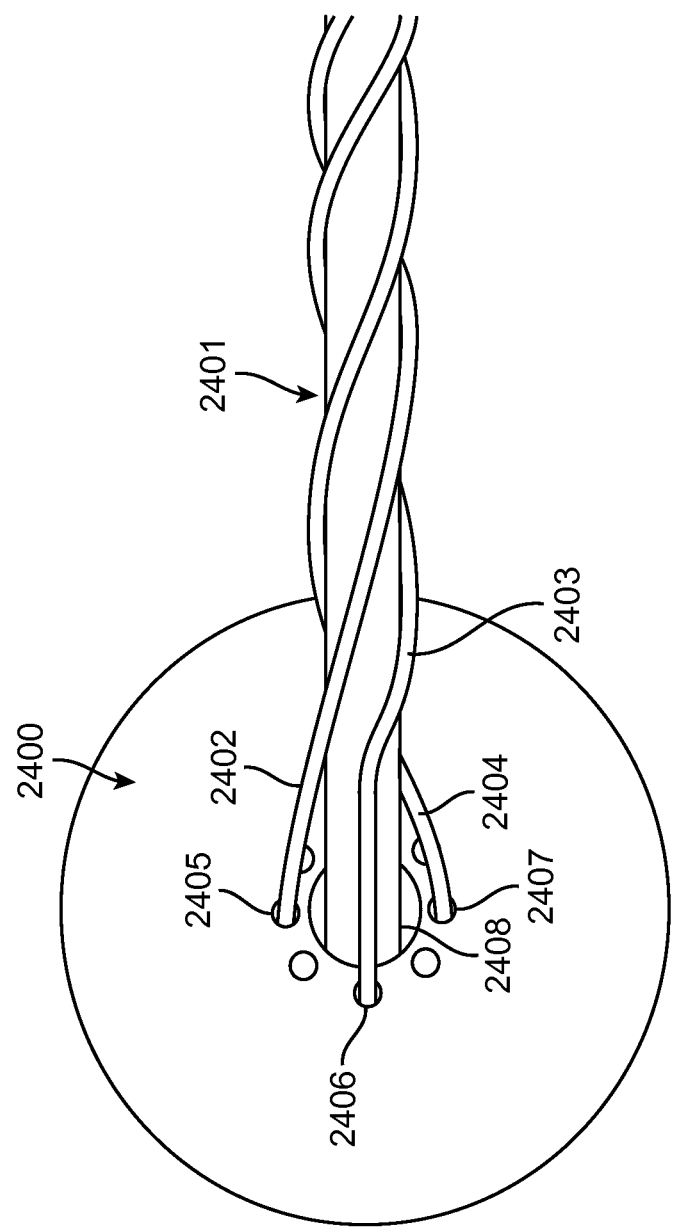
FIG. 24 illustrates a specialized nose cone for manufacturing an endoscopic device with helical pull lumens, in accordance with an embodiment of the present invention.

FIG. 24 illustrates a specialized nose cone for manufacturing helical lumens in an endoscopic device, in accordance with an embodiment of the present invention. Rotating the nose cone 2400 at the same time that the main process mandrel 2401 is pulled through the nose cone 2400 allows for supplemental mandrels 2402, 2403, and 2404 to be applied in a helical pattern around the mandrel 2401 through supplemental holes 2405, 2406, and 2407 respectively that surround the center hole 2408, similar to how the horn gears braid the braid wire around the main process mandrel 2401.

In another embodiment, varying the circumferential orientation of the pull lumens may change the stiffness of the helical section of the endoscope. In manufacture, this may be achieved by altering the pitch of the supplemental, spiraling mandrels. As the pitch (i.e., the angle off the longitudinal axis) of the mandrels increases, the bending stiffness of the braided composite decreases. Conversely, as the pitch of the supplemental mandrels decreases, the bending stiffness increases. As shown in FIG. 15B, in some embodiments, the pitch of the supplemental mandrels may be varied within the helixed portion (1510). In those embodiments, the bending stiffness of the braided composite may vary even within the helixed portion.

Returning to FIG. 22, in step 2205, upon completion of the braided process, a polymer coating or jacket may be sheathed, heated, and bonded to the braiding composite. The polymer coating may also be applied in an over-extrusion or a film-cast process. In step 2206, after bonding, the mandrels may be removed from the braided composite to create a central lumen or working channel (main process mandrel) for camera and light tools, and several control lumens (supplemental mandrels) for steering control. Having removed the mandrels, the braided composite may be finished for completion (2207).

During the braiding process, the braiding machine may be stopped to make alterations to the braided composite. In some embodiments, one alteration may be the addition of straight wires or reinforcement rods. Reinforcement rods may significantly change the buckling, axial and bending stiffness of a braided laminated composite. Reinforcement rods may be particularly helpful for longer endoscopes which may require specialized anti-buckling construction or manual assistance to reduce the buckling of the device so that it may be inserted into a patient. In some embodiments, the braiding machine may be configured to selectively braid reinforcement rods that may be pulled from holes in the nose cone onto the main process mandrel, where the reinforcement rods are captured and held in place by the braid wire. The absence of reinforcement rods in the distal region of the resulting endoscope preserves the device's flexibility in the distal end while increasing the stiffness in the proximal region. This combination of properties makes the resulting endoscope easier for a physician to navigate, insert, and push the device into an endolumenal cavity of a patient.

Applying supplemental mandrels onto a main process mandrel using holes in a rotating nose cone provides a number of manufacturing advantages. By using holes in the nose cone, the mandrels are not pushed from the horn gears. Pushing mandrels from the center of the individual horn gears, which are also responsible for weaving the braid wire, results in the mandrels being interwoven with the braid wire, which locks the resulting braid matrix in place longitudinally. This form of construction, known as "zero degree construction," limits the ability of the manufacturer to adjust the braid matrix for desirable flexibility or hoop strength. In zero degree construction, the supplemental mandrel is necessarily confined in an "over-under manner" by the braid, resulting in all clockwise braided braid wire being woven "over" the supplemental mandrels, while all counter-clockwise braided braid wire is woven "under" the supplemental mandrels. As zero degree construction locks the supplemental mandrels in place radially, it may be undesirable where varying the pitch of the supplemental mandrel along the main process mandrel is required.

Additionally, use of the horn gears as a pass-through for the supplemental mandrels limits the number of supplemental mandrels that may be applied to the main process mandrel. For example, a sixteen carrier braider can apply up to eight mandrels, a twenty-four carrier braider can only have up to twelve mandrels. In contrast, use of holes in the nose cone allows any number of mandrels to be passed through to the main process mandrel.

In some embodiments, the supplemental mandrels may be applied to the main process mandrel without the benefit of a second, outer layer of braid wire. Instead, the supplemental mandrels may be applied without braid wire. In those embodiments, the bonded/fused polymer jacket may hold the mandrels, and thus lumens in place. Alternatively, in some embodiments, the mandrels may be held in place using a casting around the braided composite. Since the outer braid layer is absent from the manufacturing endoscopic tool, the diameter and circumference of the device cross-section is reduced. Alternatively, the supplemental mandrels may be held in place by sleeving a polymer jacket over the main process mandrel. In some embodiments, the casting may be the same material as the exterior material for the endoscopic tool.

In some embodiments, the supplemental mandrels may be braided onto the main process mandrel much like the braid wire. For example, in some embodiments, the supplemental mandrels may be braided using the even numbered horn gears, while held in place by braid wire braided using the odd numbered horn gears. In this way, the supplemental mandrels, and thus the lumens may be woven into the walls of the central lumen. As an added benefit, embodiments manufactured using this means also tend to have lower circumferential area.

Alternatively, in some embodiments, the helixed lumen structures may be manufactured using extruded molds. These molds may generate the helixed lumen structures to create a jacket from PTFE, pebax, polyurethane, and nylon. In some embodiments, the extruded structures may be formed using a mold around a braided mandrel.

In some embodiments, the helical lumen construction may be performed by rotating the main process mandrel as it is being drawn through the braider. By rotating the main process mandrel, instead of the nose cone, the supplemental mandrels may be drawn through either a fixed nose cone or through the center of the horn gears during the braiding process. In this embodiment, the nose cone may be fixedly coupled to the nose cone holder and the main process mandrel is rotated as it drawn through the nose cone.

Construction of sheath 1500 from FIG. 15 and leader 1600 from FIG. 16 are substantially the same. Thus, one of skill in the art would understanding that the same principles apply to both tools.

9. Endolumenal Navigation.

In an embodiment of the present invention, navigation of the endoscopic tool through anatomical lumens may involve use of computer-generated three-dimensional maps based on a collection of two-dimensional images created by low dose computerized tomography (CT) scans. Two-dimensional CT scans, each representing a cutaway view of the patient's internal anatomy, may be collected during pre-operative procedures. These scans may be analyzed to determine cavities and anatomical spaces within the patient, such as branches of a lung or the path of a urethra.

Having been analyzed to determine the relevant anatomical spaces within the patient, the spaces may be expressed as lumens with centerline coordinates, i.e., coordinates representing the center of the lumen, in three-dimensional space. The volume of those cavities may be represented as a specific measurement of diameter distance at each centerline coordinate. By tracking the centerline and the corresponding diameter distance measurements, a computer-generated model of a three-dimensional lumen may be generated. Grid coordinate data may thus be used to express three-dimensional spaces and cavities that represent the patient's anatomy.

Figure 25A:
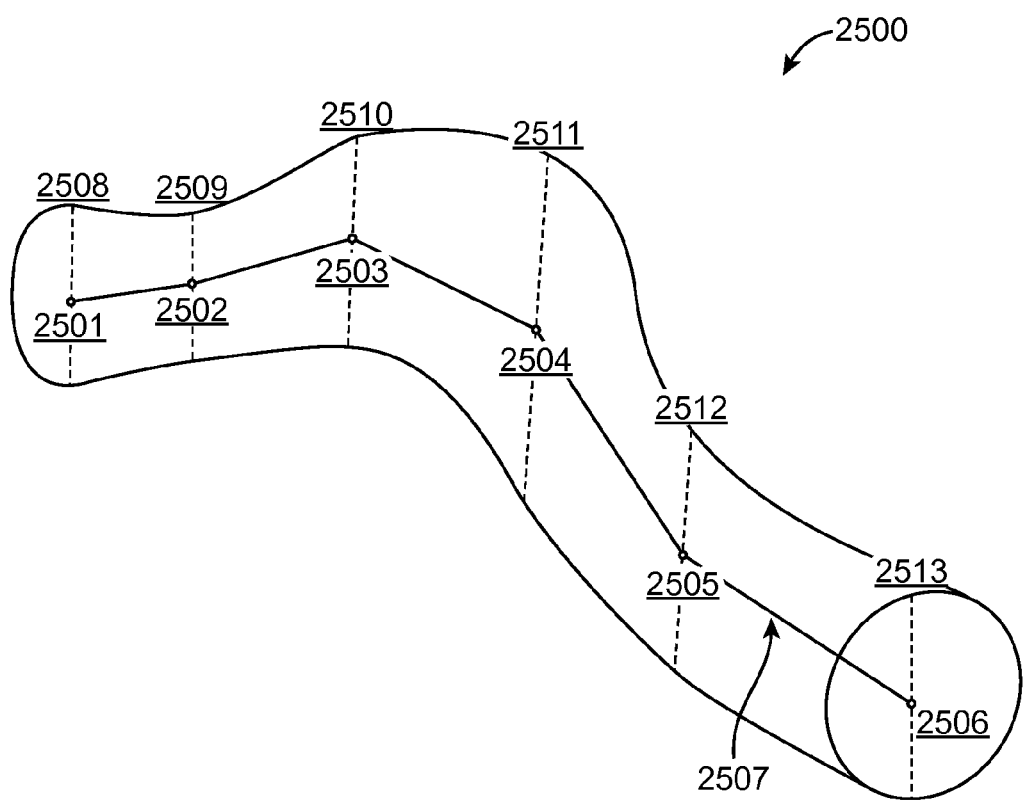
FIGS. 25A and 25B illustrates the relationship between centerline coordinates, diameter measurements and anatomical spaces.

FIG. 25 illustrates the relationship between centerline coordinates, diameter measurements and anatomical spaces. In FIG. 25A, anatomical lumen 2500 may be roughly tracked longitudinally by centerline coordinates 2501, 2502, 2503, 2504, 2505, and 2506 where each centerline coordinate roughly approximates the center of the lumen. By connecting those coordinates, as shown by "centerline" 2507, the lumen may be visualized. The volume of the lumen may be further visualized by measuring the diameter of the lumen at each centerline coordinate. Thus 2508, 2509, 2510, 2511, 2512, and 2513 represent the measurements of the lumen 2500 at coordinates 2501, 2502, 2503, 2504, 2505, and 2506.

Figure 25B:
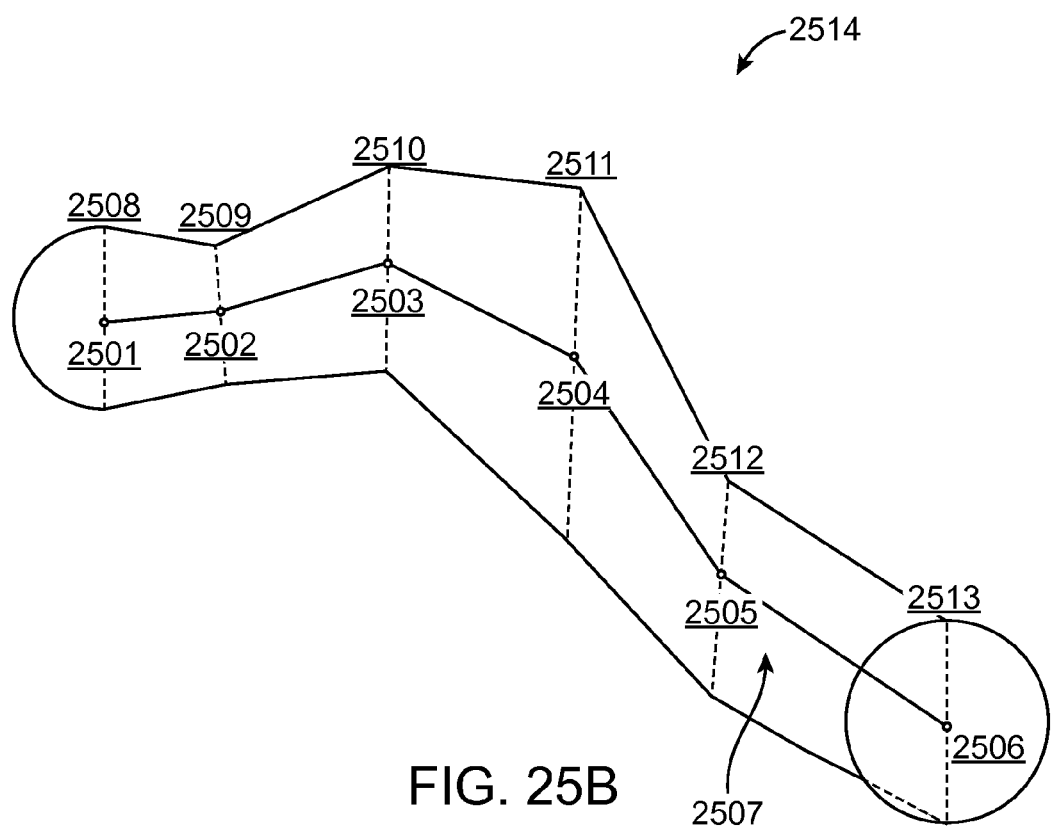

In FIG. 25B, lumen 2500 may be visualized in three-dimensional space by first locating the centerline coordinates 2501, 2502, 2503, 2504, 2505, and 2506 in three-dimensional space based on centerline 2507. At each centerline coordinate, the lumen diameter may be visualized as a two-dimensional circular space with diameters 2508, 2509, 2510, 2511, 2512, and 2513. By connecting those two-dimensional circular spaces in three-dimensions, lumen 2500 may be approximated as three-dimensional model 2514. More accurate approximations may be determined by increasing the resolution of the centerline coordinates and measurements, i.e., increasing the density of centerline coordinates and measurements for a given lumen or subsection. Centerline coordinates may also include markers to indicate point of interest for the physician, including lesions.

Having expressed, and subsequently generated, a three-dimensional model of the anatomical space, a pre-operative software package may also be used to analyze and derive an optimal navigation path based on the generated module. For example, the software package may derive shortest path to a single lesion (marked by a centerline coordinate) or several lesions. This path may be presented to the operator intra-operatively either in two-dimensions or three-dimensions depending on the operator's preference.

Figure 26:
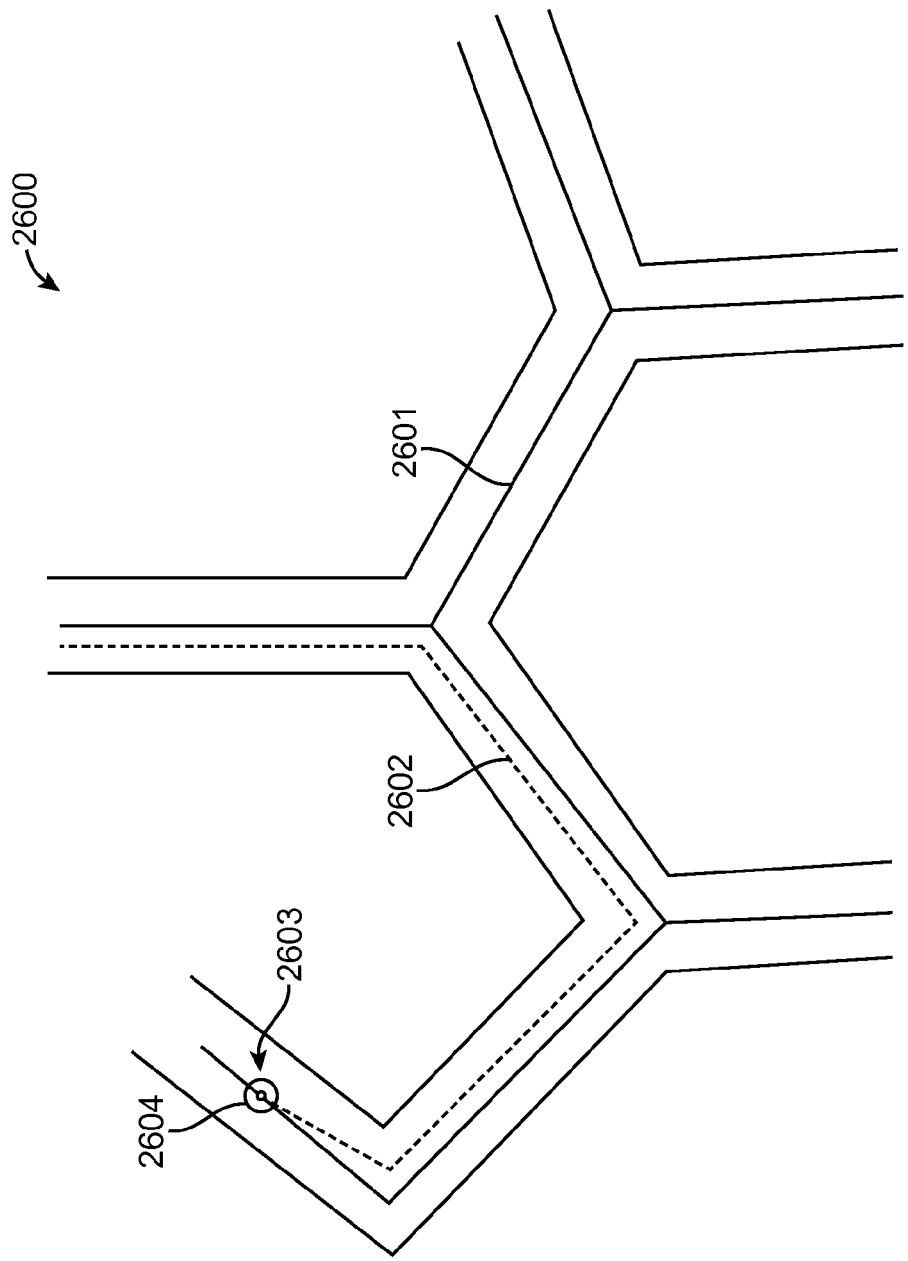
FIG. 26 illustrates a computer-generated three-dimensional model representing an anatomical space, in accordance with an embodiment of the invention.

FIG. 26 illustrates a computer-generated three-dimensional model representing an anatomical space, in accordance with an embodiment of the invention. As discussed earlier, model 2600 may be generated using centerline 2601 that was obtained by reviewing CT scans that were performed preoperatively. In some embodiments, computer software may be able to map the optimum path 2602 for the endolumenal system to access an operative site 2603 within model 2600, and thus the corresponding anatomical space. In some embodiments, the operative site 2603 may be linked to an individual centerline coordinate 2604, which allows a computer algorithm to topologically search the centerlines of model 2600 for the optimum path 2602 for the endolumenal system.

Tracking the distal end of the endoscopic tool within the patient's anatomy, and mapping that location to placement within a computer model, enhances the navigational capabilities of the endolumenal system. In order to track the distal working end of the endoscopic tool, i.e., "localization" of the working end, a number of approaches may be employed, either individually or in combination.

In a sensor-based approach to localization, a sensor, such as an electromagnetic (EM) tracker, may be coupled to the distal working end of the endoscopic tool to provide a real-time indication the progression of the endoscopic tool. In EM-based tracking, an EM tracker, embedded in the endoscopic tool, measures the variation in the electromagnetic field created by one or more static EM transmitters. The transmitters (or field generators), may be placed close to the patient to creates a low intensity magnetic field. This induces small-currents in sensor coils in the EM tracker, which are correlated to the distance and angle between the sensor and the generator. The electrical signal may then be digitized by an interface unit (on-chip or PCB) and sent via cables/wiring back to the system cart and then to the command module. The data may then be processed to interpret the current data and calculate the precise location and orientation of the sensor relative to the transmitters. Multiple sensors may be used at different locations in the endoscopic device, for instance in leader and sheath in order to calculate the individual positions of those components. Thus, based on readings from an artificially-generated EM field, the EM tracker may detect changes in field strength as it moves through the patient's anatomy.

Figure 27:
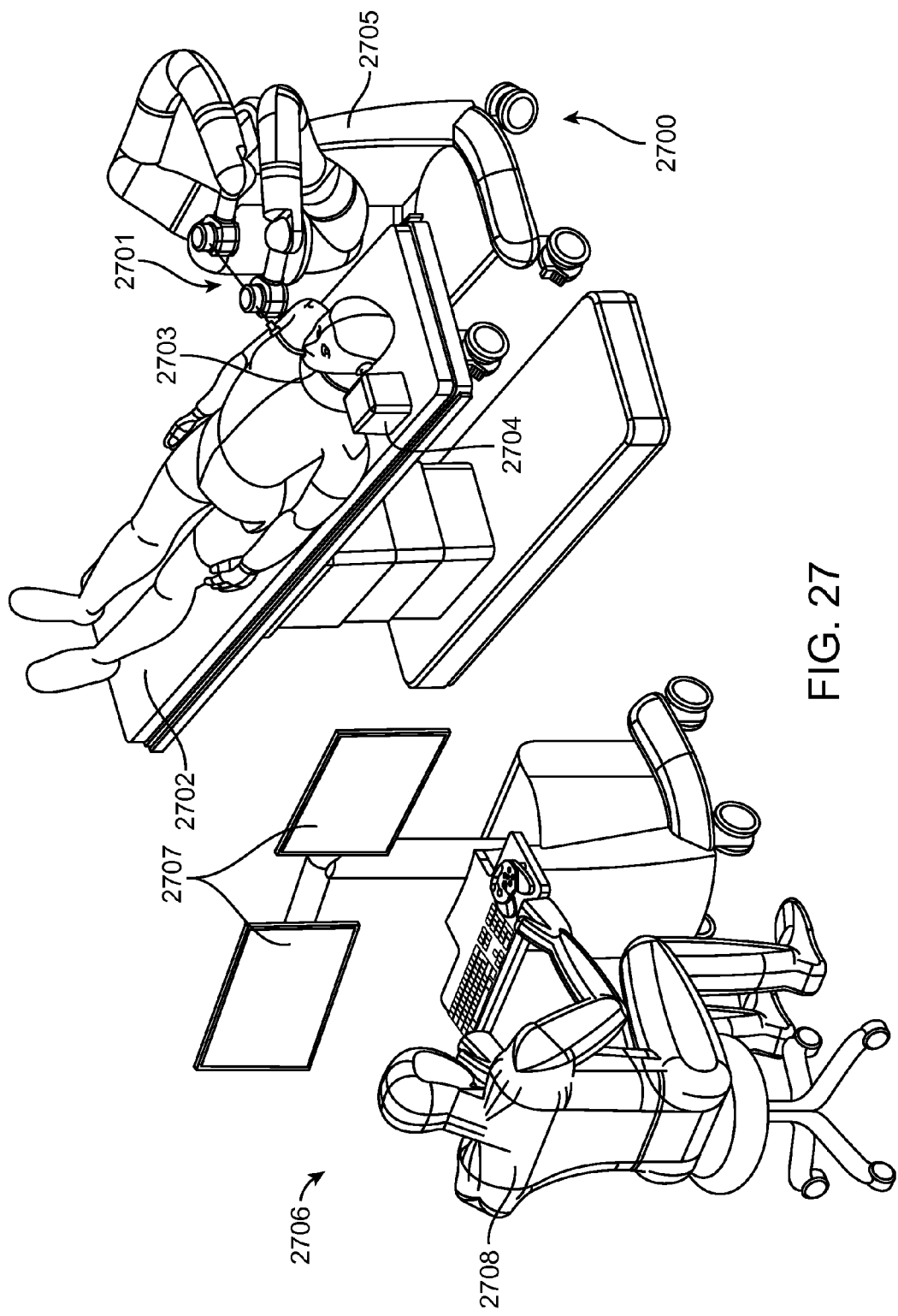
FIG. 27 illustrates a robotic endolumenal system that makes use of an electromagnetic tracker in combination with an electromagnetic field generator, in accordance with an embodiment in the present invention.

FIG. 27 illustrates a robotic endolumenal system that makes use of an electromagnetic tracker in combination with an electromagnetic field generator, in accordance with an embodiment in the present invention. As robotic system 2700 drives a robotically driven endoscopic tool 2701 into the patient 2702, an electromagnetic (EM) tracker 2703 at the distal end of the endoscopic tool 2701 may detect an EM field generated by EM field generator 2704. The EM readings of the EM tracker 2703 may be transmitted down the shaft of the endoscopic tool 2701 to the system cart 2705 and to command module 2706 (which contains relevant software modules, a central processing unit, a data bus and memory) for interpretation and analysis. Using the readings from EM tracker 2703, display modules 2707 may display the EM tracker's relative position within a pre-generated three-dimensional model for review by the operator 2708. The embodiments also provide for the use of other types of sensors, such as fiber optic shape sensors. While a variety of sensors may be used for tracking, the choice of sensor may be inherently limited based on (i) the size of the sensor within the endoscopic tool and (ii) the cost of manufacturing and integration the sensor into the endoscopic tool.

Prior to tracking a sensor through the patient's anatomy, the tracking system may require a process known as "registration," where the system finds the geometric transformation that aligns a single object between different coordinate systems. For instance, a specific anatomical site on a patient has two different representations in the CT model coordinates and in the EM sensor coordinates. To be able to establish consistency and common language between these coordinate systems, the system needs to find the transformation that links these two representations, i.e., registration. In other words, the position of the EM tracker relative to the position of the EM field generator may be mapped to a three-dimensional coordinate system to isolate a location in a corresponding three-dimensional model.

Figure 28:
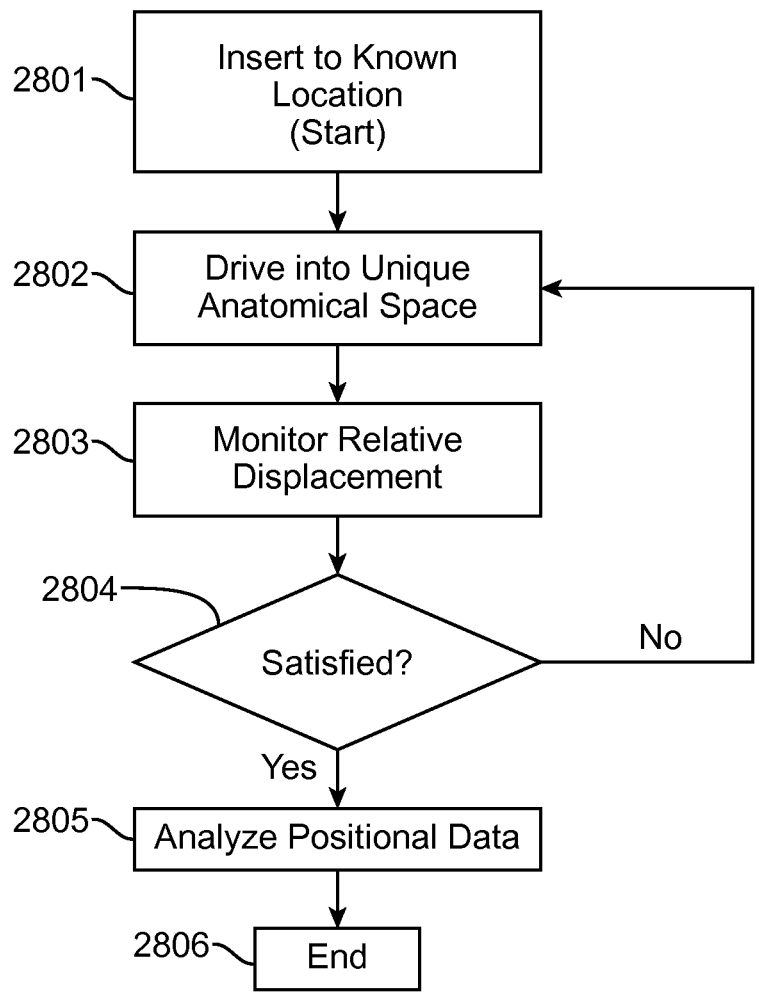
FIG. 28 illustrates a flow diagram for the steps for registration, in accordance with an embodiment of the present invention.

In some embodiments, registration may be performed in several steps. FIG. 28 illustrates a flow diagram for a registration process, in accordance with an embodiment of the present invention. To start, in step 2801, the operator must first position the working end of the endoscopic tool at a known starting location. This may involve using video imagery data from the endoscopic camera to confirm the starting location. Initial positioning may be accomplished by identifying anatomical features through a camera located at the working end of the endoscope. For example, in bronchoscopy, registration may be performed by locating the base of the trachea, distinguished by locating the two main bronchial tubes for the left and right lung. This location may be ascertained using video images received by the camera in the distal end of the endoscopic. In some embodiments, the video data may be compared to different cross sectional views of a pre-generated computer model of the patient's anatomy. By sorting through cross-sectional views, the system may identify the location associated with the cross-section with the smallest amount of differences, or "errors," to find the "match."

In step 2802, the operator may "drive" or "extend" the endoscopic tool into unique anatomical spaces that have already been mapped. For example, in bronchoscopy, the operator may drive the endoscope down unique bronchial paths from the base of the trachea. Because the base of the trachea splits into two bronchial tubes, an operator may drive the endoscopic tool into one tube and track the working end of the endoscopic tool using an EM tracker.

In step 2803, the operator monitors the relative travel of the endoscopic tool. Monitoring of the endoscopic tool may make use of either the EM tracker or fluoroscopy to determine relative movement of the endoscopic tool. Evaluation of the relative displacement of the working end of the endoscopic tool may be compared the computer model generated from pre-operative CT scan data. In some embodiments, the relative movement may be matched with centerlines in the computer model, where the transformation matrix leads to the least error is the correct registration. In some embodiments, the system and operator may track insertion data (discussed below) and orientation data from an accelerometer and/or gyroscope (discussed below).

In step 2804, the operator may decide to drive into more anatomical spaces (2802) and collect more locational information (2803) prior to comparing and analyzing the positional data. For example, in bronchoscopy, the operator retract the endoscope from one bronchial tube back the tracheal tube and drive the endoscope into another bronchial tube in order to collect more positional data. Once the operator is satisfied, the operator may stop driving (2802) and monitoring positional data (2803) and proceed to process the data.

In step 2805, the system may analyze the collected positional data and compare the data to pre-generated computer models to register the displacement of the endoscope within patient's anatomy to the model. Therefore, by comparing the movement in the patient's anatomy to the three-dimensional model of the patient's anatomy, the system may be able to register the tracker relative to both spaces—three-dimensional computer model vs. patient anatomical space. After analysis, the registration process may be complete (2806).

In some cases, it may be necessary to perform a "roll registration" in order to confirm the orientation of the endoscopic tool. This may be particularly important in step 2801 prior to driving into un-registered anatomical spaces. In bronchoscopy, proper vertical orientation ensures that the operator may distinguish between the right and left bronchi. For example within the base of the trachea, images of the left and right bronchi may appear very similar regardless of whether the camera is oriented at zero degrees or one-hundred eighty degrees. Roll registration may also be important because the kinematics of the endoscopic tool typically results in a slight rotation during tortuous navigation within a patient.

Roll registration may be important at the operative site when the working channel may be occupied by the sensor. For example, in embodiments with only a single working channel, upon reaching the operative site, the physician may need to remove the EM tracker from the endoscopic tool in order to make use of another tool, such as a grasper or forceps. Upon removal, however, the system may lose its localization capabilities without the EM tracker. Thus, when ready to leave the operative region, insertion of the EM tracker may require that the roll registration be again performed to ensure proper orientation.

In some embodiments, the rotation of the endoscopic tool may be tracked using an accelerometer mounted within the distal working end of the device. Use of an accelerometer to detect gravitational forces on the endoscope provides information regarding the location of the endoscopic tool relative to the ground. The location of the ground relative to the endoscope may be used to solve certain ambiguities. In bronchoscopy, for example, knowing the orientation (0 or 180 degrees) of the distal camera of the endoscope would help determine the appropriate bronchial branch at the start. During navigation, data from the accelerometer to track the direction of gravity, and thus orientation, may also be used to auto-correct the camera image displayed on the control console, ensuring that the displayed image is always oriented vertically.

In a preferred embodiment, a 3-axis MEMS-based sensor chip with an accelerometer may be coupled near the tip of the endoscopic device, on the same printed circuit board as the digital camera. The accelerometer measures the linear acceleration along the three different axes to calculate the velocity and direction of the catheter tip. It accelerometer also measures the direction of gravity and thus provides absolute information about the orientation of the endoscopic device. The accelerometer readings re be transmitted using digital or analog signals through a communication protocol like I2C. The signal may be transmitted through wiring to the proximal end of the catheter and from there to the system cart and command module for processing.

In a three-axis sensor, the accelerometer may be able to determine location of the ground relative to the endoscope. If the endoscope does not roll or bend up to ninety degrees, a two axis accelerometer could be also be useful. Alternatively, a one-axis sensor may be useful if the axis of the accelerometer remains perpendicular to the direction of gravity, i.e., perpendicular to the ground. Alternatively, a gyroscope may be used to measure the rate of rotation, which may then be used to calculate the articulation of the endoscopic device.

Some embodiments make use of an EM tracker in combination with the accelerometer to supplement any orientation readings from the accelerometer. In some embodiments, use of fluoroscopy to track the endoscopic tool may also supplement the registration process. As known in the art, fluoroscopy is an imaging technique that uses X-rays to obtain real-time moving images of the internal structures of a patient through the use of a fluoroscope. Two-dimensional scans generated by fluoroscopy may assist with localization in certain situations, e.g., identifying the relevant bronchi.

Tracking using fluoroscopy may be performed using a plurality of radio-opaque markers on the endoscope. Many features of the endoscope are naturally radio-opaque to x-rays, including the camera head, the control ring and pull wires; thus, the marker location together with the metallic components of the endoscope may be used to obtain a three-dimensional transformation matrix. Once registration has happened, visual images detecting branch locations may be precisely correlated to the three-dimensional model. In addition, the full branch length and branch location in 3D can be measured and enhanced in the map.

In contrast to a sensor-based approach, vision-based tracking involves using images generated by a distally-mounted camera to determine the location of the endoscopic tool. For example, in bronchoscopy, feature tracking algorithms may be used to identify circular geometries corresponding to bronchial paths and track the change of those geometries from image to image. By tracking the direction of those features as they move from image to image, the system may be able to determine which branch was selected, as well as the relative rotational and translational motion of the camera. Use of a topological map of the bronchial paths may further enhance vision-based algorithms.

In addition to feature based tracking, image processing techniques such as optical flow may also be used to identify branches in the airway topology in bronchoscopy. Optical flow is the displacement of image pixels from one image to the next in a video sequence. With respect to bronchoscopy, optical flow may be used to estimate the movement of the tip of the scope based on changes in the camera images received at the tip of the scope. Specifically, in a series of video frames, each frame may be analyzed to detect translation of the pixels from one frame to the next. For example, if the pixels in a given frame appear to translate to the left in the next frame, the algorithm would infer that the camera, and in turn the tip of the scope, moved to the right. Through comparing many frames over many iterations, movement (and thus location) of the scope may be determined.

Where stereoscopic image capture—as opposed to monocular image capture—is available, optical flow techniques may also be used to complement the pre-existing three-dimensional model of the anatomic region. Using stereoscopic image capture, the depth of the pixels in the two-dimensional captured images may be determined to build a three-dimensional map of objects in the camera view. Extrapolating to travel within an anatomical lumen, this technique enables the system to develop three-dimensional maps of the local surroundings around the endoscope while navigating in inside the patient's anatomy. These maps may be used to extend the pre-determined three-dimensional computer models where the models either are missing data or of low quality. In addition to a stereoscopic camera apparatus, depth sensors or specific lighting configurations and image capture techniques—such as RGB-D sensors or structure lighting—may need to be used.

Regardless of tracking method—either sensor-based or vision-based—tracking may be improved by using data from the endoscopic tool itself. For example, in endoscopic tool 200 from FIG. 2, the relative insertion length of sheath 201 and leader 205 may be measured from a known, starting position within the trachea (in the case of bronchoscopy). Using relative insertion length and the centerlines of a three-dimensional model of the patient's bronchial tree, the system may giving a rough estimation of the location of the working end after determining whether the endoscopic tool is located in a branch and the distance traveled down that branch. Other control information from the endoscopic tool may also be used, such as endoscope device articulation, roll, or pitch and yaw.

Real-time imaging based on different imaging modalities would further enhance navigation, particularly at the operative site. Even though tracking may assist with rough navigation to the operative site, additional modalities may be useful when more precise handling is necessary, such when attempting to biopsy a lesion. Imaging tools such as fluorescence imaging, near infrared imaging, oxygen sensors, molecular biomarker images, and contrast dye imaging may help pinpoint the exact coordinates of the lesion in the computer model, and thus assist with operating a biopsy needle at the operative site. In the absence of a precise location, the endoscopic tool may be used to biopsy the entire region of the operative site at a known depth, thus ensuring tissue from the lesion is sampled.

In some cases, the segmented CT scans, and thus the resulting computer models, do not show branches at the periphery of the lung (in the context of bronchoscopy). This may be due to insufficient inflation of the airways during a scan, or because the size of the branches is below the resolution of a CT scan (typically on the order of 1 millimeter). In practice, the robotic system may enhance the computer model during the procedure by noting the location and the position and orientation of the unmapped branch. In some embodiments, the topology structure may allow physicians to mark their location and return to that same location in order to examine the periphery branches. In some embodiments, the endoscopic camera may measure the diameter and shape of the branches based on the capture images, allowing those branches to be mapped based on position and orientation.

10. Endolumenal Procedures.

Figure 29A:
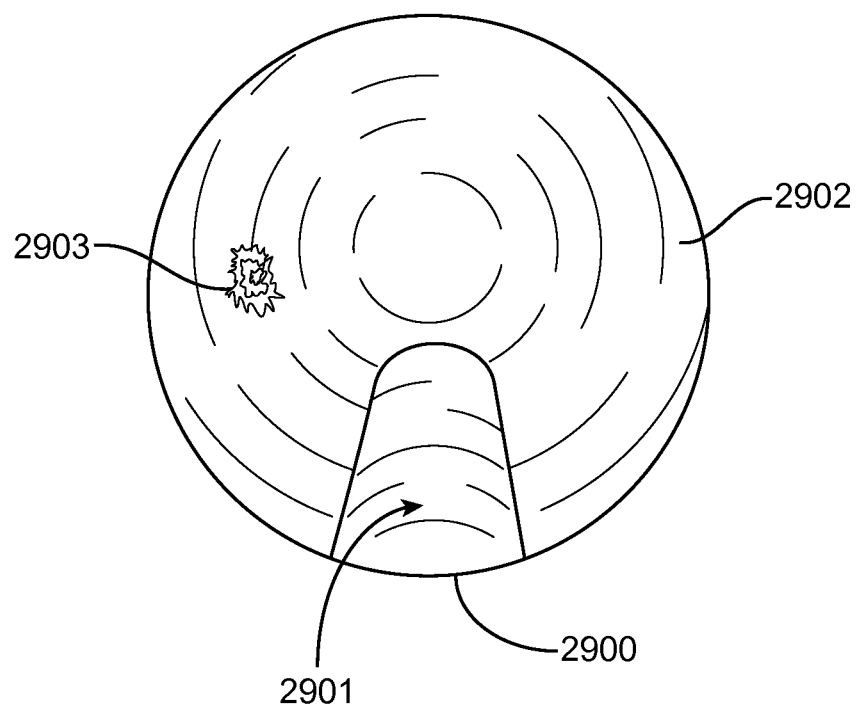
FIG. 29A illustrates the distal end of an endoscopic tool within an anatomical lumen, in accordance with an embodiment of the present invention.

FIG. 29A illustrates the distal end of an endoscopic tool within an anatomical lumen, in accordance with an embodiment of the present invention. In FIG. 29A, endoscopic tool 2900, comprising a shaft 2901 is shown navigating through an anatomical lumen 2902 towards an operative site 2903. During navigation, the shaft 2901 may be unarticulated.

Figure 29B:
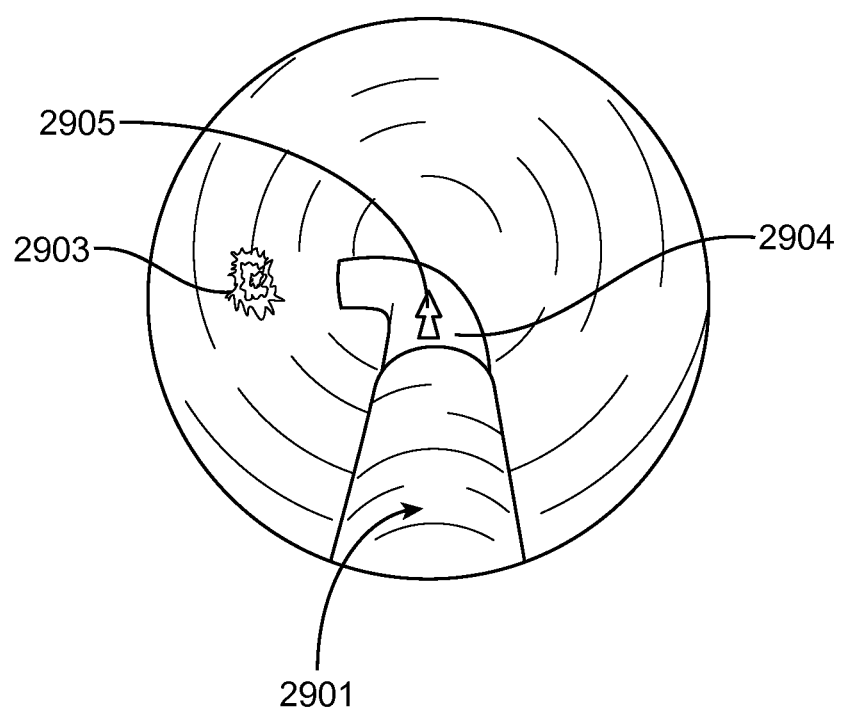
FIG. 29B illustrates the endoscopic tool from FIG. 29A in use at an operative site within an anatomical lumen, in accordance with an embodiment of the present invention.

FIG. 29B illustrates the endoscopic tool from FIG. 29A in use at an operative site within an anatomical lumen. Having reached the operative site 2903, a distal leader section 2904, longitudinally aligned with the shaft 2901, may be extended from shaft 2901 in the direction marked by arrow 2905. Distal leader section 2904 may also be articulated in order to direct tools towards operative site 2903.

Figure 29C:
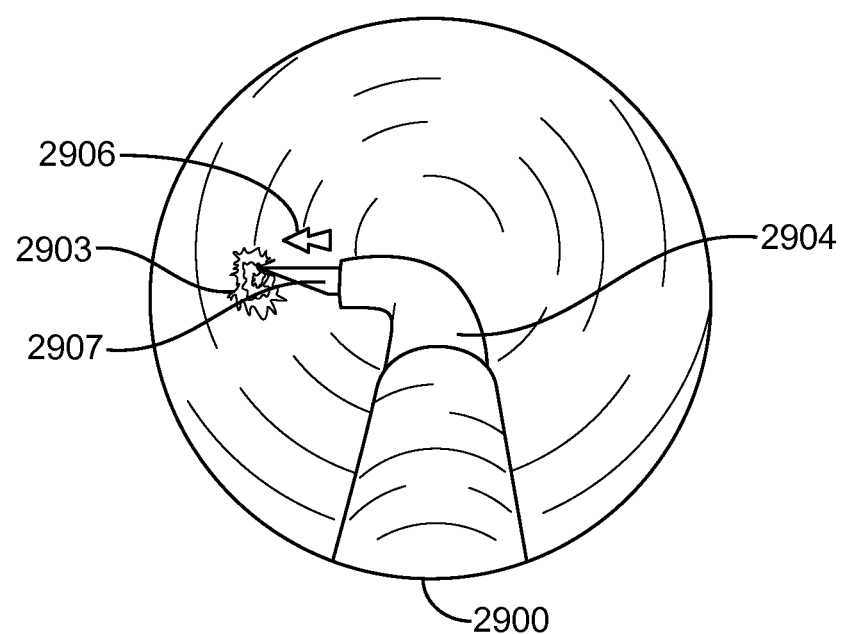
FIG. 29C illustrates the endoscopic tool from FIG. 29B in use at an operative site within an anatomical lumen, in accordance with an embodiment of the present invention.

FIG. 29C illustrates the endoscopic tool from FIG. 29B in use at an operative site within an anatomical lumen. In cases where the operative site contains a lesion for biopsy, the distal leader section 2904 may articulate in the direction marked by arrow 2906 to convey an aspiration needle 2907 to target a lesion at operative site 2903. In some embodiments, distal leader section 2904 may be articulated to direct biopsy forceps to remove samples of anatomical tissues for purposes of intraoperative evaluation. For purposes of activation of that end effector, endoscopic tool 2900 may comprise a tendon operatively coupled to the biopsy forceps.

Figure 30A:
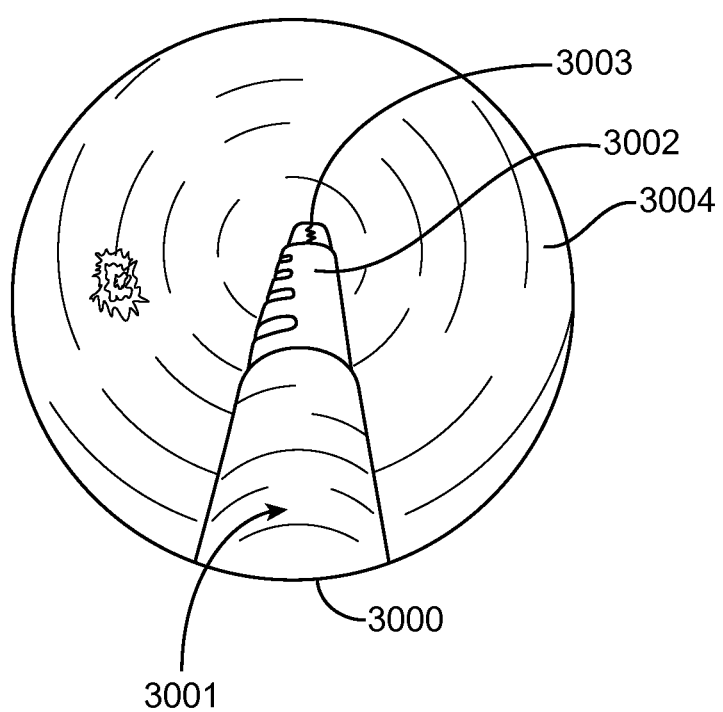
FIG. 30A illustrates an endoscopic tool coupled to a distal flexure section within an anatomical lumen, in accordance with an embodiment of the present invention.

FIG. 30A illustrates an endoscopic tool coupled to a distal flexure section within an anatomical lumen, in accordance with an embodiment of the present invention. In FIG. 30A, an endoscopic tool 3000, comprising a shaft 3001, flexure section 3002, and forceps 3003, is shown navigating through an anatomical lumen 3004 towards an operative site. During navigation, both the shaft 3001 and distal flexure section 3002 may be unarticulated as shown in FIG. 30A. In some embodiments, the flexure section 3002 may be retracted within shaft 3001. The construction, composition, capabilities, and use of flexure section 3002 is disclosed in U.S. patent application Ser. No. 14/201,610, filed Mar. 7, 2014, and U.S. patent application Ser. No. 14/479,095, filed Sep. 5, 2014, the entire contents of which are incorporated by reference.

In some embodiments, the flexure 3002 may be longitudinally-aligned with the shaft 3001. In some embodiments, the flexure 3002 may be deployed through a working channel that is off-axis (neutral axis) of shaft 3001, allowing for the flexure 3002 to operate without obscuring a camera located at the distal end of shaft 3001. This arrangement allows an operator to use a camera to articulate flexure 3002 while shaft 3001 remains stationary.

Similar to other embodiments, different tools, such as forceps 3003, may be deployed through the working channel in flexure section 3002 for use at the distal end of the flexure section 3002. In other scenarios, surgical tools such as graspers, scalpels, needles, and probes may be located at the distal end of the flexure section 3002. In endoscopic tool 3000, as in other embodiments, the tool at the distal end of the bending section may be substituted intra-operatively in order to perform multiple treatments in a single procedure.

Figure 30B:
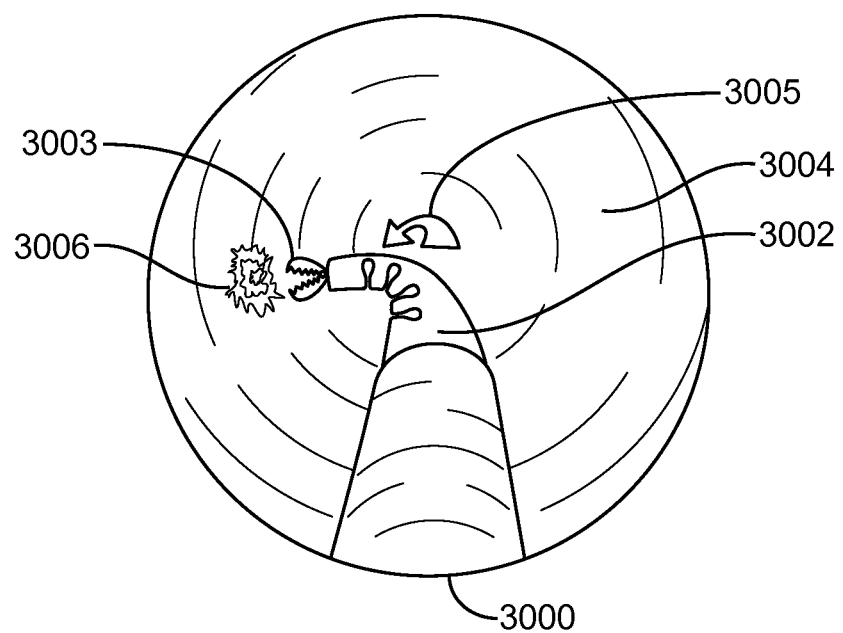
FIG. 30B illustrates an endoscopic tool from FIG. 30A with a forceps tool in use at an operative site within an anatomical lumen, in accordance with an embodiment of the present invention.

FIG. 30B illustrates an endoscopic tool from FIG. 30A with a forceps tool in use at an operative site within an anatomical lumen, in accordance with an embodiment of the present invention. Navigation of endoscopic tool 3000 through anatomical lumen 3004 may be guided by any number of the various navigational technologies discussed above. Once the endoscopic tool 3000 has reached its desired location at the operative site 3006, flexure section 3002 may articulate in the direction of arrow 3005 in order to orient forceps 3003 towards operative site 3006. Using forceps 3003, endoscopic tool 3000 may take a biopsy of the tissue at the operative site 3006.

Figure 30C:
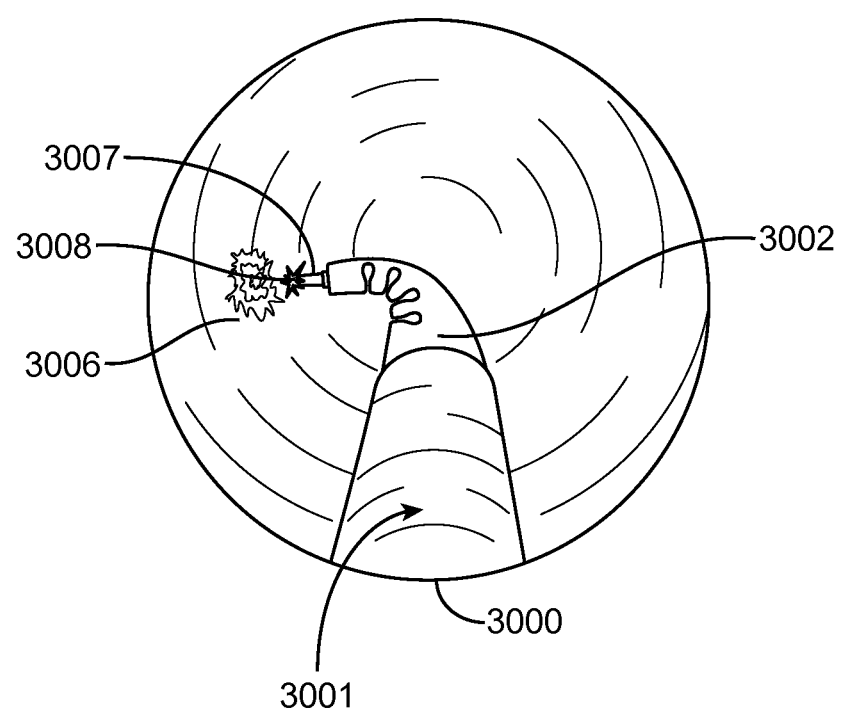
FIG. 30C illustrates an endoscopic tool from FIG. 30A with a laser device in use at an operative site within an anatomical lumen, in accordance with an embodiment of the present invention.

FIG. 30C illustrates an endoscopic tool from FIG. 30A with a laser device in use at an operative site within an anatomical lumen, in accordance with an embodiment of the present invention. Having reached the operative site 3006, the flexure section 3002 of endoscopic tool 3000 may be articulated and a laser tool 3007 may be deployed through the working channel of the shaft 3001 and flexure section 3002. Once deployed, the laser tool 3007 may be directed to operative site 3006 to emit laser radiation 3008 for purposes of tissue ablation, drilling, cutting, piercing, debriding, cutting or accessing non-superficial tissue.

11. Command Console.

As discussed with respect to system 100 from FIG. 1, an embodiment of the command console allows an operator, i.e., physician, to remotely control the robotic endolumenal system from an ergonomic position. In the preferred embodiment, the command console utilizes a user interface that both (i) enables the operator to control the robotic endoscopic tool, and (ii) displays the navigational environment from an ergonomic position.

Figure 31:
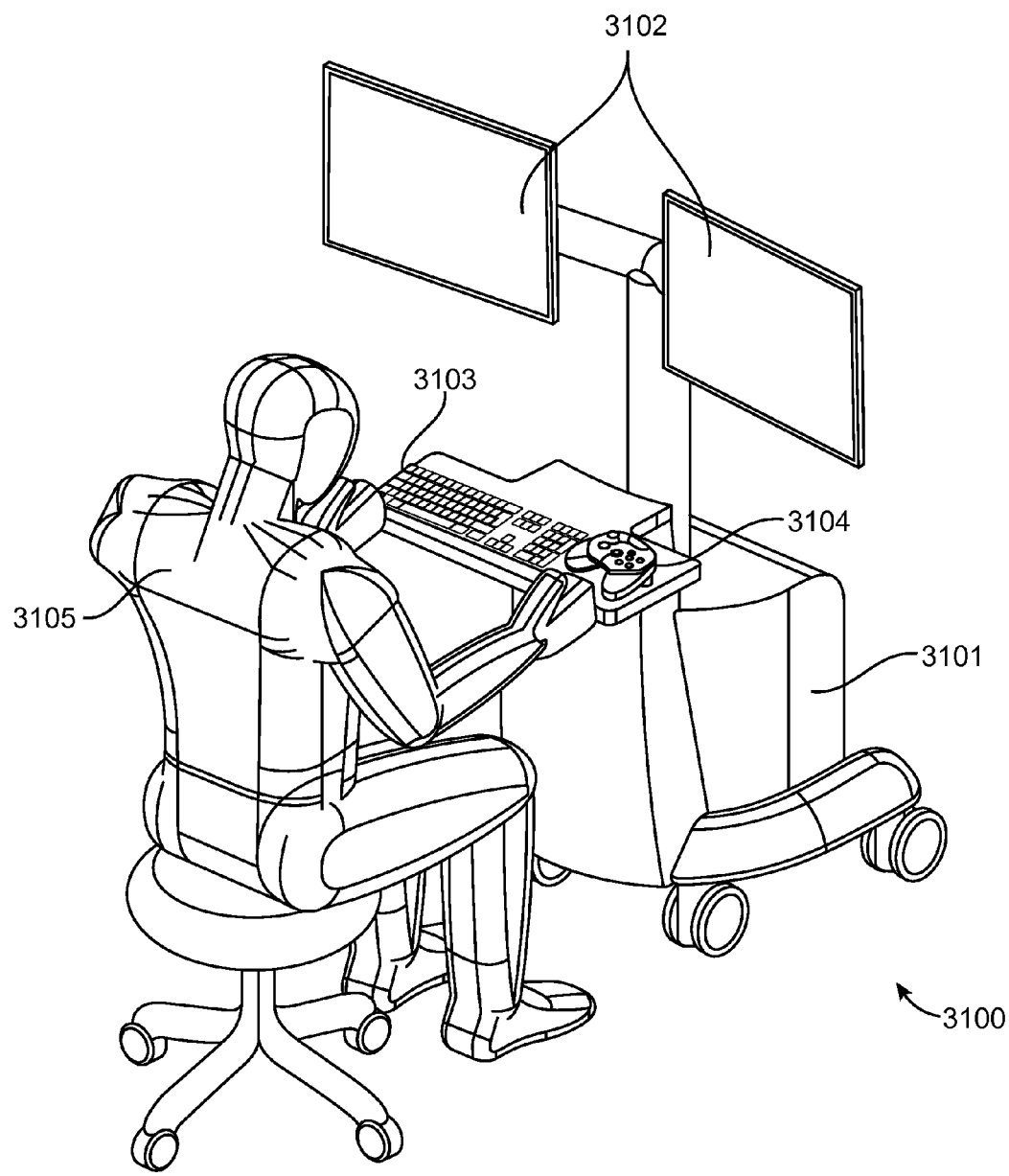
FIG. 31 illustrates a command console for a robotic endolumenal system, in accordance with an embodiment of the present invention.

FIG. 31 illustrates a command console for a robotic endolumenal system, in accordance with an embodiment of the present invention. As shown in FIG. 31, command console 3100 may comprise a base 3101, display modules, such as monitors 3102, and control modules, such as keyboard 3103 and joystick 3104. In some embodiments, the command module functionality may be integrated into the system cart with the mechanical arms, such as system cart 101 from system 100 in FIG. 1.

The base 3101 may comprise of a central processing unit, a memory unit, a data bus, and associated data communication ports that are responsible for interpreting and processing signals, such as camera imagery and tracking sensor data, from the endoscopic tool. In other embodiments, the burden of interpretation and processing signals may be distributed between the associated system cart and the command console 3100. The base 3101 may also be responsible for interpreting and processing commands and instructions from the operator 3105 through the control modules, such as 3103 and 3104.

The control modules are responsible for capturing the commands of the operator 3105. In addition to the keyboard 3103 and joystick 3104 in FIG. 31, the control modules may comprise other control mechanisms known in the art, including but not limited to computer mice, trackpads, trackballs, control pads, and video game controllers. In some embodiments, hand gestures and finger gestures may also be captured to deliver control signals to the system.

In some embodiments, there may be a variety of control means. For example, control over the endoscopic tool may be performed in either a "Velocity mode" or "Position control mode". "Velocity mode" consists of directly controlling pitch and yaw behaviors of the distal end of the endoscopic tool based on direct manual control, such as through joystick 3104. For example, right and left motions on joystick 3104 may be mapped to yaw and pitch movement in the distal end of the endoscopic tool. Haptic feedback in the joystick may also be used to enhance control in "velocity mode". For example, vibration may be sent back to the joystick 3104 to communicate that the endoscopic tool cannot further articulate or roll in a certain direction. Alternatively, pop-up messages and/or audio feedback (e.g., beeping) may also be used to communicate that the endoscopic tool has reached maximum articulation or roll.

"Position control mode" consists of identifying a location in a three-dimensional map of the patient and relying on the robotic system to robotically steer the endoscopic tool the identified location based on pre-determined computer models. Due to its reliance on a three-dimensional mapping of the patient, position control mode requires accurate mapping of the patient's anatomy.

Without using the command module 3101, the system may also be directly manipulated by manual operators. For example, during system setup, physicians and assistants may move the mechanical arms and endoscopic tools to arrange the equipment around the patient and the operating room. During direct manipulation, the system may rely on force feedback and inertia control from human operators to determine the appropriate equipment orientation.

The display modules 3102 may comprise monitors, virtual reality viewing devices, such as goggles or glasses, or other means of display visual information regarding the system and from the camera in the endoscopic tool (if any). In some embodiments, the control modules and display modules may be combined, such as in a touchscreen in a tablet or computer device. In a combined module, the operator 3105 may be able to view visual data as well as input commands to the robotic system.

In another embodiment, display modules may display three-dimensional images using a stereoscopic device, such as a visor or goggle arrangement. Using three-dimensions images, the operator may view an "endo view" of the computer model, a virtual environment of the interior of the three-dimensional computer-generated model of the patient's anatomy to approximate the expected location of the device within the patient. By comparing the "endo view" to the actual camera images, the physician may be able to mentally orient himself and confirm that the endoscopic tool is in the right location within the patient. This may give the operator a better sense of the anatomical structures around the distal end of the endoscopic tool.

In a preferred embodiment, the display modules 3102 may simultaneously display the pre-generated three-dimensional models, the pre-determined optimal navigation paths through the models, and CT scans of the anatomy at the current location of the distal end of the endoscopic tool. In some embodiments, a model of the endoscopic tool may be displayed with the three-dimensional model of the patient's anatomy, to further clarify the status of the procedure. For example, a lesion may have been identified in a CT scan where a biopsy may be necessary.

During operation, camera means and illumination means at the distal end of the endoscopic tool may generate a reference image in the display modules for the operator. Thus, directions in the joystick 3104 causing articulation and rolling of the distal end of the endoscopic tool results in an image of the anatomical features directly in front of the distal end. Pointing the joystick 3104 up may raise the pitch of the distal end of the endoscopic tool with the camera, while pointing the joystick 3104 down may decrease the pitch.

The display modules 3102 may automatically display different views of the endoscopic tool depending on the operators' settings and the particular procedure. For example, if desired, an overhead fluoroscopic view of the endolumenal device may be displayed during the final navigation step as it approached the operative region.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A method for constructing a medical device, comprising:
   providing a first elongated body;
   providing a plurality of second elongated bodies
   laying the plurality of second elongated bodies at a pitch in a helical pattern around the first elongated body;
   braiding a layer of braid wire around the first elongated body and the plurality of second elongated bodies to generate a braided composite; and
   removing the plurality of second elongated bodies from the braided composite in order to generate a helical lumen within the braided composite.

2. The method of claim 1, further comprising:
removing the first elongated body from the braided composite in order to generate a central lumen in the braided composite.

3. The method of claim 2, wherein the central lumen is configured to convey tools and sensors to the distal end of the braided composite.

4. The method of claim 1, further comprising:
sheathing the braided composite with an outer jacket.

5. The method of claim 1, further comprising:
casting an outer jacket around the braided composite.

6. The method of claim 1, wherein the pitch of the helical pattern is predetermined.

7. The method of claim 1, wherein the pitch of the helical pattern varies along the length of the first elongated body.

8. The method of claim 7, wherein the pitch of the helical pattern is parallel to the first elongated body along a section of braided composite that is configured to be actuated.

9. The method of claim 1, further comprising:
inserting a pull wire within the helical lumen.

10. The method of claim 9, further comprising:
attaching the pull wire near the distal end of the braided composite, such that tension along the pull wire results in a compressive force along the braided composite.

11. The method of claim 10, wherein the helical lumen is configured to radially distribute the compressive force along the braided composite arising from tension in the pull wire.

12. The method of claim 1, further comprising:
attaching a digital camera at the distal end of the braided composite.

13. The method of claim 1, further comprising:
attaching light sources configured to be used with the digital camera at the distal end of the braided composite.

14. The method of claim 1, further comprising:
inserting the first elongated body and the second elongated body into a braiding machine;
wherein the braiding machine comprises a feed tube and a nose cone.

15. The method of claim 14, further comprising:
advancing the plurality of second elongated bodies through respective side holes in the nose cone.

16. The method of claim 15, further comprising:
advancing the first elongated body through the feed tube and a central hole in the nose cone.

17. The method of claim 16, further comprising:
rotating the first elongated body;
wherein the rotating occurs as the plurality of second elongated bodies are laid around the first elongated body.

18. The method of claim 16, further comprising:
rotating the nose cone;
wherein the rotating occurs as the plurality of second elongated bodies are laid around the first elongated body.

19. The method of claim 18, wherein the nose cone is concentrically aligned with the feed tube.

20. The method of claim 19, wherein the nose cone is fixedly coupled to the feed tube, such that the feed tube rotates if the nose cone rotates.

21. The method of claim 20, wherein the plurality of second elongated bodies are constructed from at least one of braiding and thermoset polymer.

22. The method of claim 21, wherein the plurality of second elongated bodies are each coated with a lubricious coating.

* * * * *

UNITED STATES PATENT AND TRADEMARK OFFICE
CERTIFICATE OF CORRECTION

PATENT NO.        : 9,844,412 B2
APPLICATION NO.   : 14/542387
DATED             : December 19, 2017
INVENTOR(S)       : Joseph Daniel Bogusky It is certified that error appears in the above-identified patent and that said Letters Patent is hereby corrected as shown below:

In the Claims

Column 34 at Line 59, Claim 1, change "bodies" to --bodies;--.

Signed and Sealed this
Seventeenth Day of April, 2018

Andrei Iancu
*Director of the United States Patent and Trademark Office*